United States Patent
Chen

(10) Patent No.: US 9,617,511 B2
(45) Date of Patent: Apr. 11, 2017

(54) TISSUE-SPECIFIC DIFFERENTIATION MATRICES AND USES THEREOF

(75) Inventor: Xiao-Dong Chen, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/821,288

(22) PCT Filed: Sep. 6, 2011

(86) PCT No.: PCT/US2011/050550
§ 371 (c)(1),
(2), (4) Date: Apr. 9, 2013

(87) PCT Pub. No.: WO2012/033763
PCT Pub. Date: Mar. 15, 2012

(65) Prior Publication Data
US 2013/0195814 A1    Aug. 1, 2013

Related U.S. Application Data

(60) Provisional application No. 61/380,691, filed on Sep. 7, 2010, provisional application No. 61/390,558, filed on Oct. 6, 2010.

(51) Int. Cl.
*C12N 5/073* (2010.01)
*C12N 5/0775* (2010.01)

(52) U.S. Cl.
CPC ......... *C12N 5/0605* (2013.01); *C12N 5/0663* (2013.01); *C12N 5/0665* (2013.01); *C12N 2502/1323* (2013.01); *C12N 2533/52* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 5,843,780 A | 12/1998 | Thomson | 435/363 |
| 6,030,836 A | 2/2000 | Thiede et al. | 435/347 |
| 6,200,806 B1 | 3/2001 | Thomson | 435/366 |
| 6,284,284 B1* | 9/2001 | Naughton | 424/520 |
| 6,387,367 B1 | 5/2002 | Davis-Sproul et al. | 424/93.1 |
| 6,800,480 B1 | 10/2004 | Bodnar et al. | 435/325 |
| 6,911,201 B1 | 6/2005 | Merchav et al. | 424/93.7 |
| 8,084,023 B2 | 12/2011 | Chen et al. | 424/93.1 |
| 2003/0113812 A1* | 6/2003 | Hemperly | 435/7.2 |
| 2005/0013872 A1 | 1/2005 | Freyman | 424/549 |
| 2005/0076396 A1* | 4/2005 | Katz | C12N 5/0068 800/8 |
| 2005/0265980 A1 | 12/2005 | Chen et al. | 424/93.7 |
| 2007/0128722 A1* | 6/2007 | Lin et al. | 435/366 |
| 2008/0038352 A1 | 2/2008 | Simpson et al. | 424/484 |
| 2008/0175816 A1 | 7/2008 | Chen et al. | 424/93.1 |
| 2009/0081784 A1 | 3/2009 | Vodyanyk et al. | 435/372 |
| 2010/0093077 A1 | 4/2010 | McClelland et al. | 435/325 |

FOREIGN PATENT DOCUMENTS

| | | |
|---|---|---|
| WO | WO/2005/094898 | 2/2005 |
| WO | WO 2009/052459 | 4/2009 |
| WO | WO/2009/052459 | 4/2009 |

OTHER PUBLICATIONS

Philp, D. et al. 2005. Complex Extracellular Matrices Promote Tissue-Specific Stem Cell Differentiation. Stem Cells 23:288-296. specif. p. 288.*

Phillips, C.L. et al. 1994. Effects of Ascorbic Acid on Proliferation and Collagen Synthesis in Relation to the Donor age of Human Dermal Fibroblasts. Journal of Investigative Dermatology 103:228-232. specif. pp. 228-229.*

Tang, J. et al. 2006. Mesenchymal stem cells participate in angiogenesis and improve heart function in rat model of myocardial ischemia with reperfusion. European Journal of Cardio-thoracic Surgery 30:353-361. specif. pp. 353-354, 360.*

Zhang, X. et al. 2002. Cyclooxygenase-2 regulates mesenchymal cell differentiation into the osteoblast lineage and is critically involved in bone repair. Journal of Clinical Investigations 109:1405-1415. specif. p. 1409.*

Song, M.-K. et al. 1990. Propagation of fetal human RPE cells: Preservation of original culture morphology after serial passage. Journal of Cellular Physiology 143: 196-203. specif. p. 197.*

Ingber, D.E. et al. 1989. Mechanochemical switching between growth and differentiation during fibroblast growth factor-stimulated angiogenesis In Vitro: Role of extracellular matrix. Journal of Cell Biology 109:317-330. specif. p. 317.*

Chen, X.-D. et al. 2007. Extracellular matrix made by bone marrow cells facilitates expansion of marrow-derived mesenchymal progenitor cells and prevents their own differentiation into osteoblasts. Journal of Bone and Mineral Research 22(12): 1943-1956. specif. pp. 1943-1945, 1950.*

Merriam-Webster Online Dictionary. Three-dimensional. Datasheet [online]. Merriam-Webster, Inc., Copyright 2015 [retrieved on Feb. 12, 2015]. Retrieved from the Internet: <URL: http://www.merriam-webster.com/dictionary/three-dimensional> pp. 1-2.*

(Continued)

*Primary Examiner* — Renee Claytor
*Assistant Examiner* — Sharon M Papciak
(74) *Attorney, Agent, or Firm* — Norton Rose Fulbright US LLP

(57) ABSTRACT

In some aspects, this invention provides a method of making a bone marrow-derived tissue-specific stem cell proliferation, expansion, isolation and rejuvenation extracellular matrix. In other aspects, this invention provides a method of making a tissue-specific fibroblast-derived stem cell differentiation extracellular matrix. Also provided are methods of using such a cell-derived preservation or differentiation matrices to induce tissue-specific differentiation of pluripotent cells, repair damaged tissue, and treat a subject having a physiologic deficiency using the same.

37 Claims, 35 Drawing Sheets

(56) References Cited

OTHER PUBLICATIONS

Gong, J. et al. 2008. Effects of extracellular matrix and neighboring cells on induction of human embryonic stem cells into retinal or retinal pigment epithelial progenitors. Experimental Eye Research 86: 957-965. specif. p. 957.*
Calvi, L.M. et al. 2001. Activated parathyroid hormone/parathyroid hormone-related protein receptor in osteoblastic cells differentially affects cortical and trabecular bone. Journal of Clinical Investigation 107(3): 277-286. specif. pp. 277, 284.*
Evans, N.D. et al. Feb. 9, 2010. Extracellular matrix-mediated osteogenic differentiation of murine embryonic stem cells. Biomatenals 31: 3244-3252. specif. pp. 3244, 3245, 3249.*
Liu, T.M. et al. 2007. Identification of common pathways mediating differentiation of bone marrow- and adipose tissue-derived human mesenchymal stem cells into three mesenchymal lineages. Stem Cell Genetics and Genomics 25: 750-760. specif. pp. 750, 756.*
Abbott, *Nature*, 424:870-872, 2003.
Abe et al., *J Bone Miner Res.*, 15:663-673, 2000.
Baksh et al., *J. Cell Mol. Med.*, 8:301-316, 2004.
Banfi et al., *Exp. Hematol.*, 28:707-715, 2000.
Bennett et al., *Histol. Histopathol.*, 16:603-611, 2001.
Bianchi et al., *Exp. Cell Res.*, 287:98-105, 2003.
Campbell et al., *J. Clin. Invest.*, 75:2085-2090, 1985.
Chen et al., *FASEB J.*, 18:948-958, 2004.
Chen et al., *J. Bone Miner Res.*, 17:331-34, 2002.
Chen, *Birth Defects Res.* 90:45-54, 2010.
Chen, et al., *J Bone Min Res.* 22(12):1943-56, 2007.
Chow et al., *Biophys. J.*, 81:675-684, 2001.
Clark and Keating, *Ann. NY Acad. Sci.*, 770:70-78, 1995.
Cukierman et al., *Science*, 294:1708-1712, 2001.
D'Ippolito et al., *Bone*, 39:513-522, 2006.
Dallas et al., *J. Biol. Chem.*, 277:21352-21360, 2002.
Decaris, et al., *Acta Biomaterialia*. 8:744-52, 2012.
Di Gregorio et al., *J. Clin. Invest.*, 107:803-812, 2001.
DiGirolamo et al., *Br. J. Haematol.*, 107:275-281, 1999.
Friedenstein et al., *Transplantation*, 17:331-339, 1974.
Fuchs et al., *Cell*, 116:769-778, 2004.
Gordon, *Br. Haematol.*, 7:1-4, 1988.
Gospodarowicz et al., *J. Cell Biol.*, 99:947-961, 1984.
Grayson et al., *Biotechnol. Prog.*, 20:905-912, 2004.
Gronthos et al., *J. Bone Miner Res.*, 18:716-722, 2003.
Hamilton and Campbell, *Anat. Rec.*, 231(2):218-24, 1991.
He, et al., *Tissue Engineering*. 15(12):3809-3821, 2009.
Hocking et al., *Matrix Biol.*, 17:1-19, 1998.
Ingber & Folkman, *J Cell Biol.* 109:317-330, 1989.
International Preliminary Report on Patentability in International Application No. PCT/US2011/050550 mailed Mar. 21, 2013.
Izadpanah et al., *Cancer Res.*, 68:4229-4238, 2008.
Jarrahy et al., *Am. Physiol. Cell Physiol.*, 289:C408-C414, 2005.
Jiang et al., *Nature*, 418:41-49, 2002.
Kim et al., *Arch. Pharm. Res.*, 32:117-126, 2009.
Klein, *Experientia*, 51:914-926, 1995.
Knopp et al., *Endocrinology*, 146:1983-1990, 2005.
Ksiazek, *Rejuvenation Res.*, 12(2):105-16, 2009.
Lai, et al., *Stem Cells and Development*. 19(7):1095-1107, 2010.
Lee et al., *Biochim. Biophys. Acta.*, 1428:300-304, 1999.
Mao and Schwarzbauer, *J. Cell Sci.*, 118:4427-4436, 2005.
Miura et al., *Stem Cells*, 24:1095-1103, 2006.
Nili et al., *Am. J. Pathol.*, 163:869-878, 2003.
Okita et al., *Nature*, 448:313-317, 2007.
Peister et al., *Blood*, 103:1662-1668, 2004.
Philp et al., *Stem Cells*. 23:288-296, 2005.
Rosland et al., Cancer Res., 69(13):5331-9, 2009.
Rubio et al., *Cancer Res.*, 65:3035-3039, 2005.
Santra et al., *J. Biol. Chem.*, 277:35671-35681, 2002.
Search Report and Written Opinion in International Application No. PCT/US2011/050550 mailed Apr. 17, 2012.
Sekiya et al., *Stem Cells*, 20:530-541, 2002.
Sotiropoulou et al., *Stem Cells*, 24:462-471, 2006.
Sreejit & Verma, *Cell Tiss Res*. 353:443-56, 2013.
Sreejit & Verma, *Euro Cell Mat*. 21:107-121, 2011.
Sun, et al., *FASEB J.* 25(5):1474-85, 2011.
Suzawa et al., *Endocrinology*, 140:2125-2133, 1999.
Takahashi et al., *Cell*, 131: 861-872, 2007.
Vanwinkle, et al., *In Vitro Cell Dev Biol*. 32:478-85, 1996.
Wexler et al., *Br. J. Haematol.*, 121:368-374, 2003.
Yu et al., *Science*, 318:1917-1920, 2007.
Zeitouni, et al., *Sci Transl Med*. 4:132ra55, 2012.
Chen et al. "Extracellular matrix provides an optimal niche for the maintenance and propagation of mesenchymal stem cells", *Birth Defects Research Part C: Embryo Today: Reviews*, 90(1):45-54, 2010.
Choi et al., "The chondrogenic differentiation of mesenchymal stem cells on an extracellular matrix scaffold derived from porcine chondrocytes", *Biomaterials*, 31(20):5355-5365, 2010.
Hong, et al., "In vitro differentiation of human umbilical cord blood-derived mesenchymal stem cells in hepatocyte-like cells" Biochemical and Biophsical Research Communications. 330:1153-61, 2005.
Koch, et al., "Isolation of mesenchymal stem cells from equine umbilical cord blood" BMC Biotechnology 7:26, 2007.
Lee, et al., "Mesenchymal stem cells from cyropreserved human umbilical cord blood" Biochemical and Biophysical Res Comm 320:273-78, 2004.
Lu, et al., "Isolation and characterization of human umbilical cord mesenchymal stem cells with hematopoiesis-supportive function and other potentials" Hematologica. 91:1017-26, 2006.
Office action in Australian Patent Application No. 2011299327 dated Apr. 14, 2014.
Office action in Australian Patent Application No. 2011299327 dated May 15, 2015.
Stern et al., "The influence of extracellular matrix derived from skeletal muscle tissue on the proliferation and differentiation of myogenic progenitor cells ex vivo", *Biomaterials*, 30(12):2393-2399, 2009.
Supplemental European Search Report issued in European Patent Application No. 11824020.9, dated Feb. 18, 2014.
Zhang et al., "Tissue-specific extracellular matrix coatings for the promotion of cell proliferation and maintenance of cell phenotype", *Biomaterials*, 30(23-24):4021-4028, 2009.

* cited by examiner

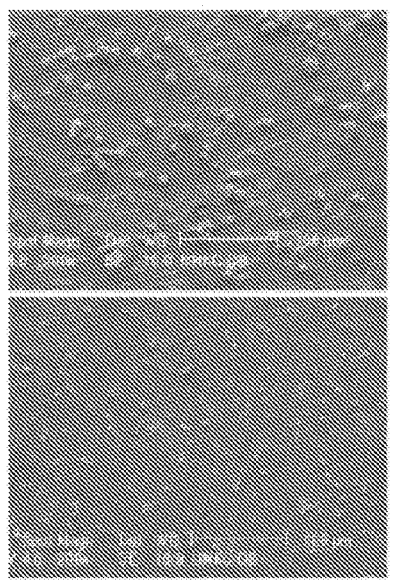
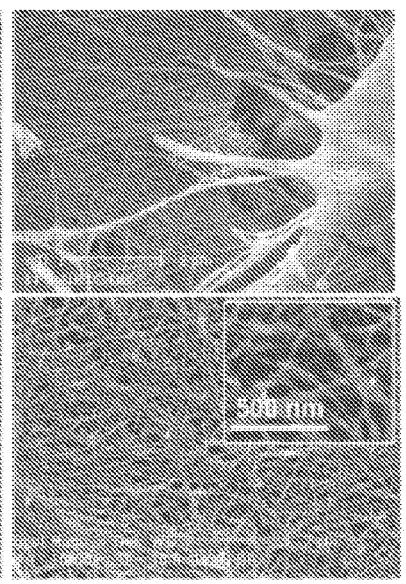
FIGs. 1A-B

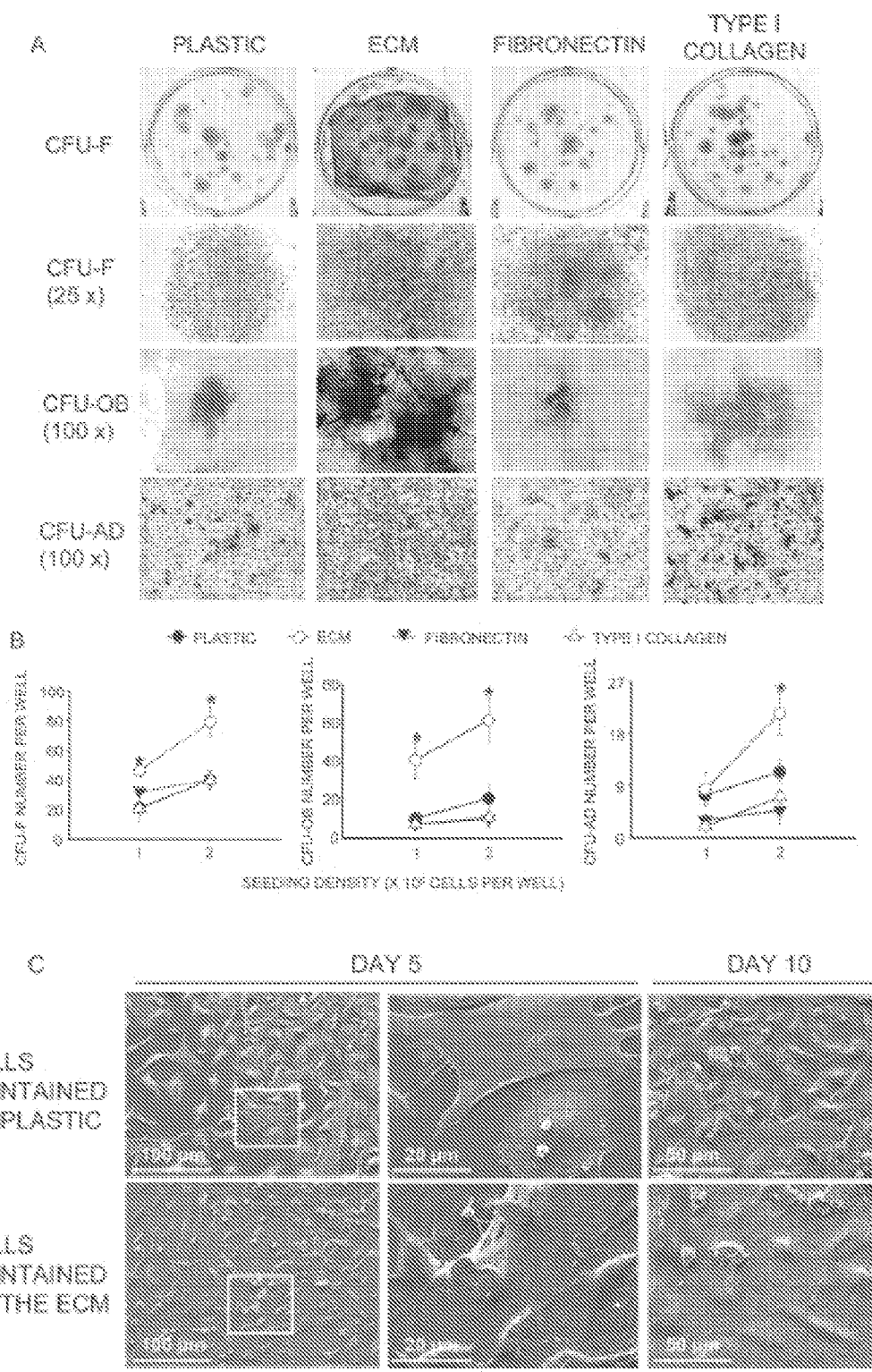
FIGs. 2A-C

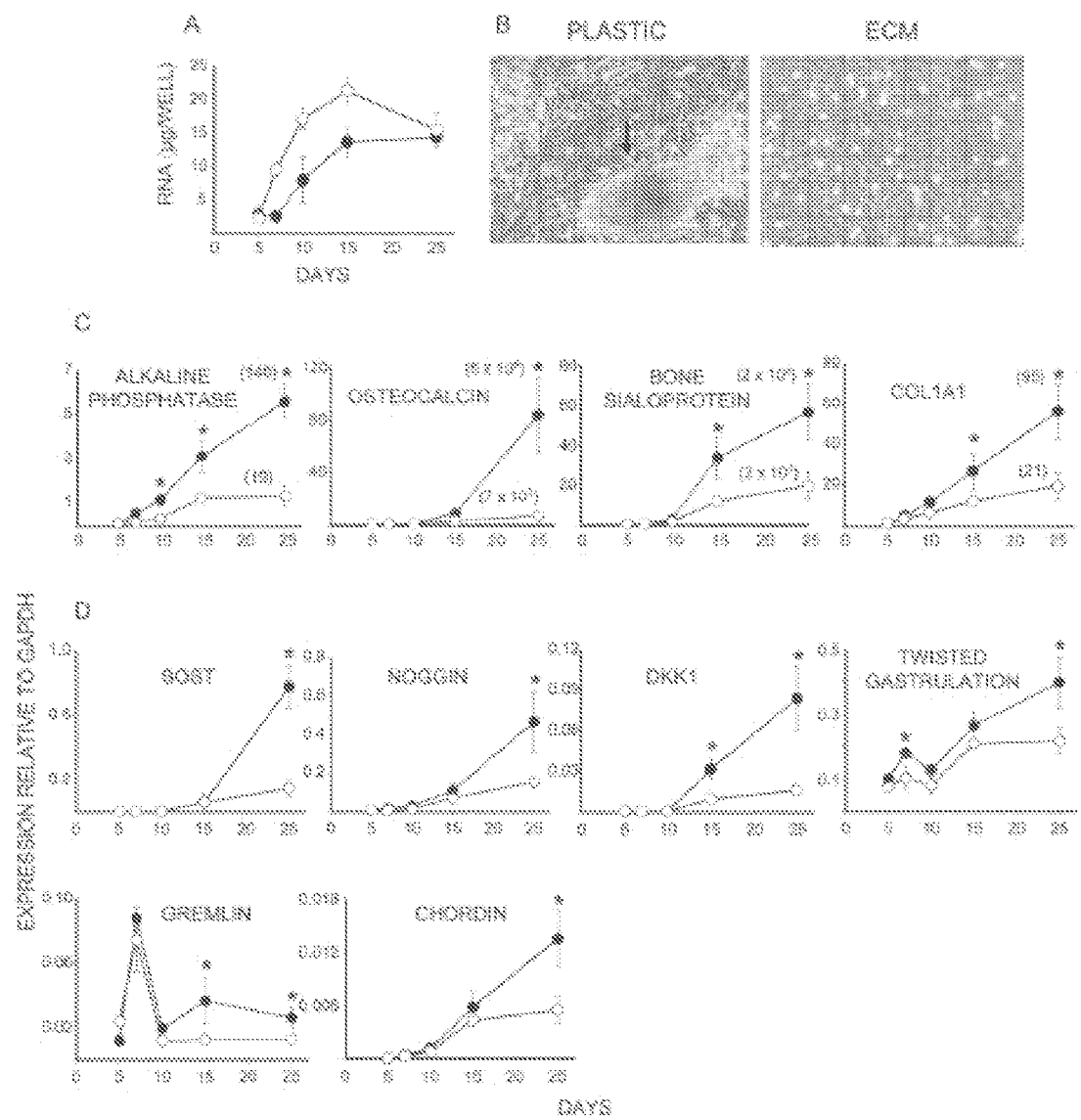
FIGs. 3A-D

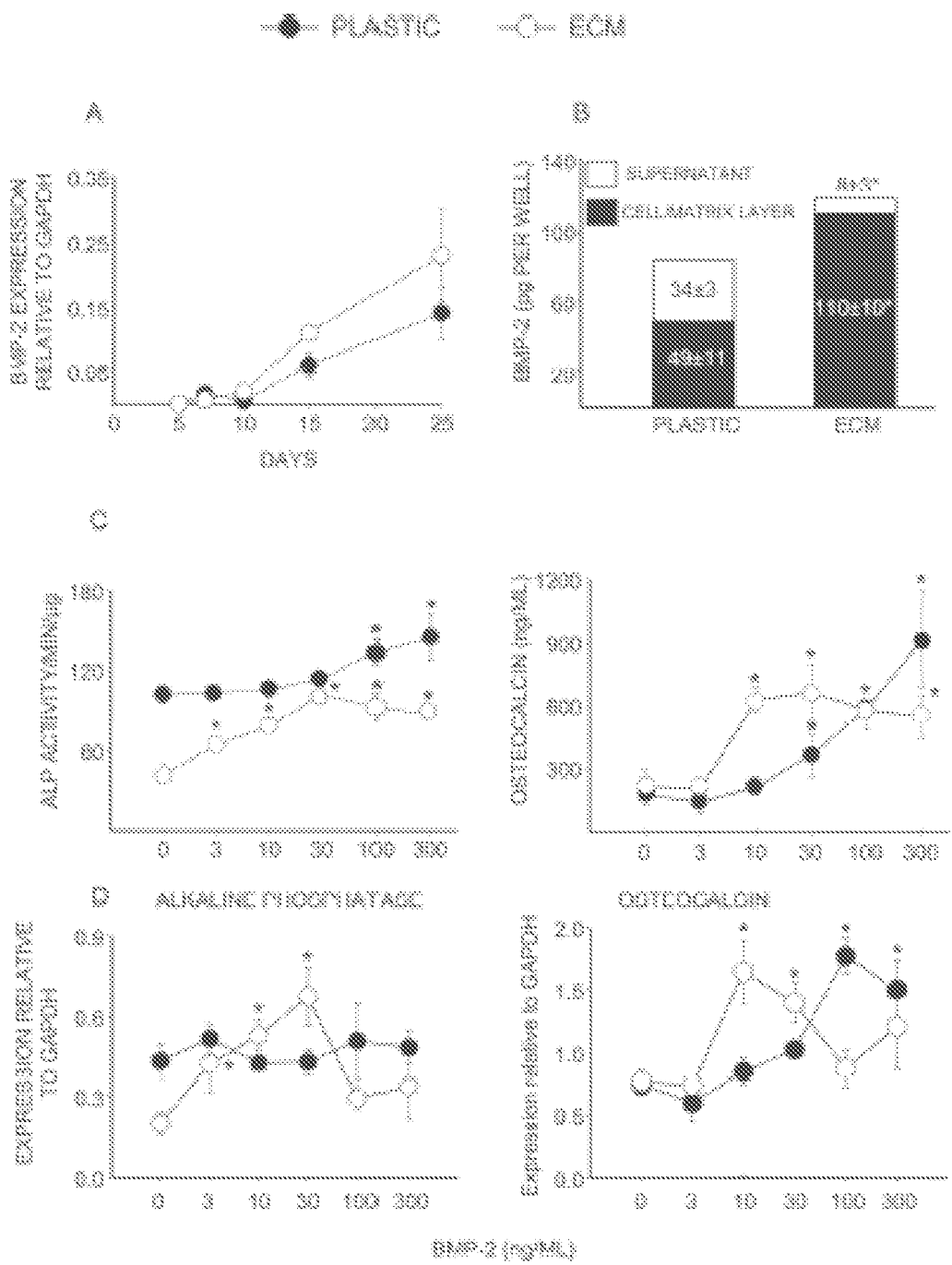
FIGs. 4A-D

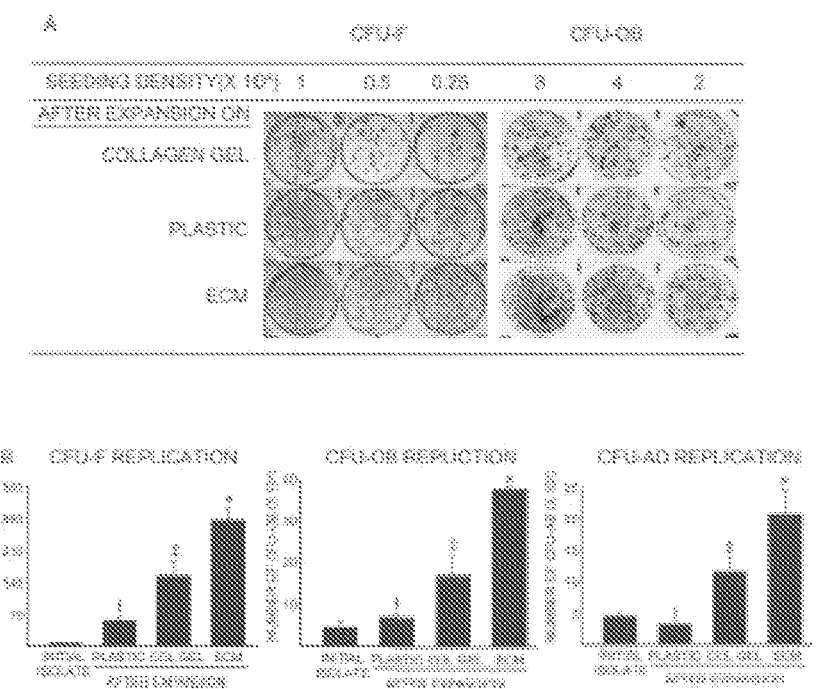
FIGs. 5A-B
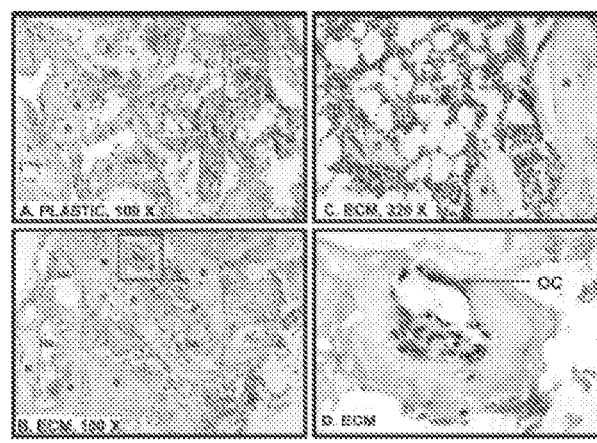
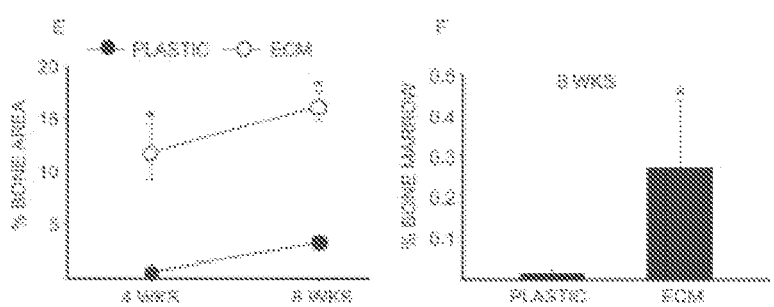
FIGs. 6A-F

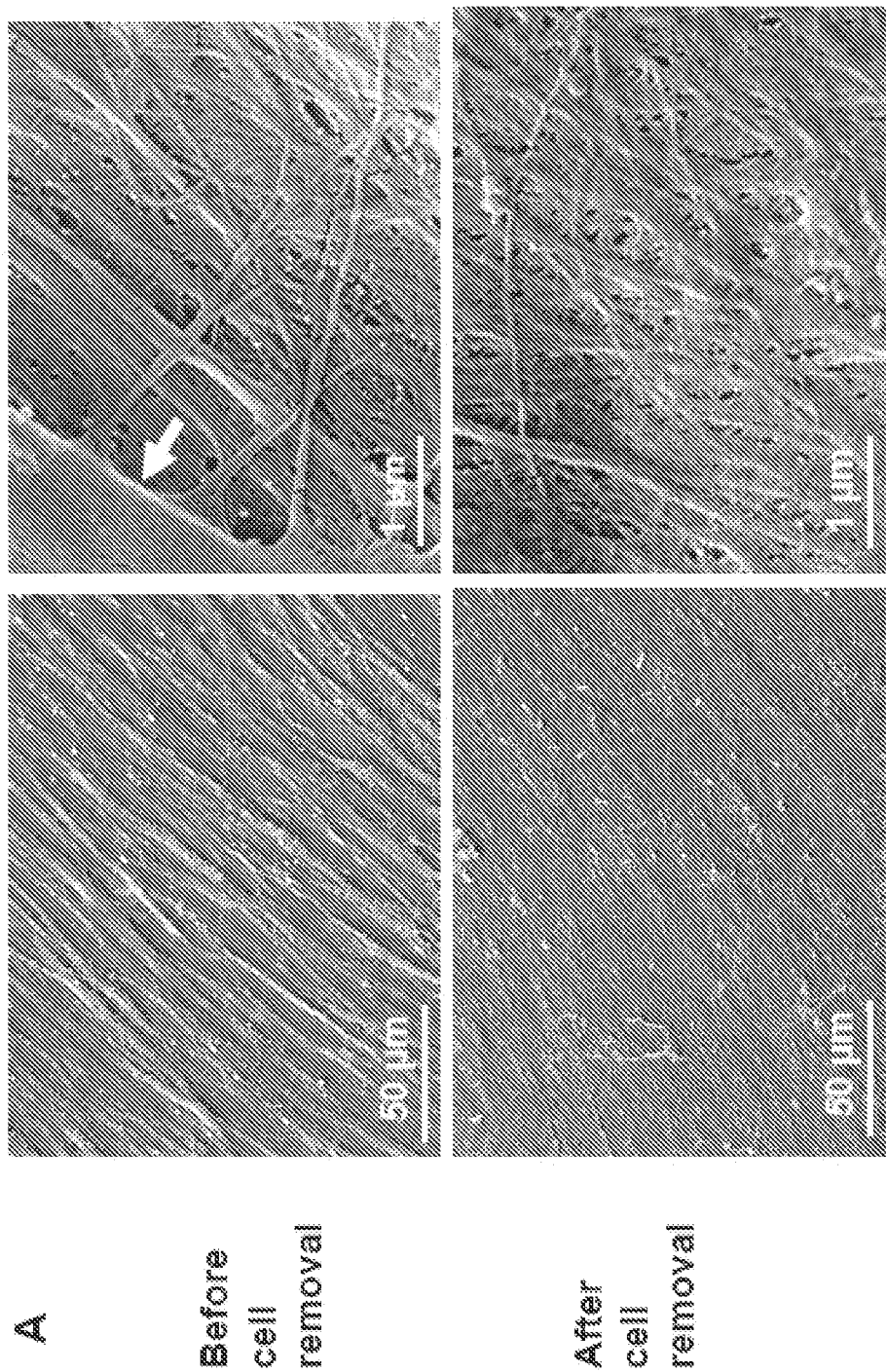

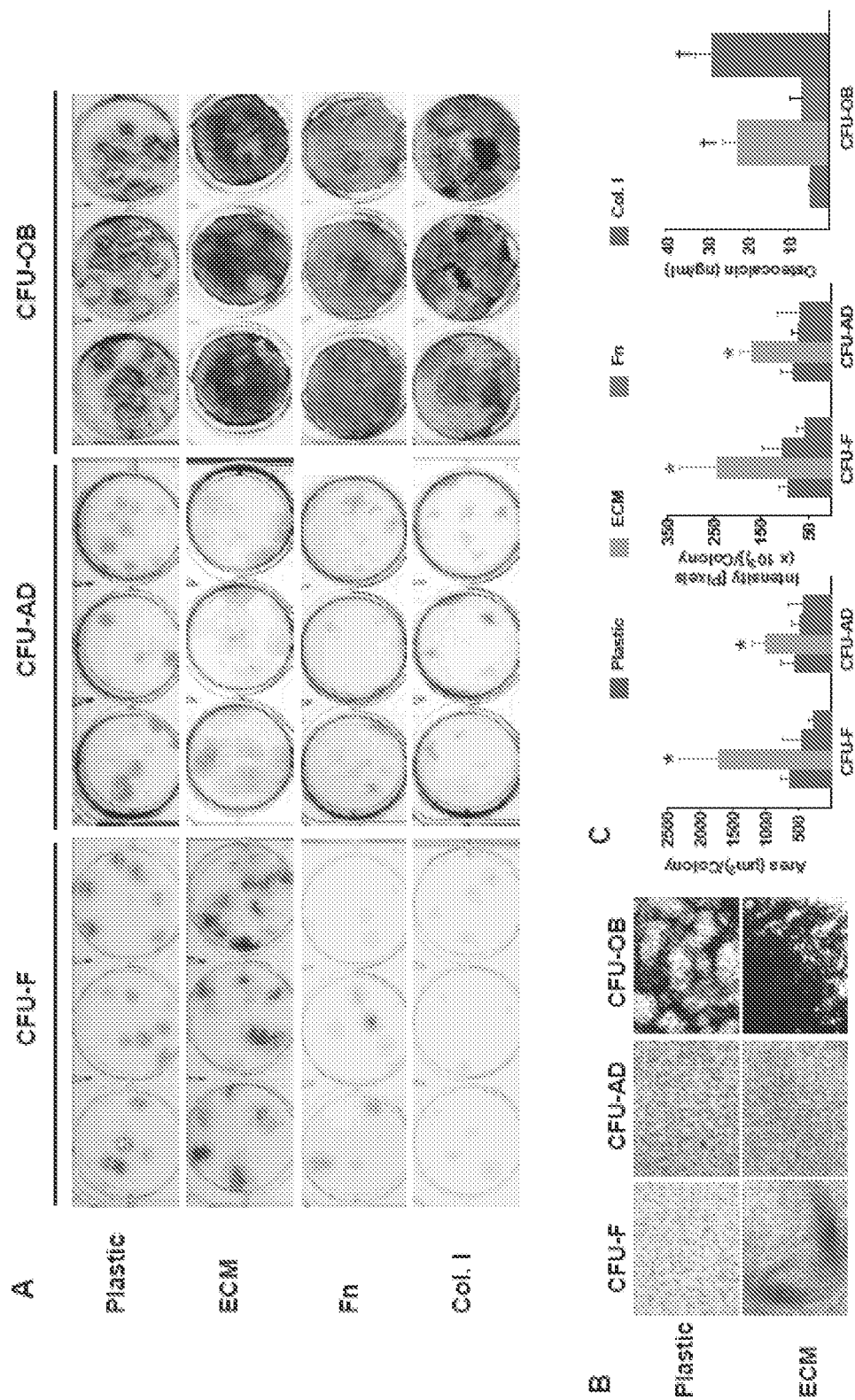
FIGs. 8A-C

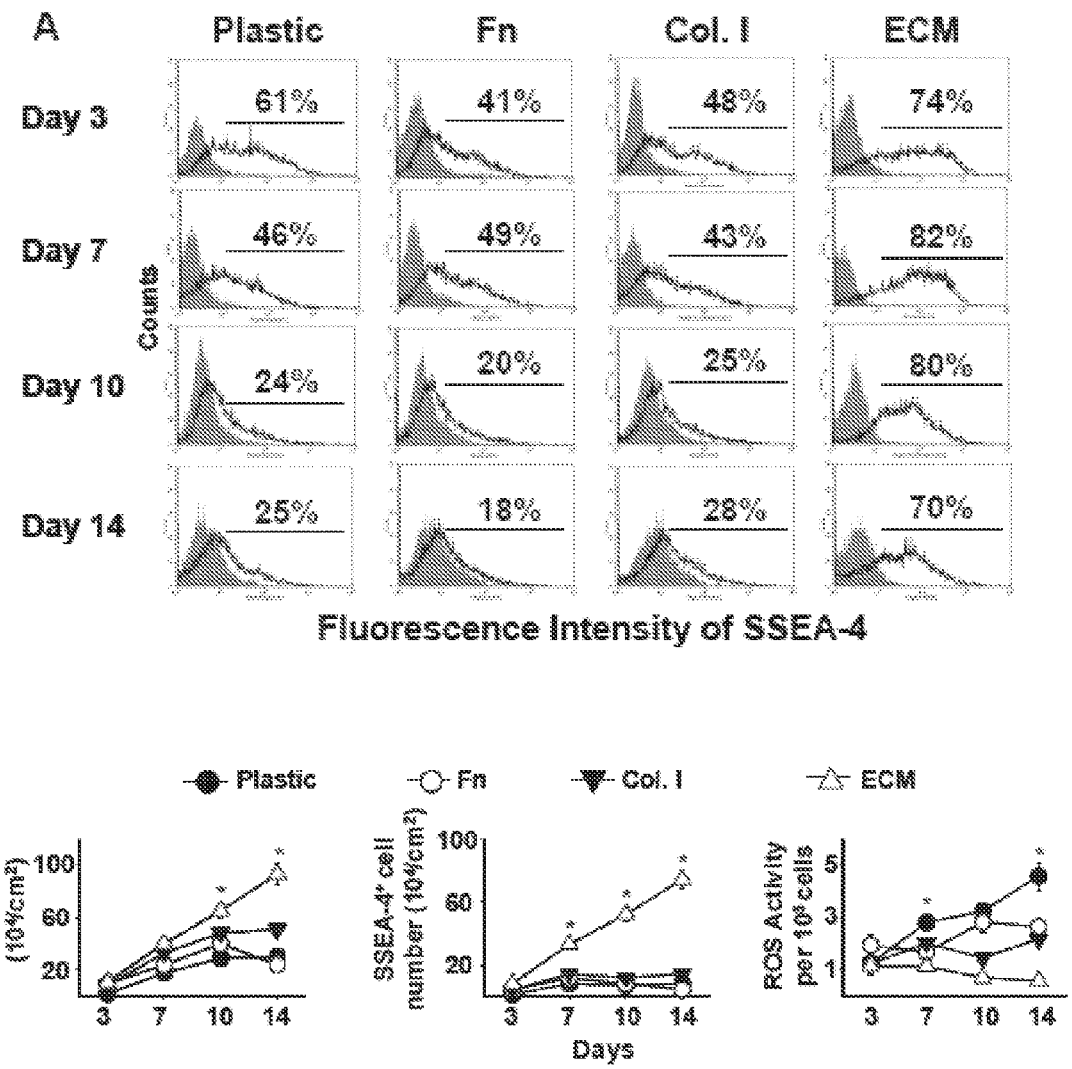
FIGs. 9A-B

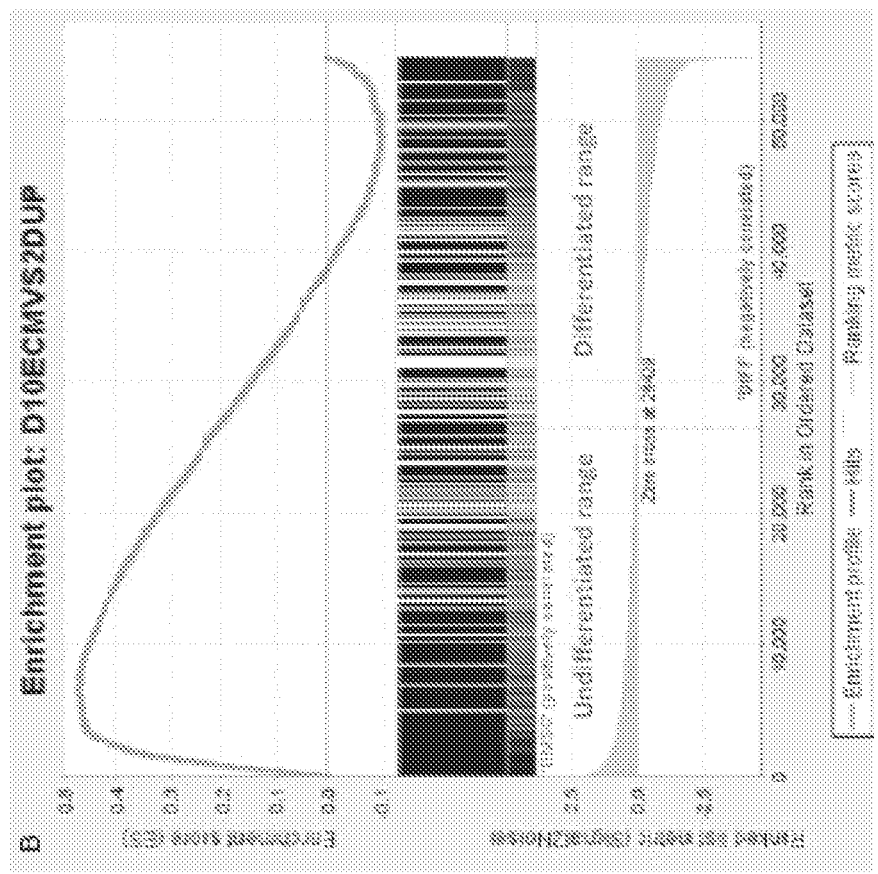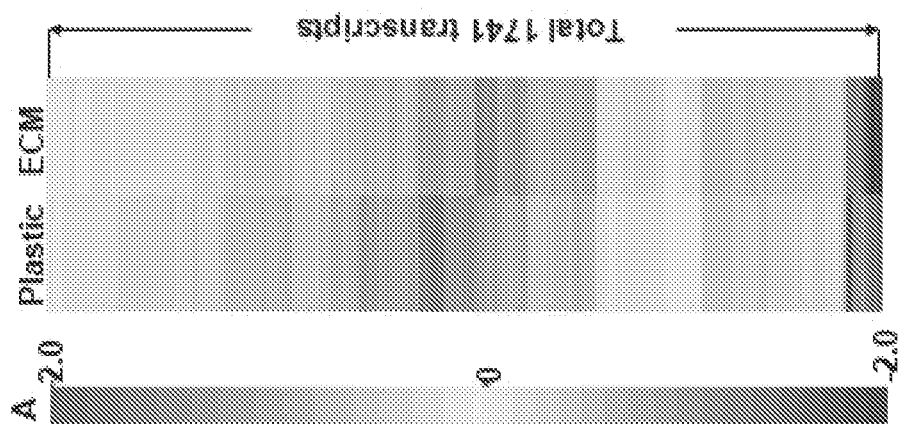
FIGS. 11A-B

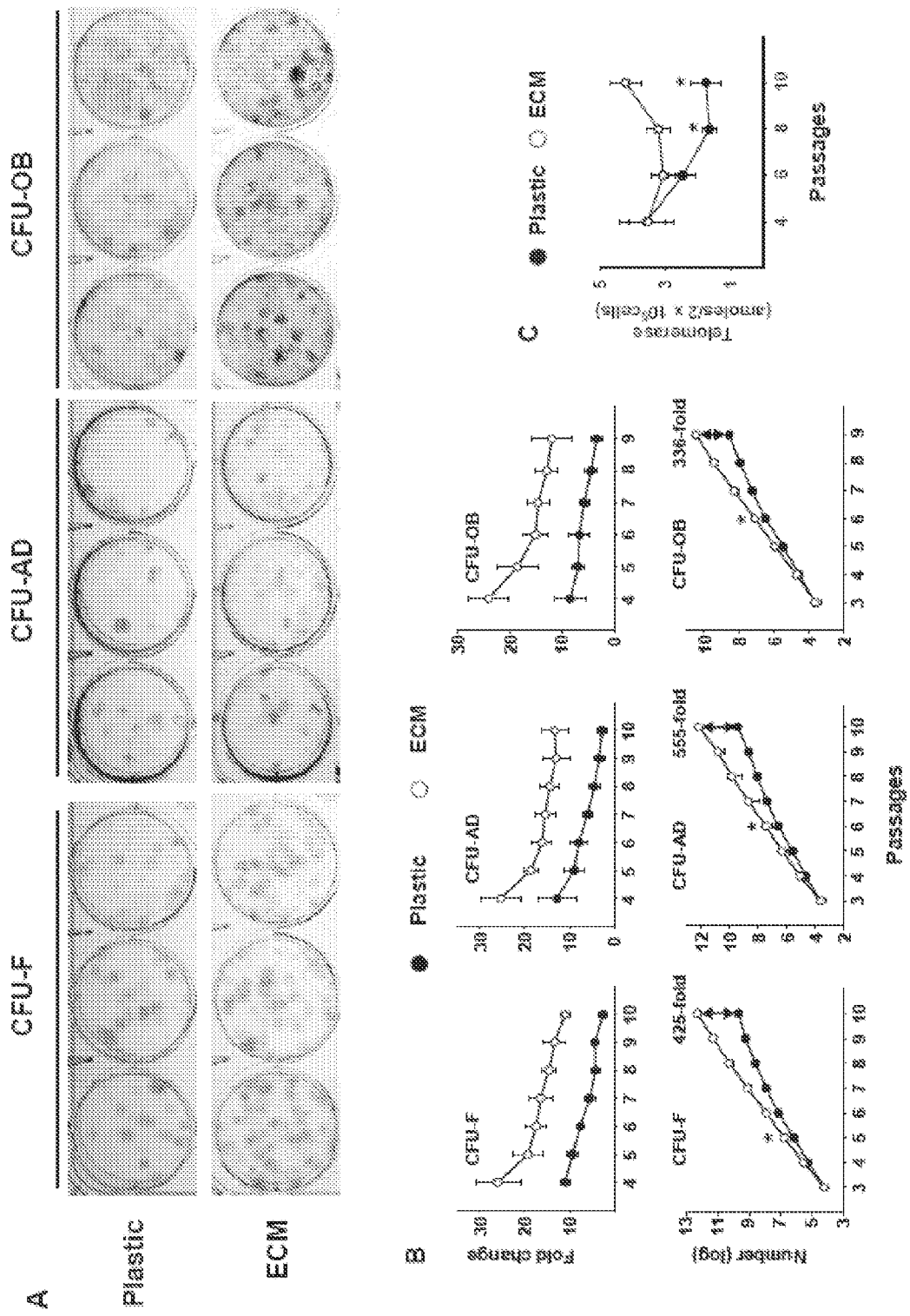
FIGs. 12A-C

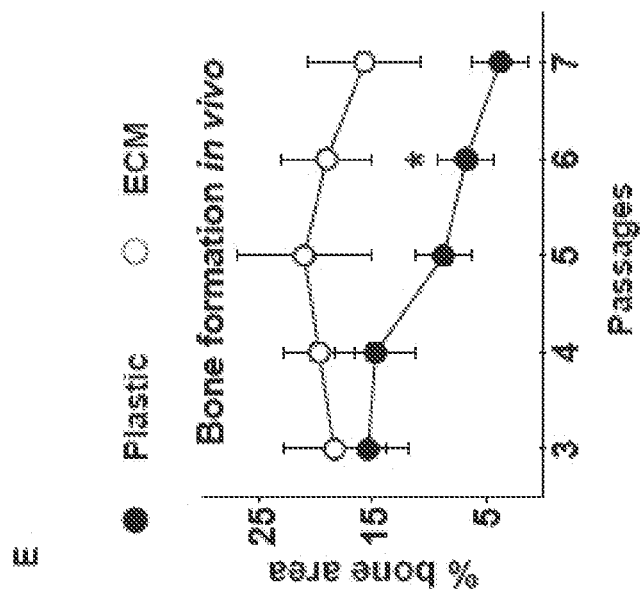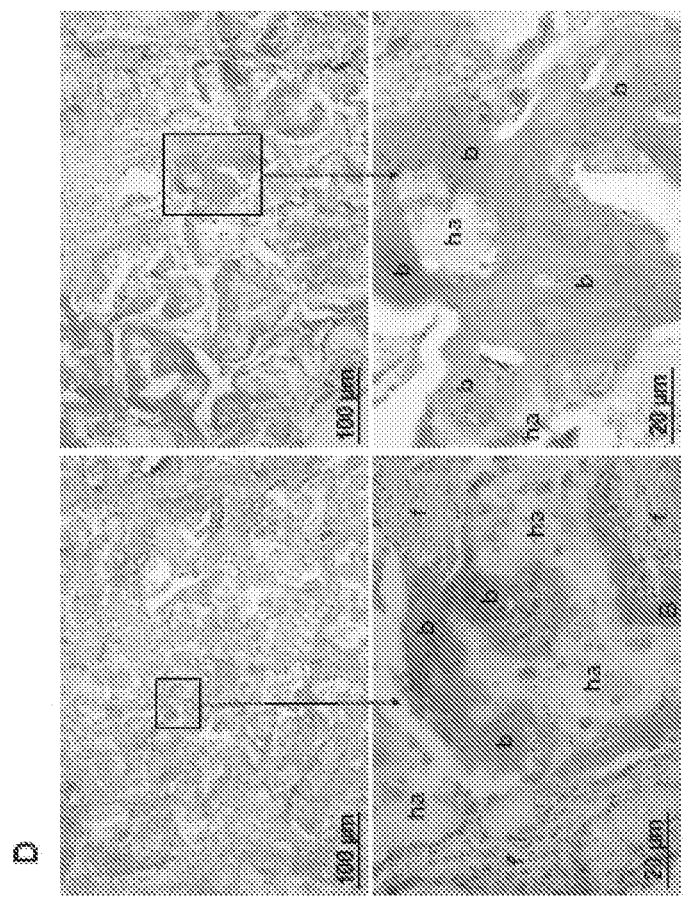
FIGS. 12D-E

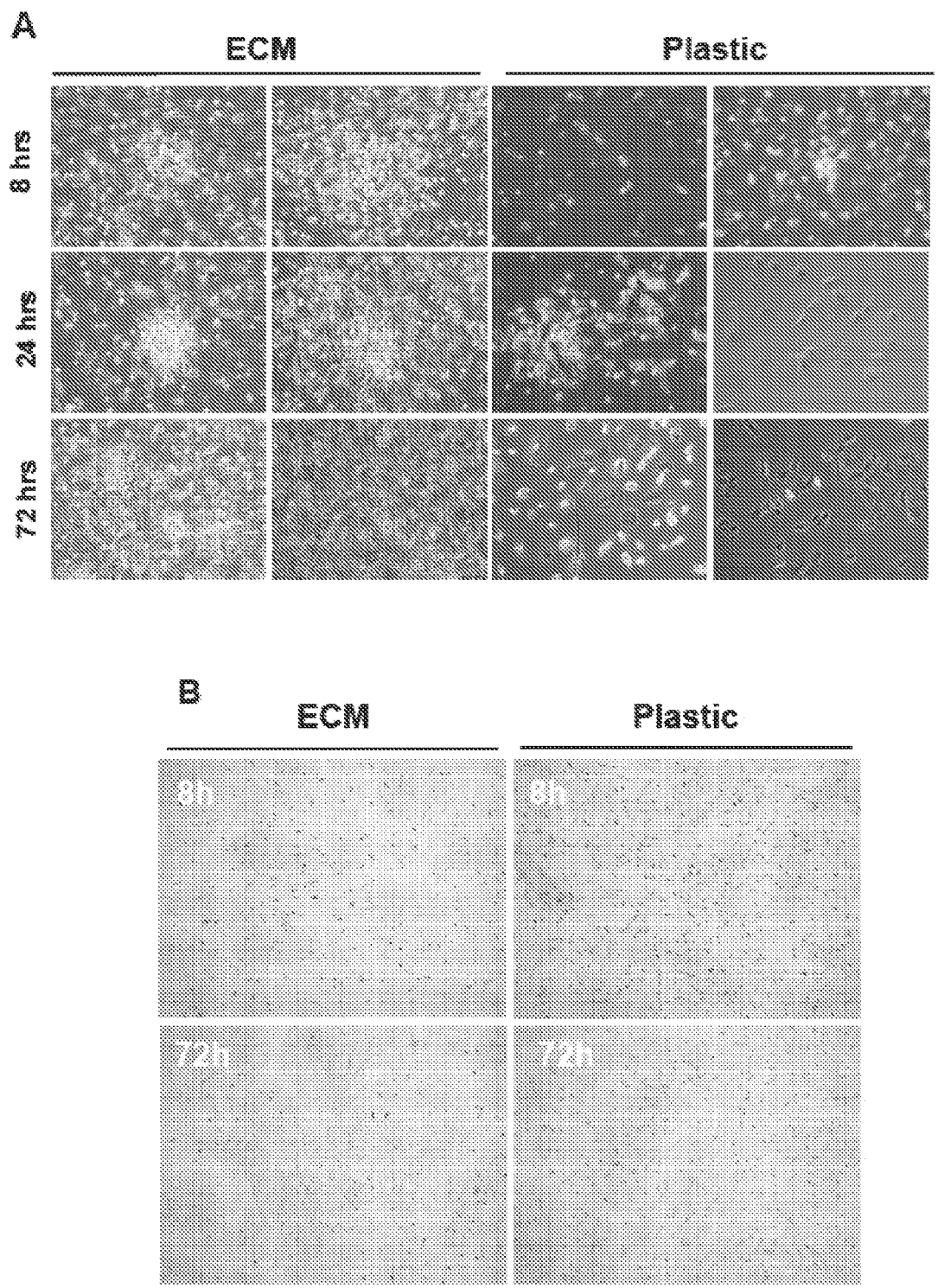
FIG. 16A-B

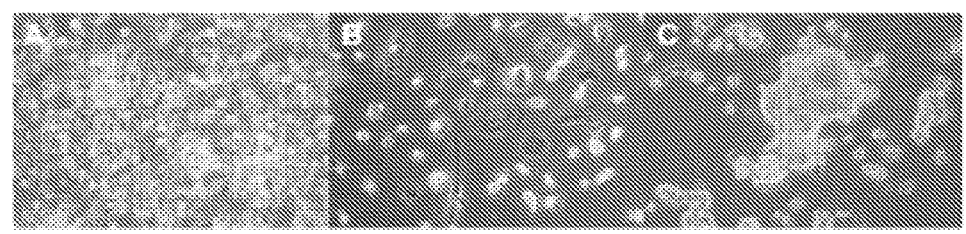
FIG. 17A-C
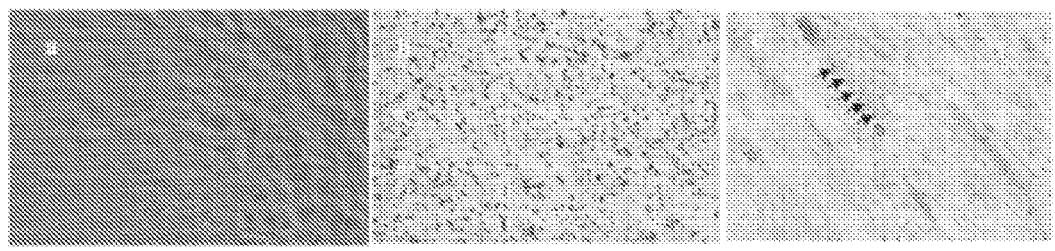
FIG. 18A-C

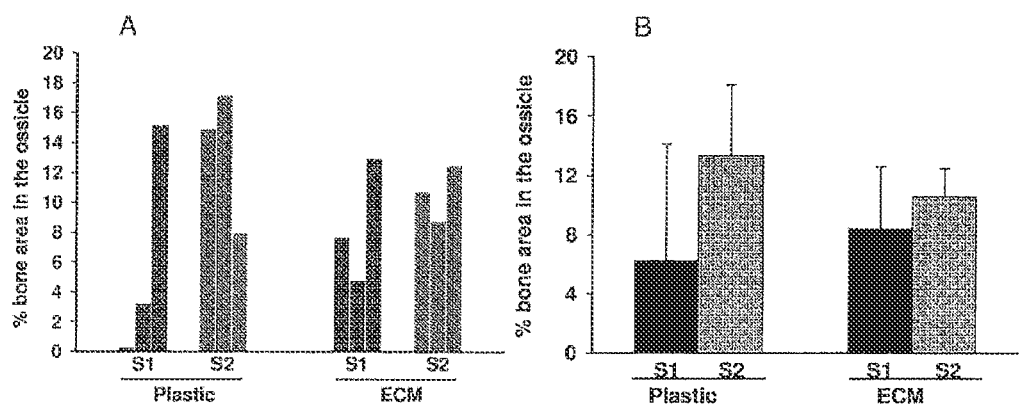
FIG. 36A-B

TISSUE-SPECIFIC DIFFERENTIATION MATRICES AND USES THEREOF

The present application is a national phase application under 35 U.S.C. 371 of International Application No. PCT/US2011/050550 filed Sep. 6, 2011, which claims benefit of priority to U.S. Provisional Application Ser. No. 61/380,691 filed Sep. 7, 2010 and U.S. Provisional Application No. 61/390,558 filed Oct. 6, 2010. The entire contents of each of the above-referenced disclosures are hereby incorporated by reference.

This invention was made with government support under 5R21AG25466-2, awarded by the National Institutes of Health. The government has certain rights in the invention.

BACKGROUND OF THE INVENTION

1. Field of the Invention

The present invention relates generally to the field of biology. More particularly, it relates to cell-derived extracellular matrices and uses of the same.

2. Description of the Related Art

Stem cells are one of the most fascinating areas of biomedicine today and hold great promise as a means to increase the healthy life-span of an aging worldwide population. The great promise of stem cells is due in large part to the tremendous plasticity and immaturity of human embryonic stem cells (hES cells) and the viral vector engineered cousins known as induced pluripotent stem cells (iPS cells). However, critical unsolved issues impair their therapeutic potential. For example, maintenance of hES cells requires the use of mouse embryonic feeder cells to inhibit their differentiation. This practice has the potential to cause mouse-to-human pathogen transfer referred to as "xeno-risk." Additionally, and aside from the controversial human embryo-source of hES cells, the phenomenal plasticity and self-renewal capability of natural ES cells and the uncertainties associated with the use of viral vectors for iPS cells may yield an under-appreciated disadvantage: the uncertain reliability and predictability of these cells in clinical applications, especially over the long-term.

As stem cells, mesenchymal stem cells (MSCs) are characterized by their ability to both self-renew and to differentiate into specific cell types in response to appropriate lineage-specific growth factors, for example, to differentiate into osteoblasts on stimulation with BMP-2. Examples of cell types that MSCs may differentiate into include, but are not limited to, osteoblasts, stromal cells that support hematopoiesis and osteoclastogenesis, chondrocytes, myocytes, adipocytes, neuronal cells, endothelial cells, and β-pancreatic islet cells (Prockop, 1997; Dennis et al., 1999; Ferrari et al., 1998). Moreover, MSCs are ideally suited for cell-based tissue engineering, for example, for the repair of skeletal tissue in nonunion fractures and reconstructive surgery (Muschler et al., 2004).

When MSCs divide, there are three possible fates (FIG. 13). Stem cells may divide asymmetrically to give a daughter stem cell and a more differentiated progeny, or symmetrically to give either two identical daughter stem cells or two more differentiated cells. As a result of these processes, MSCs produce new mature cells, such as osteoblasts, throughout life via orchestration of stem cell self renewal, together with the regulated expansion of early transit amplifying progenitors (uncommitted progenitors) and subsequent commitment to a particular lineage (Loeffler and Potten, 1997; Aubin and Triffitt, 2002). Regulation of these events allows preservation of stem cells, expansion of stem cells, and production of differentiated progeny when needed for tissue repair. Because of these capabilities, MSCs are involved in tissue regeneration throughout life. However, relatively little is known about the cellular and molecular mechanisms underlying the control of mesenchymal stem cell (MSC) proliferation, differentiation, and survival. This presents difficulties in following and characterizing cells along the lineage because of the inability to isolate and obtain a sufficient number of homogeneous MSCs using current culture systems for in vitro expansion.

MSCs are of great therapeutic potential due to their capacity of self-renewal and multilineage differentiation and have been proposed for treatment of degenerative diseases such as osteoarthritis and osteoporosis, of children with osteogenesis imperfecta (Horwitz et al., 2002; Kassem, 2006; Banerjee and Bhonde, 2007), for promoting healing of nonunion fractures (Petite et al., 2000), and for enhancing reconstitution of hematopoietic and immune systems after marrow ablation by chemotherapy or radiotherapy for treatment of leukemia and related diseases (Koc et al., 2000). However, lack of information on the factors that control MSC behavior has made implementation of such therapeutic strategies difficult.

Another major bottleneck in clinical application of MSCs has been their limited number, because they are rare in the primary tissue (approximately 0.001%) (Wexler et al., 2003). Earlier attempts to expand the MSCs ex vivo from rodent or human marrow have proven difficult. Adjusting the cellular machinery to allow greater proliferation can lead to other unwanted outcomes, such as unmanageable precancerous changes, or differentiation down an undesired pathway. Moreover, MSCs tend to lose their stem cell properties under traditional cell culture conditions. This situation has impaired the use of MSCs for practical purposes, such as therapeutic purposes.

When cultured on traditional tissue culture plastic systems, MSCs tend to lose their ability to self-renew and instead undergo senescence or "spontaneously" differentiate into osteoblastic cells, stromal cells, and adipocytes (DiGirolamo et al., 1999; Banfi et al., 2000; Baksh et al., 2004; Izadpanah et al., 2008; Kim et al., 2009). Furthermore, with extensive passaging, the stem cell population is likely diluted by the generation of more committed, transiently amplifying and differentiated cells and the MSCs often lose multilineage differentiation potential (Banfi et al., 2000; Baksh et al., 2004; Izadpanah et al., 2008; Kim et al., 2009). This suggests that the principal fate of MSCs is self-renewal without amplification and/or differentiation when cultured under these conditions, indicating that a critical factor(s) present in the marrow microenvironment responsible for the maintenance of MSC properties (stemness) is missing in such "standard" culture systems. In fact, loss of stem cell properties and "spontaneous" differentiation when MSCs are cultured on plastic may actually represent the response of MSCs to growth factors produced endogenously in these cultures. These problems have impaired efforts to expand MSCs in culture for the purpose of studying molecular mechanisms that govern self-renewal and differentiation and for investigating their potential therapeutic use (Baksh et al., 2004).

Several approaches have been used in an attempt to preserve the properties of MSCs. The use of surface markers or differential adhesion strategies to enrich MSCs prior to expansion on tissue culture plastic has not been successful. Cultures with specific growth factor cocktails, such as fibroblast growth factor and leukemia inhibitory factor, have generally failed because the growth factors inevitably favor a particular lineage and cause loss of self-renewal capacity and multipotentiality (Jiang et al., 2002; Bianchi et al., 2003; Sotiropoulou et al., 2006).

Other previous attempts to restrain "spontaneous" MSC differentiation have involved culture on fibronectin matrices under low oxygen tension (3-5%) (D'Ippolito et al., 2006) to mimic the microenvironment of the bone marrow (Chow et al., 2001) or cultures at low seeding density in low serum in the presence of growth factors (Sekiya et al., 2002; Peister et al., 2004). These conditions permitted expansion of mouse and human MSCs for as many as 60 population doublings, but the full differentiation potential and cellular composition of these cell preparations remain unclear. Particularly, the ability of such cell preparations to form skeletal tissue in vivo has not been reported. Although introduction of telomerase into stem cells (Gronthos et al., 2003) or four transcription factor genes (Oct4, Sox2, c-myc, and Klf4) into somatic cells to reprogram these cells to pluripotent stem cells has been successful (Takahashi et al., 2007; Yu et al., 2007), this procedure alters cell behavior via genetic modification, making these cells unpredictable for use in human therapy. Specifically, retroviruses used to trigger the reprogramming process can disrupt the normal function of DNA and the development of tumor formation (Okita et al., 2007). In addition, fibroblast growth factor (FGF)-2 has been reported to increase the size of human MSC colonies and to restrain their differentiation, but FGF-2 reduced colony number (Bianchi et al., 2003). Other investigators have reported that FGF-2 alters the properties of human MSCs and may even enhance osteoblastogenesis while reducing neurogenic capability (Sotiropoulou et al., 2006). It has also been reported that expansion of human and mouse MSCs is accompanied by cellular senescence and outgrowth of transformed cells, though transformation is less frequent in cultured human MSCs (DiGirolamo et al., 1999; Rubio et al., 2005; Miura et al., 2006; Rosland et al., 2009; Ksiazek, 2009).

Therefore, there remains a need for methods and compositions that provide for the maintenance, expansion, and use of stem cells.

SUMMARY OF THE INVENTION

In some aspects, this invention provides a method of making a series of tissue-specific extracellular matrices (ECMs) that are similar in the method of manufacture, but produce remarkably different results depending on the fibroblast-containing samples used to grow the ECMs, and the intended use thereof. In some aspects, this invention provides a method of making a bone marrow-derived tissue-specific stem cell proliferation, expansion, isolation and rejuvenation extracellular matrix (a "preservation matrix").

In some aspects, this invention provides a method of making a bone marrow-derived tissue-specific stem cell preservation matrix comprising a) obtaining a sample of bone marrow cells; b) culturing the bone marrow fibroblast cells along with the other cell types in the sample known to exist in bone marrow on a surface to produce an extracellular matrix; and c) removing the fibroblasts and other cells from the extracellular matrix to produce a cell-free extracellular matrix. In some embodiments, the fibroblast cell-free extracellular matrix may further be treated with DNase.

In other aspects, this invention provides a method of making a tissue-specific fibroblast-derived stem cell differentiation extracellular matrix (a "differentiation matrix"). In some aspects, this invention provides a tissue-specific differentiation matrix comprising an extracellular matrix generated by target tissue-specific fibroblast cells. In some embodiments, the differentiation matrix may be generated by cells obtained from a target tissue type to create a tissue-specific cell-derived extracellular matrix. In some aspects, this invention provides a series of tissue specific fibroblast-derived stem cell differentiation matrices generated by target tissue-specific fibroblast cells made by a method comprising a) culturing target tissue-specific fibroblast cells on a surface to produce an extracellular matrix; b) removing the fibroblast cells from the extracellular matrix to produce a fibroblast cell-free extracellular matrix. In some embodiments, the fibroblast cell-free extracellular matrix may further be treated with DNase. In some embodiments, the differentiation matrix is tissue-specific in that it correlates with the target cell type. For example, if adipocyte is the target cell type, then the tissue-specific differentiation matrix comprises an extracellular matrix generated by adipose cells. Similarly, if myocyte is the target cell type, then the tissue-specific differentiation matrix comprises an extracellular matrix generated by muscle tissue cells.

In any of the compositions and methods disclosed herein, the target cell type may be any cell type that is desired. Examples include, but are not limited to, neurons, epithelial cells and/or dermal cells, adipocytes, cardiomyocytes, renal cells, myocytes, hepatocytes, chondrocytes, islet cells, endothelial cells, dental pulp cells, and osteoblasts.

As discussed above, the tissue-specific extracellular matrix may also be referred to generically as a "cell-derived extracellular matrix." The fibroblast cells are cultured on a surface to produce an extracellular matrix. In some embodiments, the surface may be pre-coated with any appropriate substance, such as fibronectin or type I collagen. The fibroblast cells may be cultured for any appropriate length of time, such as 1, 2, 3, 4, 5, 6, 7, 8, 9, 10, 11, 12, 13, 14, 15, 16, 17, 18, 19, or 20 days or longer. In some embodiments, the fibroblast cells are cultured on the surface for 15 days. Additional substances may be added at any time during the culturing. In some embodiments, ascorbic acid is added. In some embodiments, the ascorbic acid is added during the final 8 days. The cells may be removed from the extracellular matrix by any appropriate method to produce the fibroblast cell-free extracellular matrix. In some embodiments, the cells are removed by incubating the extracellular matrix with Triton X-100 containing 20 nM $NH_4OH$ in PBS.

In any of the compositions and methods disclosed herein, the fibroblast cells that may be used to generate the cell-derived matrix may be isolated from any source. In some embodiments, the fibroblasts are from mammals, such as a human or murine subject. The fibroblast cells may be from any tissue-type. In some embodiments, the fibroblast cells are from neural tissue, skin (epidermal and/or dermal) tissue, adipose tissue, cardiac tissue, kidney tissue, muscle tissue, liver tissue, cartilage tissue, pancreas tissue, tissue of the endometrium of uterus, umbilical cord tissue, dental pulp tissue and trabecular and/or cortical bone tissue. Other sources of fibroblast cells may also be applicable.

In any of the compositions and methods disclosed herein, the cell-derived differentiation or preservation matrix may be a 3 dimensional (3D) extracellular matrix. As used herein, a 3D extracellular matrix is one that provides a 3D environment that completely surrounds cells once they are seeded onto the 3D extracellular matrix. Generally, a 3D cell-derived extracellular matrix is from 20 to 100 μM thick. Generally, feeder cells are necessary to prevent embryonic stems cells from differentiating. In some embodiments, the cell-derived differentiation or preservation matrix may be essentially free or entirely free of feeder cells. In some embodiments, the cell-derived differentiation or preservation matrix may be essentially free or entirely free of fibroblast cells. As used herein, the cell-derived differentiation or preservation matrix is "essentially free" of a substance when it contains at most trace amount of the substance, as sometimes the presence of a small amount of the said component is not avoidable e.g., due to impurities.

In some aspects, this invention provides a method of inducing tissue-specific differentiation of stem cells into a target cell type comprising contacting a sample of stem cells with a tissue-specific differentiation matrix that induces the stem cells to differentiate into the target cell type. As used herein, the term "stem cell" refers to a cell that gives rise to one or more lineages of cells, and thus may comprise multipotent or pluripotent stem cells. Stem cells may be obtained from any appropriate source; they may occur naturally, e.g., embryonic stem cells (ES cells) and mesenchymal stem cells (MSCs) from any of the many tissue and fluid sources in which they are known to exist, or they may be of an "engineered" variety; i.e., cells modified to regain an earlier, more naïve phenotype (e.g., induced pluripotent stem (IPS) cells).

In some embodiments, the method further comprises contacting the isolated stem cells with a second differentiation factor. The second differentiation factor may be any treatment that is known to cause a stem cell to be induced to commitment to a particular cell type. For example, in some embodiments, the target cell type is cardiomyocyte and the second differentiation factor may be bFGF and azacytidine. In other embodiments, the target cell type is osteoblast and the second differentiation factor may be BMP-2. In some embodiments, the stem cells may be obtained from any source, which may include purchase from a commercial source. In other embodiments, the isolated stem cells are MSCs, and are obtained by a method comprising a) contacting a MSC-containing sample with a preservation matrix comprising an extracellular matrix generated by bone marrow cells including bone marrow fibroblast cells and co-cultured with other cell types known to exist in the bone marrow; and b) isolating the MSCs from the preservation matrix.

In any of the compositions and methods disclosed herein, the MSC-containing sample may be from any appropriate source. Examples include, but are not limited to, bone marrow, periosteum, trabecular bone, adipose tissue, synovium, skeletal muscle, deciduous teeth, fetal pancreas, lung, liver, amniotic fluid, umbilical cord blood and umbilical cord tissues.

In some aspects, this invention provides a method of inducing tissue-specific differentiation of MSCs comprising isolating the MSCs from a MSC source using the preservation matrix, expanding the number of MSCs in serial fashion on one or more preservation matrices to obtain a sample of MSCs of sufficient quantity to produce the desired effect and then directly administering the isolated cells to a subject in need of such treatment. In a particular embodiment, the MSCs are administered by injecting the cells directly into the damaged tissue or the tissue in need of regeneration. Other stem cell types (e.g. ES cells, IPS cells and other stem cells known in the art) may be used in a similar manner, after having first been expanded on the preservation matrix to yield a stem cell sample of sufficient quantity to produce the desired effect, and then administered directly to a subject in need.

In some aspects, this invention provides a method of inducing tissue-specific differentiation of stem cells including but not limited to mesenchymal stem cells (MSCs), into a target cell type comprising contacting a fully-expanded sample of stem cells (i.e., a sample of sufficient quantity to produce the desired effect) with a tissue-specific differentiation matrix comprising an extracellular matrix generated by target fibroblast cells that induces the stem cells to differentiate into the target cell type. In some embodiments, the method further comprises contacting the isolated stem cells with a second differentiation factor.

In some aspects, this invention provides a method of repairing damaged tissue comprising a) contacting a sample of stem cells, including but not limited to MSCs, that is fully-expanded (i.e., comprises a sample of sufficient quantity to produce the desired effect) with a tissue-specific differentiation matrix comprising an extracellular matrix generated by target tissue-specific fibroblast cells; b) isolating the stem cells from the tissue-specific differentiation matrix; and c) injecting the isolated stem cells into a subject to produce tissue-specific differentiated stem cells. As discussed above, the target-tissue specific fibroblast cells may be from any appropriate source. In some embodiments, injection of the isolated stem cells into a subject causes differentiation of the isolated MSCs into the cell type that correlates with the source of the target-tissue specific fibroblast cells. In some embodiments, the target-tissue specific fibroblast cells may be from cardiac tissue. In such embodiments, injecting the isolated stem cells into the subject causes differentiation of the isolated stem cells into myocardiocytes. In some embodiments, the method is defined as a method of improving cardiac function after a myocardial infarction. In particular embodiments, the stem cells are umbilical cord blood-derived mesenchymal stem cells (UCB-MSCs).

In some aspects, this invention provides a method of treating a subject having a physiologic deficiency comprising a) contacting a sample containing MSCs with a rejuvenating matrix to produce a fully-expanded sample of rejuvenated MSCs (i.e., a sample of sufficient quantity to produce the desired effect); and b) introducing the rejuvenated MSCs into the subject, wherein the physiologic deficiency is treated. A "rejuvenating matrix" is a preservation matrix generated by fibroblast cells derived from a subject that is younger than the subject having a physiologic deficiency. The younger subject may be any amount younger than the subject having a physiologic deficiency. In some embodiments, the sample containing MSCs contains isolated MSCs. In some embodiments, the isolated MSCs are obtained by a method comprising a) contacting a MSC-containing sample with a preservation matrix; and b) isolating the MSCs from the preservation matrix. The physiologic deficiency may be any deficiency associated with the progressive failure of function of tissues and organs.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

The term "therapeutically effective" as used herein refers to an amount of cells and/or therapeutic composition (such as a therapeutic polynucleotide and/or therapeutic polypeptide) that is employed in methods of the present invention to achieve a therapeutic effect, such as wherein at least one symptom of a condition being treated is at least ameliorated.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIGS. 1A-B Characteristics of murine marrow cell-derived ECM. (FIG. 1A) SEM images of marrow cell-derived ECM before and after removing cells. Left panels show the ECM made by cultured marrow adherent cells before and after cell removal at low magnification. Right panels, at high magnification, show that the structure of the ECM is very similar before and after cell removal. (Inset) Enlargement of high-magnification image after cell removal. Left panel, original magnification, ×50, and middle panel, original magnification, ×200), and some of these generated embryonic bodies (right panel, original magnification, ×200). (FIG. 1B) Components of cell-free ECM made by cultured marrow cells were visualized by immunohistochemical staining before and after cell removal. The cells are stained blue-green. Original magnification, ×200.

FIGS. 2A-C Enhanced colony formation on the marrow cell-derived ECM. Freshly isolated bone marrow cells were seeded at 1 or $2 \times 10^6$ cells per 10-cm² well on plastic, a cell-free marrow cell-derived ECM, or tissue culture plastic coated with fibronectin or type I collagen, and the cultures were maintained as described for the determination of CFU number. (FIG. 2A) CFU-F in culture plates and at ×25 magnification, CFU-OB and CFU-AD at ×100 magnification. (FIG. 2B) The mean±SD number per well of CFU-F, -OB, and -AD was determined at indicated seeding densities in triplicate wells. *$p<0.05$ vs. plastic or the plates coated with fibronectin or type I collagen. (FIG. 2C) SEM images of bone marrow cells cultured on plastic or the ECM were obtained after 5 or 10 days of culture. Left panels show cells at the edge of a colony of fibroblastic cells. Middle panels represent enlarged images corresponding to the white squares in the left panels.

FIGS. 3A-D The marrow cell-derived ECM restrains "spontaneous" differentiation of MCFUs. Freshly isolated murine bone marrow cells were seeded at $3 \times 10^6$ cells per 10-cm² well on plastic or the marrow cell-derived ECM for up to 25 days. (FIG. 3A) Total RNA. (FIG. 3B) Appearance of cells cultured on plastic or the ECM observed by phase contrast microscopy after 20 days of culture. Original magnification: ×200. The arrow indicates nodules of cells. (FIG. 3C) Level of transcripts of osteoblastic cell markers. Number in parentheses indicates the fold change in transcript level from days 5 to 25. (FIG. 3D) Level of transcripts for BMP and Wnt antagonists. The data shown represent the mean±SD RNA level, or transcript level determined by TaqMan PCR, in triplicate cultures at the indicated time-points. *$p<0.05$ vs. plastic at the same time-point.

FIGS. 4A-D Enhanced BMP-2 responsiveness of MCFUs cultured on the marrow cell-derived ECM. (FIG. 4A) The level of BMP-2 transcripts was determined in the experiment described in FIG. 3. *$p<0.05$ vs. plastic at the same time-point. (FIG. 4B) BMP-2 protein in cell/matrix layer or culture supernatant was measured in triplicate cultures at day 15 of the experiment shown in FIG. 3. *$p<0.05$ vs. plastic. (FIG. 4C and FIG. 4D) Murine bone marrow cell cultures were established either on plastic or the marrow cell-derived ECM. After 15 days of culture, vehicle or human recombinant BMP-2 was added at the indicated concentrations (n=3 per treatment group). ALP activity and secreted osteocalcin (FIG. 4C) were determined in parallel cultures at 2 and 6 days, respectively, after addition of BMP-2. The level of transcripts for ALP and osteocalcin (FIG. 4D) was determined by TaqMan PCR after 6 days of culture. *$p<0.05$ vs. vehicle control.

FIGS. 5A-B The marrow cell-derived ECM promotes replication of MCFUs. Aliquots of freshly isolated murine bone marrow cells were used to determine the numbers of CFU-F, CFU-OB, and CFU-AD on plastic, and portions of the remaining cells were seeded at $7 \times 10^6$ cells per 10-cm² well on tissue culture plastic, type I collagen gel, or the stromal cell-derived ECM. After 6 days of culture, the cells were rinsed twice with PBS to remove nonadherent cells. The adherent cells were detached from the various substrata with collagenase, counted, and reseeded on plastic separately for determination of CFU-F, CFU-OB, and CFU-AD. See Table 1 for cell yields and calculation of CFU values. (FIG. 5A) The appearance of CFU-F and CFU-OB assayed at the indicated seeding density after 6 days of expansion on type I collagen gel (Collagen Gel), tissue culture plastic (Plastic), or the marrow cell-derived ECM (ECM). (FIG. 5B) The number of CFU-F, CFU-OB, and CFU-AD before (initial isolate) and after expansion. The calculation of the fold changes in the number of colonies after expansion is outlined in Table 1. Bars represent the mean±SD of triplicate determinations. *$p<0.05$ by ANOVA vs. type I collagen gel, plastic, and initial isolate, t$p<0.05$ by ANOVA vs. plastic and initial isolate, $p<0.05$ compared with initial isolate.

FIGS. 6A-F Increased skeletal tissue formation by MCFUs expanded on the marrow cell-derived ECM. Cells ($1 \times 10^6$) cultured on plastic or the marrow cell-derived ECM in the experiment shown in FIG. 5 were loaded onto HA/TCP and implanted subcutaneously into the dorsal surface of 10-wk-old immunodeficient beige mice. Transplants were harvested after 4 or 8 wk of transplantation and processed for histological analysis. (FIG. 6A-D) Sections from ossicles harvested at 8 wk stained with H&E to visualize bone (Rubio et al., 2005), fibrous tissue (F), HA/TCP carrier (HA), bone marrow containing adipocytes and hematopoietic elements (BM), and multinucleated osteoclasts (OC). (FIG. 6A) Bone tissue generated by cells precultured on plastic. (FIG. 6B) Bone tissue generated by cells precultured on the marrow cell-derived ECM. (FIG. 6C) High-power view of hematopoietic marrow in bone generated by cells precultured on the ECM. (FIG. 6D) The indicated area from B enlarged to show an osteoclast with multiple nuclei. (FIG. 6E) Mean±SD bone area in ossicles determined in three transplants harvested at 4 wk and in three transplants harvested at 8 wk. (FIG. 6F) Mean±SD area occupied by hematopoietic marrow determined in sections from ossicles obtained 8 wk after transplantation. *p<0.05 vs. bone marrow generated by cells precultured on the plastic.

FIGS. 7A-B Characteristics of Human Marrow Stromal Cell-derived ECM. (FIG. 7A) SEM images of stromal cell-derived ECM before and after cell removal. Left panels: low magnification; and right panels: high magnification. The structure of the ECM appeared to be similar before and after cell removal. The arrow denotes a cell. (FIG. 7B) Confocal fluorescence images showing localization of collagens types I and III, fibronectin, biglycan, decorin, perlecan and laminin in the ECM elaborated by human bone marrow stromal cells before and after cell removal. The distribution of cells was visualized with DAP1 staining (blue), and matrix proteins by immunofluorescence (green). Proteins were detected using antibodies against the indicated components and green fluoroscent-labeled secondary antibodies. Non-specific isotype IgG was used as a negative control (Neg. Control). Nuclear staining with DAP1 is shown in blue.

FIGS. 8A-C Stromal Cell-derived ECM Enhances Human MSCs in Colony Formation. (FIG. 8A) The appearance of CFU-F, CFU-AD and CFU-OB colonies generated on the various substrata. Freshly isolated human bone marrow mononuclear cells were placed into uncoated plastic (Plastic), or plastic coated with a cell-free ECM (ECM), fibronectin (Fn) or collagen type I (Col.1) at $3 \times 10^5$ cells per 10 cm$^2$ area. After 24 hrs of incubation, nonadherent cells were removed and cultures maintained in a-MEM containing 15% FBS. After 14 days of culture, CFU-F colonies were visualized with crystal violet staining. CFU-OB colonies were generated by cells cultured in osteoblast differentiation medium. After 25 days of culture, CFU-OB colonies were visualized with von Kossa staining. CFU-adipocytes (CFU-AD) colonies were formed by cells cultured in adipogenic medium. After 10 days of culture, CFU-AD colonies were visualized with Oil Red 0 staining. (FIG. 8B) Microscopic views of CFU-F, CFU-AD and CFU-OB colonies formed on plastic or on the ECM. Original magnification: ×100. (FIG. 8C) Quantification of average size and intensity per colony formed on the various substrata using the ImageJ program. Osteocalcin secretion in supernatant collected from CFU-OB was measured using a Metra Osteocalcin EIA kit (QUIDEL Corporation, San Diego, Calif., USA). P<0.05, n=3 vs. plastic or plastic coated with fibronectin (Fn), or collagen type 1 Col. 1). P<0.05, n=3 vs. plastic or plastic coated with Fn.

FIGS. 9A-B Stromal Cell-derived ECM Promotes Human MSC Proliferation and Suppresses Reactive Oxygen Species (ROS) Formation. (FIG. 9A) Flow cytometric analysis of SSEA-4 expression by human MSCs from passage 2. Single-cell suspensions derived from cultures on uncoated plastic (Plastic), a cell-free ECM (ECM), or fibronectin (Fn) or collagen type 1 (Col. 1) for the various days were analyzed by FACS. Cells stained with primary non-specific antibody (isotype, IgG) served as negative controls (gray-peaks). (FIG. 9B) SSEA-4 and ROS analysis. Other cell aliquots were used to determine cell number (left panel), the number of SSEA-4$^+$ cells (middle panel), and ROS content (right panel) expressed as arbitrary units (AU) of DCF fluorescence per $10^5$ cells. *P<0.05, n=3 vs. plastic, plastic coated with fibronectin (Fn) or collagen type 1 (Col. 1) at the same time point.

FIGS. 11A-B Global Gene Expression Patterns for Human MSCs Cultured on ECM Compared to Cells Cultured on Plastic. (FIG. 11A) Gene expression signatures of human MSCs maintained on plastic vs. ECM for 12 days. They are presented by hierarchical clustering of 1741 transcripts that were significantly up- or down-regulated by the ECM as compared to plastic. Color bar represents the range of expression levels indicated by log 2 scale. (FIG. 11B) Enrichment plot of the 721 up-regulated transcripts on the ECM. The majority of this gene set was overrepresented within a ranked list of genes expressed by undifferentiated BMSC, shown in red. NES was 1.76 [Actual ES divided by Mean (ESs against all permutations of the dataset)]; and a Family Wise-error Rate (FWER) p-value was 0.016, which estimates the probability that the normalized enrichment score represents a false positive finding.

FIGS. 12A-E Stromal Cell-derived ECM Promotes Replication of CFUs, and Retains the Ability of MSCs to Form Skeletal Tissue in Vivo. (FIG. 12A) Appearance of CFU-F, CFU-AD and CFU-OB assayed after 7 passages of expansion on plastic or ECM. (FIG. 12B) Cell replication. Upper panels: replication of colony-forming cells expanded on the ECM vs. plastic, expressed as fold changes in number of colonies with increasing passage number. The replicative activity of MSCs maintained on the ECM was significantly higher (P<0.05) than those of MSCs maintained on plastic at all time-points. Lower panels: growth kinetics of colony forming cells (log scale) expanded on ECM vs. plastic with increasing passage number. *P<0.05, value at the earliest passage when cells expanded on ECM showed increased colony forming activity vs. plastic. (FIG. 12C) Telomerase activity in cells expanded on ECM vs. plastic with increasing passage number. *P<0.05 (by ANOVA), ECM vs. plastic (before P8). (FIG. 12D) Histology of ossicle produced by implantation of P7 human bone marrow cells. While bone was formed by cells expanded on plastic (left panels), as well as by cells expanded on ECM (right panels); high magnification (lower panels) of areas selected in upper panels clearly showed more robust bone formation in the latter. b, bone; f, fibrous tissue; and ha, HATTCP. (FIG. 12E) Following each passage, the cells ($1 \times 10^6$) were loaded into HA/TCP ceramic powder and transplanted subcutaneously into the dorsal surface of 10-week-old immunodeficient mice. Three implants for each group were harvested at 8 weeks post-implantation. The extent of new bone formed in the implants was histomorphometrically determined as areas measured by using the ImageJ analysis software. N=3; *P<0.05, value at the earliest passage vs. that at the passage 3 or 4.

FIGS. 16A-B (FIG. 16A) The ECM facilitates UCB-derived MSCs attachment and expansion. Human UCB was purchased from Texas Cord Blood Bank (San Antonio, Tex.). Mononuclear cells (MNCs) isolated from UCB using the Ficoll-Paque Premium density solution were seeded onto the ECM or uncoated plastic at $1\times10^6$ MNCs/cm$^2$ and cultured for 30 or 7 days (Day 3 or Day 7, respectively). Then, non-adherent cells were removed by washing with PBS. Original magnification, ×100. (FIG. 16B) Non-adherent cells were collected from uncoated plastic (Plastic) and the ECM 8 hrs and 72 hrs after primary seeding, and reseeded onto ECM plates at $1\times10^6$ MNC/CM$^2$. After 24 hrs of incaution, non-adherent cells were removed by washing with PBS. The adherent cells were stained with crystal violet (original magnification, ×50). 24 h after reseeding, non-adherent cells from the primary 2D plate showed 5 times more cells attached (Left panels, upper and lower; crystal violet stain) than from the primary ECM plate (Right panels, upper and lower).

FIGS. 17A-C (FIG. 17A) Colony formation. UCB-MSCs were seeded onto the ECM (FIG. 17A) or uncoated plastic (FIG. 17B) at $1\times10^6$ MNC/cm$^2$ and incubated for 72 hours at 37° C. (original magnification, ×100). (FIG. 17C) Embryonic-like bodies formed on ECM coated plates (original magnification, ×200).

FIGS. 18A-C Cell Differentiation. (FIG. 18A) Undifferentiated UCB-MSCs. (FIG. 18B) UCB-MSC adipogenesis, oil red stain showed the lipid droplets. (FIG. 18C) UCB-MSC myogenesis, hematoxtylin staining showed myotube with multiple nuclei (arrows).

(FIG. 20A) shows the slides for muscle, adipose tissue, and gland; (FIG. 20B) shows the slides for blood vessel, nerve fibers, and bone.

(FIG. 22A) The appearance of CFU-OB assayed before (Initial isolate) and after 7 days of culture on plastic, on the young-ECM, or the old-ECM. (FIG. 22B) The frequency (numbers of CFU-OB per $10^6$ cells) (Initial isolate) and after culture. (FIG. 22C) The replication of MSCs cultured on the various substrata. The replication is represented by fold change in CFU-OB during expansion. See Table 6 for cell yields and calculation of CFU values. (FIG. 22D) Comparison of ROS activity between young and aged MSCs before (initial isolate) and after 7 days of culture on tissue culture plastic or the ECMs. The intracellular level of ROS was quantified using dichlorodihydrofluorescein diacetate (H2DCFDA) (described in Methods). ROS levels were expressed as arbitrary units (AU) of DCF fluorescence per $10^5$ cells. *p<0.05 vs. 3M on Plastic; and †p<0.05 vs. 3M or 18M on Plastic and on O-ECM, respectively.

(FIG. 24A) Intracellular telomerase activity was measured using the quantitative telomerase detection kit (Allied Biotech, Inc., Twinsburg, Ohio, USA) according to manufacturer's instructions. Experiments were performed in triplicate, and telomerase levels were expressed as amoles per $10^6$ cells. †p<0.05 vs. 3M or 18M on Plastic and on Old-ECM, respectively. (FIG. 23B) Intracellular ATP levels were measured according to the manufacturer's instructions (HemoGenix, Inc., Colorado Springs, Colo., USA). Experiments were performed in triplicate, and ATP levels were expressed as μmoles per $10^6$ cells. *p<0.05 vs. 3M on Plastic or O-ECM; and †p<0.05 vs. 18M on Plastic and on O-ECM, respectively.

FIGS. 24A-B Increased skeletal tissue formation by MSCs, from either young (3M) or old (18M) mice, cultured on young-ECM. Cells ($1 \times 10^6$) pre-cultured on plastic or young-ECM for 7 days were loaded onto Gelfoam and implanted subcutaneously into the dorsal surface of 10-week-old immunodeficient mice. Implants were harvested 8 weeks following transplantation. Bone content was determined by MicroCT (μCT) and histological analysis. (FIG. 24A) Experiment 1. Left panels show μCT images from the middle section of implants, and skeletal tissue is indicated by white color. The quantification is shown in Table 8. Right panels show histological analysis of sections from ossicles stained with H&E to visualize bone. (FIG. 24B) Experiment 2. μCT images (high resolution) show the whole implants. The quantification is shown in the right panel. *p<0.05.

(FIG. 27A) Comparison of ROS levels between Tg(Gpx4)$^{+/0}$ mice and wt littermates. Bone marrow cells were harvested from femora obtained from 3-month old female Tg(Gpx4)$^{+/0}$ mice and wt mice. Intracellular levels of ROS in these cells were quantified using dichlorodihydrofluorescein diacetate (H2DCFDA) (described in Example 5). ROS levels were expressed as arbitrary units (AU) of DCF fluorescence per 105 cells. *p<0.05 vs. wt. (FIG. 27B) The appearance of CFU-OB assayed after 7 days of culture on plastic. CFU-OB was determined by Von Kossa stain, which appears dark. (FIG. 27C) Comparison of MSC replication between Tg(Gpx4)$^{+/0}$ mice and wt littermates. In the same experiments, the replication of CFU-OB was determined by measuring the numbers of CFU-OB before ("initial isolate") and after expansion, as previously described in FIG. 26. *p<0.05. (FIG. 27D) Increased skeletal tissue formation in vivo by MSCs from Tg(Gpx4)$^{+/0}$ mice compared to wt littermates. Freshly isolated marrow cells from either Tg(Gpx4)$^{+/0}$ mice or wt littermates were seeded at $7 \times 10^6$ cells per 10 cm$^2$ well onto tissue culture plastic and cultured for 7 days. The cultured adherent cells ($1 \times 10^6$) were loading onto Gelfoam and implanted subcutaneously into the dorsal surface of immunodeficient mice. Implants were harvested 8 weeks following transplantation. BMD in ossicles was determined by μCT analysis. *p<0.05, n=6 vs. wt littermates.

(FIG. 28A) After 1 month of culture, CFU-Fs were fixed and stained with crystal violet (original magnification, ×50). Also CFU-Fs are shown in culture, some of which appeared to generate embryonic bodies (EB) (original magnification, ×200). (FIG. 28B) CFU-OB colony formation in triplacte wells. CFU-F colonies were mainted for an additional 25 days in an osteoblast differentiation medium, as described in the Methods section. The CFU-OB colonies were detected by von Kossa staining or mineral (shown in dark). SD: cell seeding density.

(FIG. 29A) Morphological characteristics of the differentiated cardiomyocytes (original magnification, ×200). Beating cells are indicated by white circles. (FIG. 29B) The transcripts of α-myocin heavy chain (βMHC) and cardiac troponin T (TropT) were quantified by TaqMan PCR on day 25 of culture in a growth or the differentiation medium. As a positive control<RNA from total adult mouse cardiac tissue was used. *P<0.05 (n=5), vs. Mouse heart, or UCB-MSCs/Unt.

FIGS. 36A-C illustrate quantification of bone in ossicles. Each ossicle was bisected. Then, three 10 μm sections were cut from the center part at 100 μm intervals. (FIG. 36A) the measurements of bone area from 3 individual sections for each sample (S1 or S2). (FIG. 36B) the mean bone area calculated from 3 individual sections for each sample (S1 or S2). (FIG. 36C) quantification of bone marrow in ossicles with mean bone marrow (hematopoietic tissue) calculated from 3 individual sections for each sample.

DESCRIPTION OF THE ILLUSTRATIVE EMBODIMENTS

A. Stem Cells (SCs)

Figure 7B:
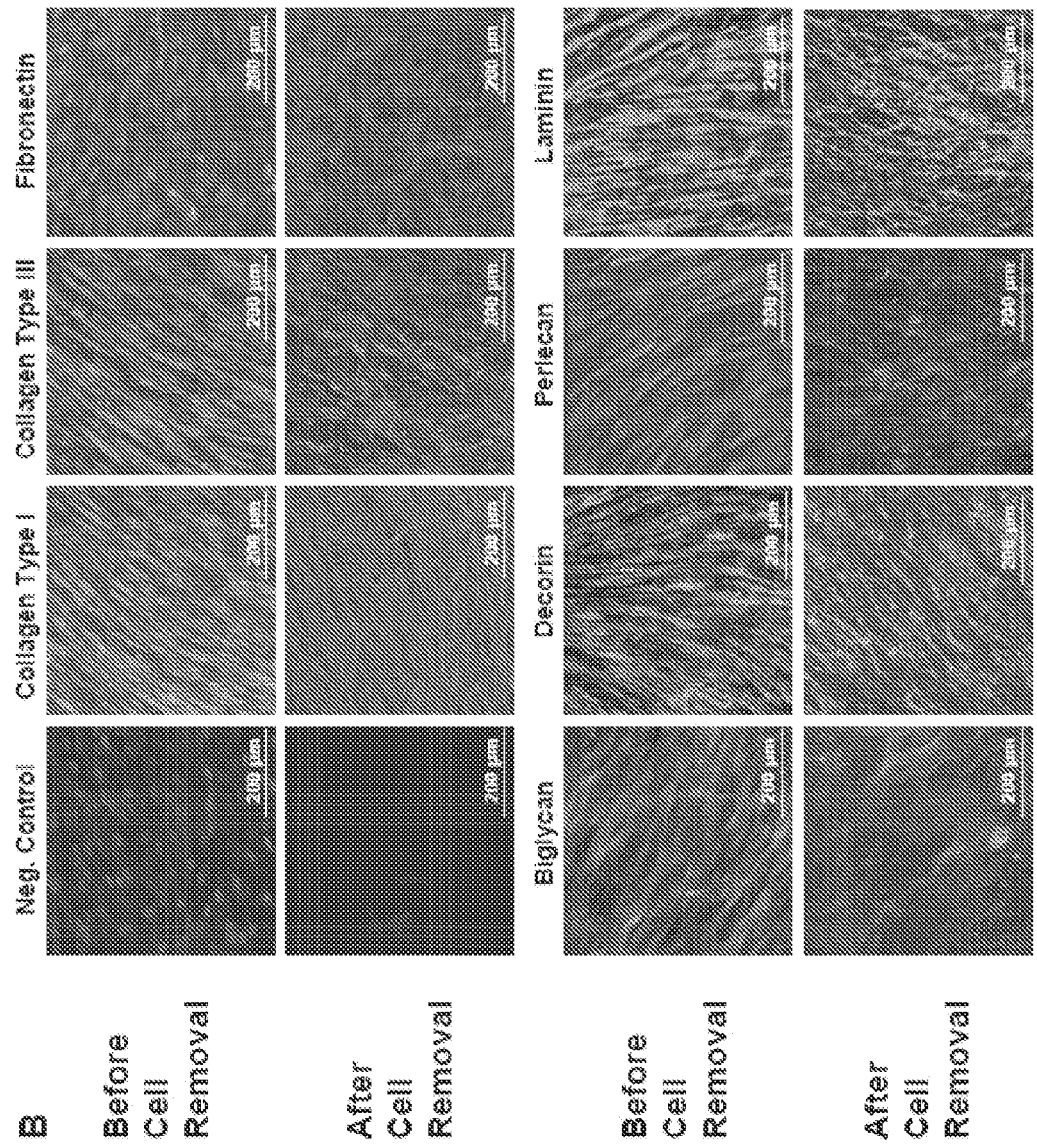

The term "stem cell" as used herein refers to a cell that gives rise to one or more lineages of cells, and thus may comprise multipotent or pluripotent cells. Stem cells may be obtained from any appropriate source; they may occur naturally, such as embryonic stem cells (ES cells) and mesenchymal stem cells (MSCs), or they may be of an engineered variety, i.e., cells modified to regain an earlier phenotype, such as induced pluripotent stem (IPS) cells. Mesenchymal stem cells (MSCs) mainly reside within the bone marrow, which consists of stromal cells, adipocytes, vascular elements, and sympathetic nerve cells arrayed within a complex extracellular matrix (ECM). However, it has been reported that MSCs could be isolated from various tissues, including periosteum, trabecular bone, adipose tissue, synovium, skeletal muscle, deciduous teeth, fetal pancreas, lung, liver, amniotic fluid, umbilical cord blood and umbilical cord tissues.

Stem cells can be viewed conceptually as residing on a continuum. On one extreme are hES cells, which can provide any or many types of cells simultaneously, but may or may not reliably and predictably produce the one cell type needed for a specific application. On the other end are adult mesenchymal stem cells, which are able to produce more reliable and predictable terminal cells, but do not offer the flexibility of hES cells. In order for stem cell therapies to become a clinical reality, these therapies must employ stem cells with sufficient plasticity to provide the desired cell lineage and the ability to do so predictably and reliably. Lastly, the materials and methods associated with their use must be practical enough to ensure widespread use. This invention provides for methods and materials useful for the manufacture and use of cell-derived preservation or differentiation matrices to induce reliable and predictable tissue-specific differentiation of pluripotent stem cells including but not limited to hES cells, iPS cells and mesenchymal stem cells (MSCs).

B. The Extracellular Matrix

Besides its obvious roles in determining the architecture and mechanical properties of tissues, the ECM greatly influences cell adhesion, migration, proliferation, differentiation, and survival (Gospodarowicz, 1984; Lukashev and Werb, 1998; Cukierman et al., 2001; Abbott, 2003). ECM modulates the bioactivities of growth factors and cytokines, such as transforming growth factor-β (TGF-β), tumor necrosis factor-α, and platelet-derived growth factor, by activating latent growth factors via proteolytic processing (Gleizes et al., 1997; Tufvesson and Westergren-Thorsson, 2002; Nili et al., 2003), by sequestering growth factors and hindering them from binding to their receptors or by directly affecting receptor activity (Hildebrand et al., 1994; Santra et al., 2002). Cells residing in the ECM not only receive ECM cues but also influence ECM signaling by secreting ECM components and by producing enzymes that cause proteolytic modification of proteins and growth factors in the ECM. The end result is a "give and take" relationship between cells and the ECM that defines cell behavior (Behonick and Werb, 2003).

Regardless of tissue types, the ECM consists of collagen fibers, laminin polymers, cell adhesion proteins such as fibronectin, high molecular-weight proteoglycans, various growth factors that often exist in a latent or masked form, and members of the small leucine-rich proteoglycan (SLRP) family, mainly biglycan (bgn) and decorin (dcn) (Clark and Keating, 1995; Hocking et al., 1998; Lee et al., 1999). As might be expected from such a complex composition, the structure of the ECM in most tissues is not well understood. However, based on the studies of kidney basal lamina and ECM of skin, it is generally accepted that the ECM structure is dictated by the interaction of collagen fibers with each other and with laminin, as well as high-molecular-weight proteoglycans, resulting in the formation of an interlocking mesh-like structure (Pollard and Earnshaw, 2002). SLRPs such as bgn and dcn are also associated with collagen fibers and also with fibronectin and growth factors in the ECM. SLRPs appear to be important for collagen fibrillogenesis, as well as growth factor localization.

The loss of sternness during growth of MSCs using current culture methods reflects the production of more differentiated progeny with diminished self-renewal capacity, rather than the production of identical daughter stem cells. The term "stemness" refers to the stem cell properties including self-renewal (proliferation) and multipotentiality (capacity for the differentiation into multiple cell lineages). Involvement of the ECM in the regulation of mesenchymal colony forming units (MCFUs) is further supported by evidence that deletion of the ECM components biglycan and decorin has a deleterious effect on responsiveness of marrow derived osteoblast progenitors to BMPs and TGF-β (Di Gregorio et al., 2001; Chen et al., 2004). At this stage, it is unknown how the ECM regulates the behavior of MCFUs. Earlier work has shown that the ECM modulates the activity of growth factors by controlling proteolytic activation of latent factors, as occurs in the case of TGF-β (Dallas et al. 2002). The ECM also interacts with cell surface receptors to prevent binding of the cognate ligand, as occurs in the case of the epidermal growth factor (EGF) receptor (Santra et al., 2002), and sequesters factors such as platelet-derived growth factor (PDGF) and BMPs (Suzawa et al., 1999; Nili et al., 2003). The ECM may also bind growth-promoting factors from the serum for optimal presentation to MSCs. Finally, the ECM may enhance the function of putative accessory cells that support MCFU replication.

C. Study of MSCs

1. Two Dimensional Tissue Culture Plastic

Because of its simplicity, two dimensional (2D) tissue culture plastic has been widely used to investigate the cell and molecular biology of connective tissue cells, including osteoblasts. 2D ex vivo cultures of MSCs will eventually elaborate a 3D ECM that resembles that of the bone marrow (Friedenstein et al., 1974; Clark and Keating, 1995) or the bone matrix (Bennett et al., 2001), when cultured under conditions that favor stromal cell differentiation or osteoblast differentiation, respectively. Primary calvaria-derived and certain osteoblastic lines can also elaborate 3D bone-like matrix.

However, it has become increasingly evident that classical 2D culture systems are inadequate for studying the behavior of cells (Abbott, 2003). First, the critical initial events that characterize the give and take relationships between MSCs and the ECM cannot be studied in such cultures because the ECM is not present in the early stages. Second, studies have shown that connective tissue cells behave very differently in 3D as opposed to 2D cultures, raising the possibility that the latter system can give misleading results (Cukierman et al., 2001). For example, culture of fibroblasts on flat substrates induces a polarity that does not occur in vivo. Moreover, when fibroblasts and other cell types are cultured in 3D tissue-derived matrices, they develop mature integrin-containing focal adhesion complexes within minutes that resemble the complexes found in vivo, whereas only primitive adhesion complexes develop in 2D cultures or even simple 3D type I collagen gels or Matrigel. These adhesion complexes are required for appropriate growth factor-activated receptor signaling and rapid (5 min) initiation of synthesis of their own ECM components and factors that alter the ECM (Cukierman et al., 2001; Abbott, 2003). Third, cells in ECM culture deposit autocrine growth factors into tissue-derived matrices, a process that may be required for appropriate presentation of the growth factor to target cells. On the other hand, such factors are mainly secreted into the culture medium in 2D cultures. Previous attempts to generate 3D matrices focused on collagen type I gels or Matrigel made from basement membranes mainly containing laminin, collagen IV, and heparan sulfate proteoglycans. However, these gels lack critical components found in marrow ECM.

Studies of other cell types have used purified collagens and adhesive proteins such as fibronectin, artificial matrices comprising synthetic polymers such as poly(L-lactide-co-glycolide), poly(ethylene terephthalate), complex mixtures of proteins extracted from tissues such as Matrigel (which contains matrix proteins from basement membrane), and cell-free matrices made by cultured cells (Cukierman et al., 2001; Grayson et al., 2004; Jarrahy et al., 2005; Mao and Schwarzbauer, 2005; Philp et al., 2005; Chen et al., 2007).

It is almost certain that culture of marrow-derived MSCs on standard 2D tissue culture plastic surfaces results in changes in their behavior that never occur when grown in their native matrix.

2. Cell-Derived Extracellular Matricies a. A Cell-Derived Stem Cell Proliferation, Expansion, Isolation and Rejuvenation ECM (the "Preservation Matrix")

The difficulty in long-term expansion of MSCs using standard culture systems without the loss of their stem cell properties suggests that a critical feature of their microenvironment necessary for retention of stem cell properties is absent in these culture systems. As the ECM is an important component of the cellular niche in a tissue, supplying critical biochemical and physical signals to initiate or sustain cellular functions, it is possible that the ECM is required for the reconstitution of the niche in vitro (which is ignored in tissue culture plastic systems) to efficiently retain stem cell properties.

In some aspects, this invention provides a method of making a bone marrow-derived tissue-specific stem cell preservation matrix comprising a) obtaining a sample of bone marrow cells; b) culturing the bone marrow fibroblast cells along with the other cell types in the sample known to exist in bone marrow on a surface to produce an extracellular matrix; and c) removing the fibroblasts and other cells from the extracellular matrix to produce a cell-free extracellular matrix. In some embodiments, the cell-free extracellular matrix may further be treated with DNase.

Figure 15:
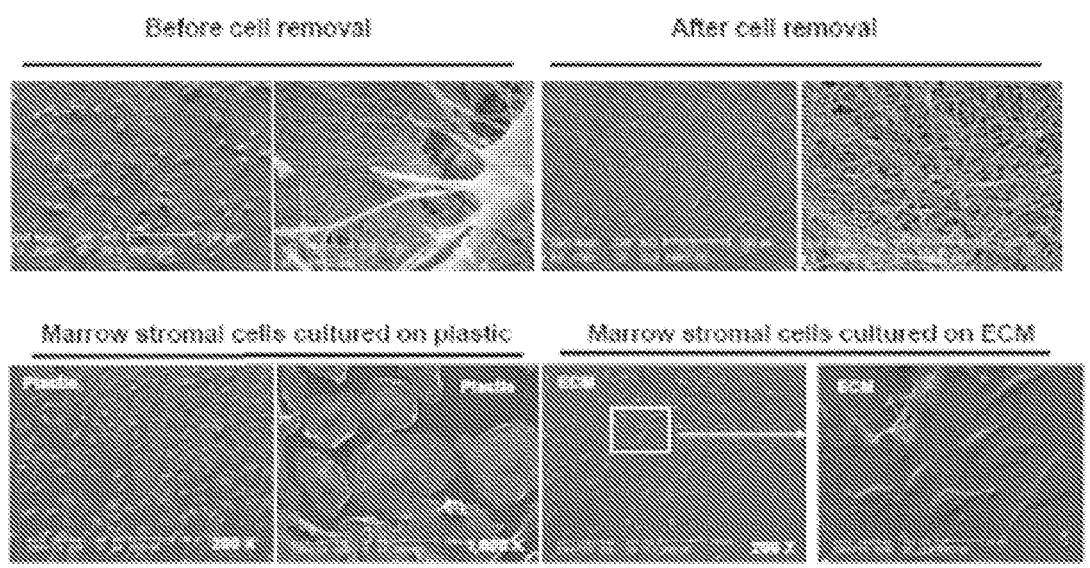
FIG. 15 Reconstitution of a native, cell-free ECM ex vivo for the maintenance of MSCs. The top panel shows SEM images of mouse stromal cell-derived ECM before and after removing cells, and the lower panel shows SEM images of mouse bone marrow cells grown on plastic or the ECM after 5 days of culture.

The inventor has reconstituted, for both human and mouse MSCs, a native cell-free preservation ECM generated by bone marrow cells ex vivo to simulate the marrow environment where MSCs are found in vivo (FIG. 15). The inventor has found the preservation ECM to be useful not only for the preservation of stem cell "stemness" when the cells are maintained on the preservation ECM, but also as a surprisingly effective method for the identification of large numbers of quite naïve planktonic stem cells in umbilical cord blood, and also surprisingly effective at rejuvenating a "younger MSC phenotype" in MSCs isolated from an older subject. In some embodiments, the present invention provides a stem cell proliferation, expansion, isolation and rejuvenation extracellular matrix, also called a "stem cell preservation ECM" or simply a "preservation ECM" that is generated by bone marrow cells. The bone marrow cells may be mammalian, for example human or mouse. The bone marrow cells may be from any appropriate bone marrow source, and may be from any desired subjects of any age.

The source of the structural components of the preservation ECM may be contributed by bone marrow stromal cells, adherent cells, or other sources of MSCs. It is possible that these cells with other accessory cells such as hematopoietic mononuclear cells together influence properties of the preservation ECM by secreting growth factors, cytokines, and matrix metalloproteinases that affect the biosynthetic activity of the stromal cells. Such bone marrow derived preservation ECM is approximately 20- to 100-μm thick, consists of at least collagen types I and III, fibronectin, small leucine-rich proteoglycans such as biglycan and decorin, and major components of basement membrane such as the large molecular weight proteoglycan perlecan and laminin.

Expansion of human MSCs on this cell-derived preservation ECM strongly promoted their proliferation, retained their stem cell properties with a low level of reactive oxygen species (ROS), and substantially increased their response to BMP-2. The quality of the expanded cells following each passage was further tested by an in vivo transplantation assay. The results showed that MSCs expanded on the cell-derived preservation ECM for multiple passages still retained the same capacity for skeletogenesis. In contrast, the bone formation capacity of cells expanded on plastic was dramatically diminished after 6-7 passages. These findings suggest that the marrow stromal cell-derived preservation ECM is a promising matrix for expanding large-scale highly functional MSCs for eventual use in stem cell-based therapy. Moreover, this system should also be invaluable for establishment of a unique tissue-specific cell-derived preservation ECM, which will facilitate control of the fate of MSCs for therapeutic applications.

Culture of marrow-derived MSCs on a cell-free cell-derived preservation ECM made by marrow-derived stromal cells promotes self-renewal of MSCs and helps maintain the MSCs in an undifferentiated state. Following expansion on this cell-derived preservation ECM, functional MSCs were increased as evidenced by increased formation of bone and hematopoietic marrow tissue following subcutaneous transplantation of in vitro expanded MSCs to immuno-compromised mice. The cell-derived preservation ECM described herein provides a system for the expansion of functional MSCs for practical applications. Culture of MSCs in the presence of three-dimensional (3D) stromal cell derived preservation ECM allows for attachment, self-renewal, and retention of multipotentiality of MSCs, whereas culture of MSCs under two-dimensional (2D) conditions with or without certain ECM proteins like type I collagen or fibronectin does not.

Culture of MSCs on a preservation ECM made by marrow-derived stromal cells promotes symmetric division to produce identical daughter cells whereas plastic favors production of differentiated progeny by symmetric or asymmetric cell division. Moreover, the MSCs expanded on the marrow cell-derived preservation ECM retain the ability to form a complete bone like structure comprising a calcified matrix made by osteoblasts, hematopoietic marrow containing adipocytes, and stromal cells that support hematopoiesis and osteoclastogenesis. In contrast, growth of MSCs on tissue culture plastic results in eventual loss of self-renewal capacity and multipotentiality, and this is associated with expression of the osteoblast phenotype. Although cells expanded on plastic did form bone in vivo, they made less bone and minimal hematopoietic marrow.

Surprisingly, bone marrow cells cultured on the cell-derived preservation ECM were completely embedded within the matrices after just 5 days of culture, and they exhibited a fibroblastic morphology with extensive cellular processes, whereas the same cells maintained on uncoated plastic are round and flat (FIG. 15). The cell-derived preservation ECM provides a 3D environment for cell growth.

MSCs cultured on this cell-derived preservation ECM show remarkable promotion of proliferation and retention of a stem cell population with a lower level of reactive oxygen species (ROS) when compared with those cultured on uncoated plastic or other 2D substrata (Lai et al., 2010). Interestingly, in hematopoietic stem cells, it has been reported that a high level of ROS is associated with the loss of stem cell characteristics and increased differentiation, as well as apoptosis (Tothova et al., 2007). Hence, the ability of the cell-derived preservation ECM to suppress ROS may contribute to the retention of MSC characteristics. Because MSCs are specific targets of BMP-2, which acts to induce MSC osteogenic differentiation, "true" MSCs should also respond to BMP-2 stimulation. Indeed, the data indicates that the sensitivity of MSCs to BMP-2 stimulation is dramatically increased upon maintenance on cell-derived preservation ECM when compared with plastic. The differential sensitivity may be related to the different cell composition when cells are maintained on cell-derived preservation ECM versus plastic. MSCs defined by stage-specific embryonic antigen (SSEA-4) cells grown on cell-derived preservation ECM or uncoated plastic retained approximately 80% or 24% of the positive cells at 14 days of culture, respectively. SSEA-4 was originally identified as an early embryonic glycolipid antigen (Kannagi et al., 1983), which can be used to identify human MSCs from bone marrow (Gang et al., 2007). Efficient stimulation of MSCs with a low dose of growth factors may more closely resemble the physiological situation, suggesting that cell-derived preservation ECM provides an optimal "home" for MSCs to retain their stem cell properties.

The maintenance of the undifferentiated status when cells are grown on the cell-derived preservation ECM has been further confirmed by the analysis of global gene expression profiles. The inventor identified 1741 transcripts that were significantly either up regulated or downregulated in cells cultured on the cell-derived preservation ECM versus on plastic, and 721 upregulated transcripts were shown to represent genes related to undifferentiated human MSCs when compared with human MSCs treated with BMP-2 (FIG. 11B). This finding strongly suggests that the genes expressed by cells maintained on the cell-derived preservation ECM are most likely the undifferentiated MSC gene set when compared with differentiated MSCs induced by BMP-2 treatment. The 1741 transcripts were further classified based on their biological function using the Gene Ontology database. Strikingly, based on the lowest p-value, the top three clusters mapped by these 1741 genes were associated with cell division (cell cycle) and cell motility (cytoskeleton; Table 1). In the cell cycle group, the inventor found that the transcription factors, c-myc, Klf4, and Sox2, originally identified in embryonic stem cells involved in retaining pluripotentiality, were upregulated when cells were maintained on the cell-derived preservation ECM when compared with cells maintained on plastic. The sets of genes highly related to cytoskeleton and microtubule-based cell motility support the observation that cell-derived preservation ECM promotes MSC attachment and motility. Interestingly, MSCs grown on the cell-derived preservation ECM underwent directional migration along the orientation of the cell-derived preservation ECM fibers with a decreased frequency of cell-cell contact, whereas MSCs grown on plastic showed random migration (unpublished results).

TABLE 1 functional Annotation Clustering (Gene Ontology)

| | Count | p-value |
|---|---|---|
| Annotation Cluster 1 | | Enrichment Score: 23.86 |
| Cell cycle process | 141 | 4.7E−30 |
| Cell cycle | 157 | 5.2E−30 |
| Mitosis | 70 | 8.1E−28 |
| M phase of mitotic cell cycle | 70 | 1.5E−27 |
| Mitotic cell cycle | 81 | 5.8E−26 |
| Cell division | 64 | 4.7E−22 |
| Regulation of cell cycle | 88 | 2.3E−15 |
| Annotation Cluster 2 | | Enrichment Score: 12.84 |
| Chromosome, pericentric region | 29 | 7.5E−15 |
| Chromosome | 68 | 5.3E−13 |
| Chromosomal part | 61 | 7.6E−13 |
| Annotation Cluster 3 | | Enrichment Score: 10.78 |
| Microtubule cytoskeleton | 77 | 2.7E−16 |
| Intracellular nonmembrane-bound organelle | 219 | 7.7E−15 |
| Microtubule | 49 | 2.4E−12 |
| Cytoskeleton | 140 | 2.6E−12 |
| Microtubule-based movement | 66 | 7.4E−8 |
| Cytoskeleton-dependent intracellular transport | 27 | 4.8E−7 |

Studies clearly suggest that there is a loss of "sternness" of MSCs when they are expanded in culture, if sternness is measured as the ability of the cells to be colonogenic and the potential to generate skeletal tissue in vivo. However, the loss of sternness can be retarded when cells are maintained on the cell-derived preservation ECM. During multiple passages, human MSCs cultured on cell-derived preservation ECM maintained high levels of replicative capability, accompanied by high levels of telomerase activity when compared with cells expanded on plastic. The activation of telomerase prevents telomere erosion and inhibits stem cell replicative senescence in vitro (Cong and Shay, 2008). Thus, it is possible that the cell-derived preservation ECM stabilizes high levels of telomerase activity, resulting in the extension of the life span of these cells. Furthermore, the studies showed that MSCs expanded on the cell-derived preservation ECM for multiple passages still retained the ability to form a relatively large volume of bone tissue. In contrast, the bone formation capacity of cells expanded on plastic was dramatically diminished after 6 to 7 passages. These findings suggest that culture of human bone marrow cells on such cell-derived preservation ECM may be useful for large-scale enrichment of MSCs without the need for extensive subculturing or passaging.

The loss of stem cell properties, coincident with the so-called spontaneous differentiation, may actually be due to the response of MSCs to growth factors produced endogenously in these cultured cells. It has been demonstrated that autocrine/paracrine production of BMP-2/4 is required for osteoblastogenesis when MSCs or osteoblast progenitors are cultured on plastic (Abe et al., 2000). Moreover, the inventor found that approximately 6% of endogenous BMP-2 proteins were in the supernatant and the majority was bound to the matrices in cultures maintained on the cell-derived preservation ECM when compared with approximately 40% in the supernatant in cultures maintained on the plastic. The fact that cell-derived preservation ECM sequesters endogenously produced BMP-2 may explain why MSCs retained an undifferentiated phenotype when cultured on the cell-derived preservation ECM. Other prodifferentiating proteins may also be sequestered by the cell-derived preservation ECM. Wnt proteins, a large family of ligands that regulate MSC differentiation via activation of LRP5 and LRP6, are known to bind to GAGs of the ECM (Reichsman et al., 1996). The results showed that this cell-derived ECM strongly promoted synovium-derived stem cell (SDSC) proliferation and greatly enhanced the chondrogenic capacity of SDSC. More importantly, SDSC maintained on the cell-derived ECM made by synovium-derived cells diminished their ability to differentiate into osteoblasts and adipocytes, which is evidence that tissue-specific cell-derived ECMs, including what we have termed "differentiation ECMs" may play a role in directing stem cell differentiation.

Study of the impact of the cell-derived preservation ECM on the self-renewal of MSCs would ideally use markers that distinguish MSCs from their more differentiated progeny, but such markers do not currently exist. Thus, the inventor has relied on the ability of MSCs to adhere to culture substratum and form a colony of cells that exhibit a fibroblast-like morphology. These colony-forming cells are called colony forming unit-fibroblast (CFU-F) (Pittenger et al., 1999); they are heterogeneous and comprise MSCs and their transit amplifying progeny (Di Gregorio et al., 2001). Thus, this population of cells has been defined as mesenchymal colony-forming units (MCFUs).

The inventor has previously established that most if not all of CFU-Fs of the murine bone marrow replicate during culture to produce additional CFU-Fs as detected in a subsequent replating assay. Moreover, 50% of these newly formed progenitors differentiated into osteoblasts in response to ascorbic acid (CFU-OB). Culture of murine marrow-derived MCFUs on a cell-free cell-derived preservation ECM made by murine marrow-derived cells promoted replication of MCFUs and dramatically restrained "spontaneous" differentiation. After expansion on this cell-derived preservation ECM, functional MCFUs were increased as shown by increased formation of bone and hematopoietic marrow tissue after subcutaneous transplantation of in vitro expanded MCFUs into immuno-compromised mice.

Furthermore, the gene expression profiles displayed a global picture to unbiasedly confirm that the cell-derived preservation ECM did restrain MSC differentiation. In addition to genes related to cell cycle and cell division, sets of genes were shown to highly relate to cytoskeleton and microtubule-based movement. These results support the observation that cell-derived preservation ECM promotes human MSC attachment and motility (data not shown).

During multiple passages, MSCs cultured on cell-derived preservation ECM maintained high levels of replicative capability, accompanied by high levels of telomerase activity, compared to cells expanded on plastic. The activation of telomerase prevents telomere erosion and inhibits stem cell replicative senescence in vitro (Cong and Shay, 2008). Thus, it is possible that the cell-derived preservation ECM stabilizes high levels of telomerase activity, resulting in the extension of the life-span of these cells. The quality of the expanded cells following each passage was further tested by an in vivo transplantation assay. The studies showed that MSCs expanded on the cell-derived preservation ECM for multiple passages still retained the ability to form a relatively large volume of bone tissue. In contrast, the bone formation capacity of cells expanded on plastic was dramatically diminished after 6-7 passages. These findings suggest that culture of human bone marrow cells on such cell-derived preservation ECM may be useful for large-scale enrichment of MSCs without the need for extensive subculturing or passaging.

The ECM modulates the activity of growth factors by controlling proteolytic activation of latent factors as in the case of TGF-$\beta$ (Dallas et al., 2002), and by sequestering factors such as PDGF and BMPs (Chen et al., 2007; Nili et al., 2003). ECM proteins also interact with receptors to regulate binding of the cognate ligand, as occurs in the case of the EGF receptor (Santra et al., 2002). Each of these mechanisms may contribute to the maintenance and expansion of MSCs when cultured on the stromal cell-derived preservation ECM. In this study, the inventor also observed that MSCs grown on the cell-derived preservation ECM underwent directional migration along the orientation of the cell-derived preservation ECM fibers with a decreased frequency of cell-cell contact, whereas MSCs grown on plastic showed random migration (data not shown).

The multi-lineage differentiation potential of MSCs is controlled by their interactions with a tissue-specific microenvironment or niche consisting of cell-derived ECM proteins associated with growth factors. For the purpose of reconstituting an optimal microenvironment for MSCs in vitro, a preservation ECM produced by bone marrow stromal cells was prepared. The cell-derived preservation ECM-based culture system described herein appears to provide an ideal environment for the large-scale expansion of highly functional MSCs for eventual use in stem cell-based therapy.

b. A Cell-Derived Tissue-Specific Stem Cell Differentiation ECM (the "Differentiation Matrix")

In some embodiments, the present invention provides a cell-derived tissue-specific stem cell differentiation extracellular matrix, also called a "differentiation matrix" generated by fibroblast cells. The fibroblast cells may be mammalian, for example human or mouse. The fibroblast cells may be from any desired tissue type or tissue source that contains fibroblast cells, including but not limited to neural tissue, skin (epidermal and/or dermal) tissue, adipose tissue, cardiac tissue, kidney tissue, muscle tissue, liver tissue, cartilage tissue, pancreas tissue, tissue of the endometrium of uterus, umbilical cord tissue, dental pulp tissue and trabecular and/or cortical bone tissue.

In some aspects, this invention provides tissue specific fibroblast-derived stem cell differentiation matrices generated by target tissue-specific fibroblast cells. In some aspects, this invention provides tissue specific differentiation matrices made by a method comprising a) culturing target tissue-specific fibroblast cells on a surface to produce an extracellular matrix; b) removing the fibroblast cells from the extracellular matrix to produce a fibroblast cell-free extracellular matrix. In some embodiments, the method further comprises treating the fibroblast cell-free extracellular matrix with DNase.

In some embodiments, the surface on which the fibroblast cells are cultured is coated with a substance, such as fibronectin or type I collagen. The fibroblast cells may be cultured for an appropriate number of days. In some embodiments, the fibroblast cells are cultured for 15 days. After the $8^{th}$ day, ascorbic acid may be added to the cell culture. The fibroblast cells may be from any desired subject. In some embodiments, the fibroblast cells are from a human or mouse subject. The fibroblast cells may be from any desired tissue type or tissue source that contains fibroblast cells, including but not limited to neural tissue, skin (epidermal and/or dermal) tissue, adipose tissue, cardiac tissue, kidney tissue, muscle tissue, liver tissue, cartilage tissue, pancreas tissue, tissue of the endometrium of uterus, umbilical cord tissue, dental pulp tissue and trabecular and/or cortical bone tissue. In some embodiments, the differentiation matrix is a 3D tissue-specific differentiation matrix. In some embodiments, the cell-derived differentiation matrix is essentially free of feeder cells. In some embodiments, the cell-derived differentiation matrix is essentially free of fibroblast cells.

D. Use of a Cell-Derived Tissue-Specific Differentiation Matrix

The use of a 3D preservation matrix for culturing MSCs is more relevant to the physiological situation than 2D culture systems. The 3D preservation matrix was made to mimic the bone marrow microenvironment and thus maintain MSC pluripotency. However, MSCs can and do differentiate into many distinct cell lineages depending on physiological need. In a natural system, the direction of MSC differentiation is controlled by the tissue-specific microenvironment or niche the MSC comes into contact with at a distant site of injury. The microenvironment is made up of mainly ECM proteins associated with growth factors, and is likely primarily responsible for influencing MSCs to differentiate into the cells associated with the specific microenvironment. Thus, in some aspects this invention provides for an in-vitro stem cell differentiation system utilizing the tissue-specific fibroblasts responsible for providing tissue-specific ECM proteins and growth factors responsible for tissue-specific differentiation of stem cell in-vivo. This system will result in a reliable, predictable and practical system to more 'naturally' influence stem cells, including MSCs, to differentiate into a specific desired cell lineage.

In some embodiments, the differentiation matrix is tissue-specific for a target cell type, where the cell-derived ECM is generated by tissue-specific fibroblast cells. The fibroblast cells may be mammalian, for example human or mouse. The fibroblast cells may be from any desired tissue type or tissue source that contains fibroblast cells, including but not limited to neural tissue, skin (epidermal and/or dermal) tissue, adipose tissue, cardiac tissue, kidney tissue, muscle tissue, liver tissue, cartilage tissue, pancreas tissue, tissue of the endometrium of uterus, umbilical cord tissue, dental pulp tissue and trabecular and/or cortical bone tissue.

To direct MSCs to differentiate into a specific lineage, they may be induced by being maintained on a tissue-specific differentiation matrix that simulates a specific microenvironment in vivo. Interestingly, the differentiation matrix may provide tissue-specific cues to stem cells. For example, ES cells form a polarized epithelium when cultured on Matrigel, but form a cartilaginous structure when cultured on matrices prepared from cartilage extracts (Philip et al., 2005). Culture of human or mouse MSCs on cell-free cell-derived preservation matrix made by marrow-derived stromal cells dramatically enhanced MSC self-renewal and retarded osteoblast differentiation, whereas culture of MSCs on collagen type I gels did not. Moreover, the sensitivity of BM-MSCs to exogenous BMP-2 was dramatically increased when they were grown on bone marrow-derived preservation matrix as compared to culture on a tissue-specific differentiation matrix made by skin fibroblasts (unpublished results). Comparative proteomic analysis demonstrated that bone marrow cell-derived preservation matrix and skin fibroblast-derived differentiation matrix contained 78 and 95 matrix proteins, respectively, 68 of which are overlapping. The distinct matrix proteins may be important for the specificity of this cell-derived preservation or differentiation matrix via their contribution to the architecture of the preservation or differentiation matrix or via their ability to interact with growth factors and MSCs themselves. To further define which proteins contribute to specific ECM regulation of MSC behavior, the inventor uses matrices made by cells from genetically manipulated animals, for example, bgn- or dcn-deficient mice, or by cells treated with siRNA to silence the tested protein. Alternatively, individual ECM components could be added back to the extracted ECM.

Tissue-specific differentiation matrices may be generated from a wide variety of tissue sources, including but not limited to neural tissue, skin (epidermal and/or dermal) tissue, adipose tissue, cardiac tissue, kidney tissue, muscle tissue, liver tissue, cartilage tissue, pancreas tissue, tissue of the endometrium of uterus, umbilical cord tissue, dental pulp tissue and trabecular and/or cortical bone tissue.

1. Induction of Mesenchymal Stem Cells Into a Target Cell Type Using the Cell-Derived Differentiation Matrix In some embodiments, the present invention provides a method of inducing tissue-specific differentiation of MSCs into a target cell type. As used herein, the term mesenchymal stem cells (MSCs) may refer to either pluripotent or multipotent stem cells. This method may comprise contacting isolated MSCs with a tissue-specific differentiation matrix generated by target tissue-specific fibroblast cells that induces the MSCs to differentiate into the target cell type. The target cell type may be any cell type desired, including but not limited to neurons, epithelial cells and/or dermal cells, adipocytes, cardiomyocytes, renal cells, myocytes, hepatocytes, chondrocytes, islet cells, endothelial cells, dental pulp cells, and osteoblasts.

In some embodiments, the isolated MSCs are cultured on the tissue-specific differentiation matrix with a tissue-specific differentiation medium. For example, in some embodiments, the tissue-specific differentiation matrix is epithelial or dermal cell derived and the tissue-specific differentiation medium contains α-MEM containing 15% FBS. In some embodiments, this method further comprises contacting the MSCs with a second differentiation factor known to induce commitment of a stem cell to a particular cell type.

2. Isolation of Mesenchymal Stem Cells Using the Cell-Derived Preservation Matrix In some embodiments, the present invention provides a method of isolating MSCs comprising contacting a MSC-containing sample with a cell-derived preservation matrix generated by human marrow stromal fibroblast cells; and isolating the MSCs from the cell-derived matrix. In some embodiments, the method further comprises expanding the isolated MSCs on a cell-derived preservation matrix generated by human marrow stromal fibroblast cells to generate a sample containing isolated MSCs. The MSC-containing sample may be from any source, including but not limited to periosteum, trabecular bone, adipose tissue, synovium, skeletal muscle, deciduous teeth, fetal pancreas, lung, liver, amniotic fluid, umbilical cord blood and umbilical cord tissues.

Umbilical cord blood (UCB) has been proposed as an alternative source of mesenchymal stem cells (MSCs) for stem cell therapy in areas of arthritis, heart disease, nerve, and tissue regeneration. It has been shown that UCB contains not only hematopoietic stem cells, but also MSCs that can differentiate into many distinct cell types including osteoblasts, chondrocytes, myocytes, endothelial cells, and neurons. Because of this finding, UCB has been proposed as an alternative source of MSCs for stem cell therapy in areas of arthritis, heart disease, nerve, and tissue regeneration. However, the major limitation in the use of UCB-MSCs for both research and clinical applications is that the frequency of MSCs in UCB is extremely low (~5 to 30 out of $1 \times 10^8$ mononuclear cells). Indeed, the successful rate of UCB-MSCs isolation is also low, approximately 30%. To date, MSCs are isolated from bone marrow or any other tissues by the classic plastic adhesion method because of a lack of specific markers that can define these cells. Using the same methodology, most of extremely immature MSCs in UCB are likely missed because their ability to adhere to plastic is poor.

Figure 29:
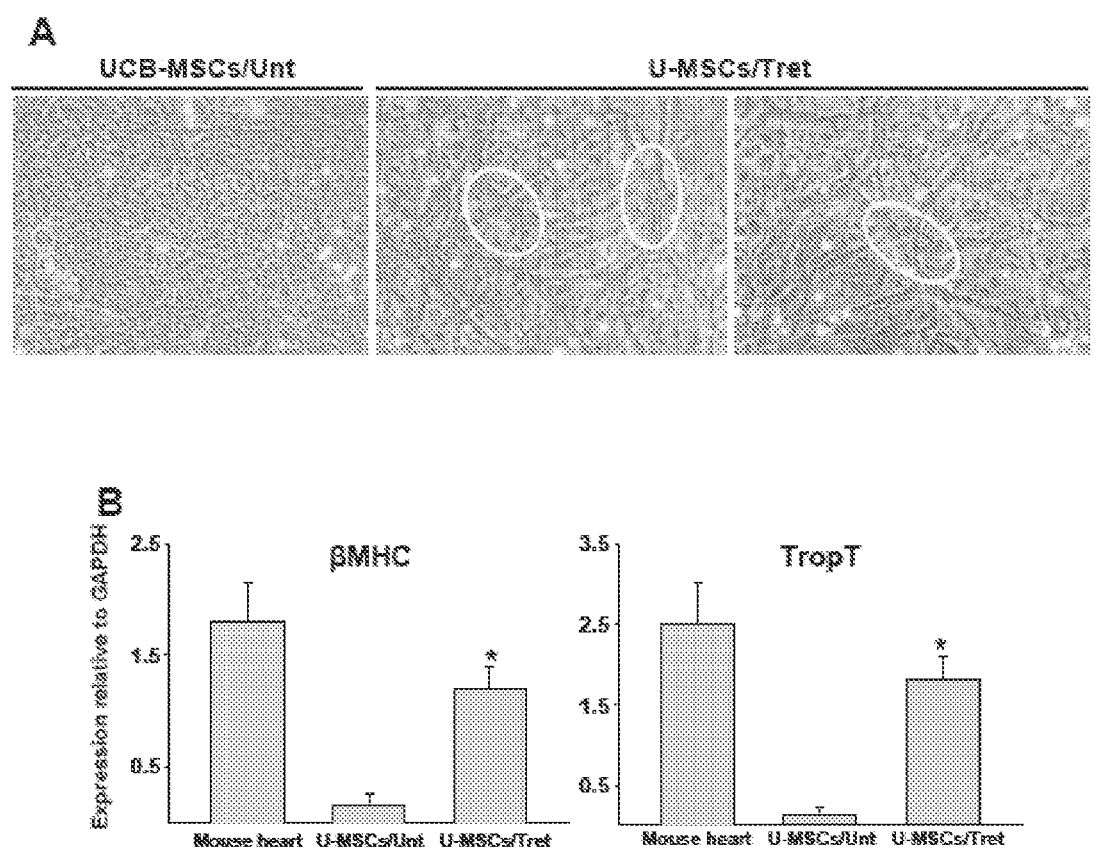
FIGS. 29A-B Cardiomyocytes differentiated from UCB-MSCs obtained by ECM adhesion. UCB-MSCs were treated with the differentiation medium (U-MSCs/Tret). As a negative control, UCB-MSCs were cultured in a growth medium (UCB-MSCs/Unt).
Figure 32:
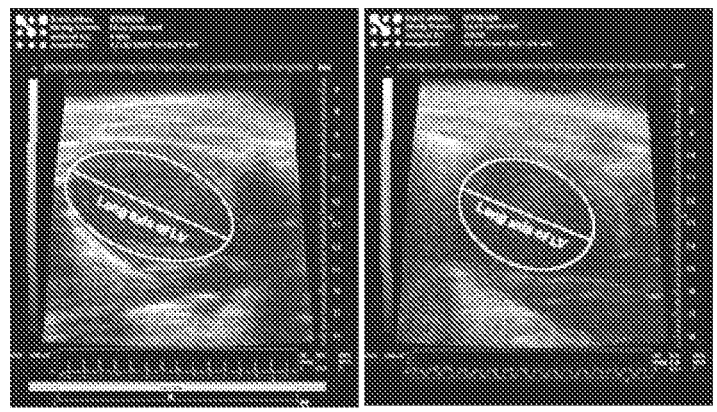
FIG. 32 Long axis views from the same mouse at baseline (left) and 7 d post-MI (right).
Figure 33:
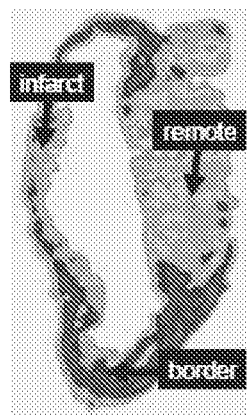
FIG. 33 Mouse LV transverse slice post-MI to indicate regions.

Bone marrow-derived extracellular matrix (ECM) facilitates the isolation and expansion of UCB-MSCs that exhibit features of human embryonic stem cells (hESCs). Using the cell-derived preservation ECM, the inventor was able to isolate large numbers of MSCs from UCB, indicating that the frequency is at least $1.5 \times 10^4$-fold greater than that reported by others who isolated UCB-MSCs using uncoated plastic (FIGS. 31 & 32), or plastic coated with fibronectin or 100% FBS. The phenotypes of cells adhered on the ECM were also determined by flow cytometric analysis, suggesting that ~50% of these cells expressed an ES cell marker SSEA-4 (Stage-specific Embryonic Antigen-4), and most cells also expressed several MSC markers including CD29, CD105, CD166 and CD146, but there was no expression of CD34 and CD45 hematopoietic cell markers (FIG. 29). More importantly, MSCs obtained by ECM adhesion appeared to form embryonic bodies in vitro, a unique feature of embryonic stem cells (FIG. 32, right panel), and generated tissues originated from 3 embryonic germ layers (mesoderm, ectoderm and endoderm) in vivo (FIG. 33). This method is further described in PCT application PCT/US2009/047981, which is incorporated herein by reference in its entirety.

In some aspects, the invention provides for the isolation of MSCs by adherence to a cell-derived preservation ECM. By using the cell-derived preservation ECM adhesion procedure, isolation of a surprisingly large number of embryonic-like stem cells from human umbilical cord blood was achieved.

3. Tissue Regeneration Using Stem Cells Grown on the Cell-Derived Differentiation Extracellular Matrix In some embodiments, the present invention provides a method of regenerating tissue or repairing damaged tissue comprising contacting a fully-expanded sample of stem cells (i.e., a sample of sufficient quantity to produce the desired effect) with a tissue-specific differentiation ECM, isolating the cells from the differentiation ECM, and administering the isolated cells to a subject in need of such treatment, particularly by injecting the cells into the damaged tissue or tissue in need of regeneration. The stem cells may be obtained from any appropriate source, including but not limited to ES cells, MSCs, or engineered stem cells (e.g. IPS cells).

It appears that human UCB contains a large number of embryonic-like stem cells that have the potential to be used for tissue regeneration in general and myocardial reconstruction in particular, thus in a particular embodiment, the stem cell sample comprises a human-UCB-derived MSC sample previously expanded on the preservation ECM, removed from the preservation ECM, transferred to and maintained on the differentiation ECM for a period of time sufficient to produce the desired cells and finally administered to a subject in need of such cells.

UCB as a potential source of stem cells for differentiation into cardiomyocytes and regeneration of myocardium after myocardial infarction. As the US population is aging, a greater population will undergo myocardial infarction (MI) and its consequences rank first in the mortality list. Occlusion of a coronary artery and the resultant MI rapidly results in myocardial necrosis followed by scar formation. Surviving cardiac myocytes undergo compensatory hypertrophy and the entire architecture of the left ventricular (LV) wall becomes rearranged in a process summarized as "ventricular remodeling." In general, the mammalian heart is unable to regenerate the large number of cardiomyocytes (CMs) lost after infarction to prevent LV remodeling and subsequent development of heart failure. The fundamental therapy is to replace damaged tissue with new contractile tissue. Currently, the best option for completely restoring cardiac function after a large MI is heart transplantation. However, it is limited by donor availability and transplant rejection. If it were possible to reconstitute the myocardium by replacing lost CMs, heart failure after MI could possibly be prevented, or at least heart function could be improved to prolong waiting time in order to increase chances for the patient to find a donor matched for heart transplantation.

Recently, regeneration of infarcted myocardium by injecting stem cells has been proposed as an alternative therapy. It has been demonstrated that ES cells from a variety of animal species including humans can spontaneously differentiate into cardiomyocytes, and transplanting these cells have shown success in improving myocardial function after MI. However, the maintenance of hES cells needs mouse embryonic feeder cells to inhibit their differentiation, which has the risk of pathogen transfer called "xenorisk." The more critical unsolved issues impair their therapeutic potential. The ability of BM-MSCs to differentiate into cardiac cells remains to be elucidated, albeit it has been reported that BM-MSCs can differentiate into cardiac lineages. In spite of these discrepant results, transplantation of autologous BM-MSCs has a potential disadvantage in that the number and function of such cells available to be harvested from MI patients are reduced.

Relevant literature regarding the efficacy of UCB-MSCs for myocardial reconstruction is very inconsistent and appears to be in conflict. Apparently, many of the inconsistencies are attributable to the lack of standard procedures to isolate and maintain these cells and to the lack of an appropriate animal model to evaluate the capacity of these cells to generate functional tissues. Recently, several groups have shown that UCB contains embryonic-like stem cells that were isolated by adhesion to plastic coated with fibronectin. These cells can differentiate into cells originated from three germ layers in vitro, but no convincing results in vivo have been reported. In addition, the number of these cells obtained by the plastic adhesion is also very low (4 out of $10^9$ mononuclear cells).

Figure 34:
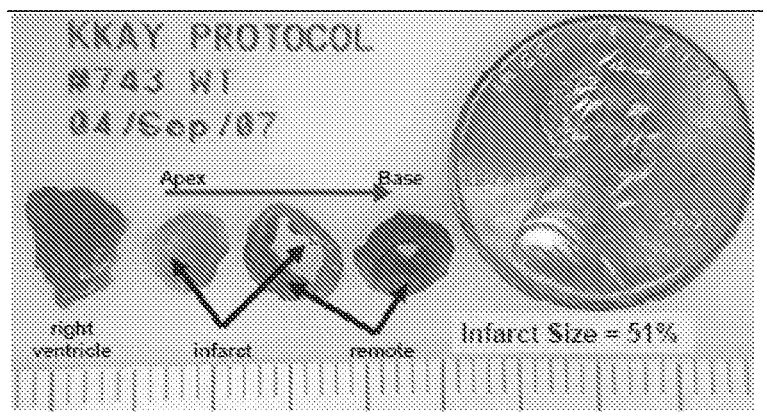
FIG. 34 A representative mouse heart following 7 days MI.
Figure 35:
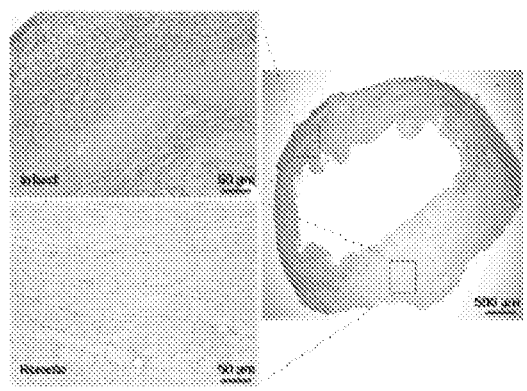
FIG. 35 Picrosirium red stained LV section from 7 day post-MI mouse. Left) infarct is top; remote region bottom.

Studies in vitro have indicated that UCB-MSCs obtained by cell-derived ECM adhesion can differentiate into myoblasts (FIG. 33) and by those in vivo implying that these cells may favor muscular genesis and angiogenesis (FIG. 34). Traditionally, stem cells are considered for the regeneration of tissue, but evidence suggests that stem cells can produce various cytokines needed and deliver them to a local area for the repair of defects. Transplantation of these cells into myocardium after a myocardial infarction (MI) may not only give rise to cardiomyocytes, but also increase the neovascularization that is critical to improve myocardial function.

4. Rejuvenating Old Stem Cells on a Young Cell-Derived Preservation Matrix

In some embodiments, the present invention provides a method for rejuvenating stem cells from an older subject by contacting those cells with an extracellular matrix generated by a subject that is younger relative to the first subject. This method can be used to revitalize the stem cells of any subject. For example, this method may be used to revitalize stem cells obtained from a human subject or a murine subject.

The quantity and quality of MSCs decreases with aging, which is associated with the progressive failure of function of tissues and organs. However, the precise phenotype of aged MSCs is unclear. Relevant literature is very inconsistent, and appears to be in conflict (Sethe et al., 2006). Apparently, the various methods for MSC isolation can lead to enrichment of different subsets of MSCs with different biological properties, which may explain the discrepancies in the literature. MSCs are surrounded by an ECM composed of collagens, adhesion proteins, proteoglycans, and growth factors, which form a unique microenvironment or niche (Fuchs et al., 2004; Moore and Lemischka, 2006). MSCs living in the ECM not only receive cues from the ECM, but also influence the ECM by secreting ECM components, and by proteolytic modification of proteins and growth factors in the ECM. The end result is a "give and take" relationship between MSCs and ECM, which defines MSC behavior (Behonick and Werb, 2003). There is strong evidence that the relative abundance of senescent MSCs in vivo increases with aging. The accumulation of such cells has negative implications for the integrity of the ECM (Campisi, 2005), which may further influence MSC adhesion, migration, proliferation, differentiation and survival.

In some aspects, this invention provides a method of treating a subject having a physiologic deficiency comprising a) contacting a sample containing MSCs with a rejuvenating matrix to produce a fully-expanded sample of rejuvenated MSCs (i.e., a sample of sufficient quantity to produce the desired effect); and b) introducing the rejuvenated MSCs into the subject, wherein the physiologic deficiency is treated. A "rejuvenating matrix" is a preservation matrix generated by fibroblast cells derived from a subject that is younger than the subject having a physiologic deficiency. The younger subject may be any amount younger than the subject having a physiologic deficiency. In some embodiments, the sample containing MSCs contains isolated MSCs. In some embodiments, the isolated MSCs are obtained by a method comprising a) contacting a MSC-containing sample with a preservation matrix; and b) isolating the MSCs from the preservation matrix. In further embodiments, this invention provides a method of treating a subject having a physiologic deficiency comprising a) obtaining MSCs from an elderly subject suffering from one or more "frailty"-related physiologic deficiencies (e.g., osteopenia, osteoporosis, sarcopenia, cachexia, etc.); b) contacting the MSCs with a rejuvenating matrix derived from a younger subject and maintaining the MSCs on the rejuvenating matrix for a time sufficient for the MSCs to be rejuvenated; and c) administering the rejuvenated MSCs into the elderly subject wherein the physiologic deficiency is treated. The physiologic deficiency may be any deficiency associated with the progressive failure of function of tissues and organs.

Here, a unique model to study the roles of MSC aging (cell intrinsic) and ECM or niche aging (cell extrinsic) was used. The inventor examined whether aging and oxidative stress negatively impact the number and ex vivo replication of MSCs, by comparing femoral marrow cells isolated from 3-month old (younger) versus 18-month old (older) female C57BL/6 mice. Due to evidence that aging of C57BL/6 mice is associated with decreased bone mineral density (BMD), decreased osteoblast number and bone formation (Chen, 2004; Knopp et al., 2005), the inventor examined whether aging negatively impacted the replication of MSCs as well as the capacity of MSCs for bone formation, by comparing femoral marrow cells isolated from 3-month old (young) versus 18-month old female C57BL/6 mice, and whether such features of young or old MSCs would be altered by exposure to an ECM made by marrow stromal cells from young or old mice. The data indicated that the frequency of number of MSCs in marrow from old mice, measured by their ability to form a colony of osteoblastic cells (CFU-OB) was only marginally lower than that of young mice. However, defects in the self-renewal and bone formation capacity of aged MSCs were remarkable. Strikingly, these defects were corrected by the provision of an ECM made by marrow stromal cells from young animals. The deleterious effect of aging on the replication of MSCs was remarkable and reproducible in comparison with the initial number of MSCs defined by colony forming units (CFU), suggesting that aging changes the quality of MSCs rather than the quantity of MSCs.

E. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation and Characterization of the Tissue-Specific Preservation Matrix

Materials and Methods

Animals.

Swiss Webster female mice, 6-8 wk old, were obtained from Harlan (Indianapolis, Ind., USA). The University of Arkansas for Medical Sciences Division of Laboratory Animal Medicine approved the animal use protocol.

Preparation of Cell-Free ECM from Cultured Bone Marrow Cells.

Femoral marrow cells were obtained as previously described (Di gregorio et al., 2001) and cultured in 6-well plates (Corning, Corning, N.Y., USA) at $3 \times 10^6$ cells/10-cm$^2$ well in 4 ml of a standard culture medium made up of a-MEM (Life Technologies, Grand Island, N.Y., USA) supplemented with glutamine (2 mM), penicillin (100 U/ml), streptomycin (100 p.g/ml; Sigma Chemical Co., St Louis, Mo., USA), and 15% preselected FBS (Atlanta Biologicals, Lawrenceville, Ga., USA). After 7 days of culture, nonadherent cells were removed by rinsing. The adherent stromal cell layer was dispersed with PBS containing 400 U/ml type II collagenase (Worthington Biochemical, Lakewood, N.J., USA) for 10 min at 37° C. Then $1 \times 10^5$ adherent cells were seeded onto a 10-cm$^2$ well of a 6-well plate containing a 24×30-mm Thermanox plastic coverslip (Nalge Nunc International, Rochester, N.Y., USA) and cultured for an additional 15 days. The medium was changed every 3-4 days; ascorbic acid (50 p,M; Sigma Chemical Co.) was added during the final 8 days of culture. After extensive washing with PBS, cells were removed from the ECM by incubation with 0.5% Triton X-100 containing 20 mM NH$_4$OH in PBS for 5 mM at 37° C., similar to a previously described procedure (Vlodaysky, 1999). The ECM was treated with DNase (100 units/ml; Sigma Chemical Co.) for 1 h at 37° C. The ECM was washed with PBS three times and stored in 2.0 ml of PBS containing penicillin (100 U/ml), streptomycin (100 p.g/ml), and fungizone (0.25 p.g/ml) at 4° C. for up to 4 mo.

Preparation of Tissue Culture Plates Coated with Fibronectin or Type I Collagen.

One milliliter of 25 p,g/ml fibronectin in PBS was added to each well of a 6-well plate and incubated for 1 h at 37° C. After rinsing with PBS, plates were used immediately for cell culture. Type I collagen (Sigma Chemical Co.) was dissolved at 0.1% in 1% acetic acid and diluted 10-fold with PBS. One milliliter of this solution was added to each well of a 6-well plate and incubated for 3 h at 37° C. Plates were rinsed with PBS and dried in the culture hood under UV light.

Scanning Electron Microscopy.

Samples were washed three times with PBS, fixed with 2% glutaraldehyde in 0.1 M sodium cacodylate buffer (pH 7.2) for 1 h, and transferred to 0.1 M cacodylate buffer solution. The specimens were dehydrated in ascending concentrations of ethanol (from 70% to 100%) and embedded in epon resin (Polysciences, Warrington, Pa., USA). After dehydration, the coversfips were attached to a stub and sputtered with gold-palladium. The specimens were examined using an FEI/Philips XL30 Field emission environmental scanning electron microscope (Hillsboro, Oreg., USA).

Immunohistochemistry.

The preparations were fixed for 30 min with 4% formaldehyde in PBS at room temperature, washed with PBS, and blocked with 5% normal goat serum containing 0.1% BSA in PBS for 1 h. The matrices were incubated with the relevant primary antibodies (1:10 dilution) in 2% goat serum for 2 h. Antibodies against biglycan, collagen type I, III, and V, fibronectin, decorin, perlecan, syndecan-1, and laminin, were purchased from Santa Cruz Biotechnology (Santa Cruz, Calif., USA). Nonspecific isotype IgG (1:10 dilution) was used as a negative control. After washing with PBS, samples were incubated with the appropriate horseradish peroxidase-conjugated secondary antibody (1:100 dilution) for 1 h, developed with a 3,3'-diaminobenzidine substratechromogen system (Dako, Carpinteria, Calif., USA) for 5 min, and counterstained with methyl green.

Determination of CFU-F, CFU-OB, and CFU-AD Number.

Freshly isolated murine femoral marrow cells, or marrow cells expanded on the various matrices, were placed into 6-well plates at various seeding densities, incubated for 4 h at 37° C. to allow attachment of adherent cells, and washed twice with PBS to remove the nonadherent cells. Then, $3 \times 10^6$ irradiated guinea pig feeder cells (Chen et al., 2002) were added immediately in 4 ml of standard culture medium containing 1 mM L-ascorbate-2-phosphate (Wako Chemicals, Richmond, Va., USA). One half of the medium was replaced every 5 days. After 10-12 days, CFU-F colonies were visualized with crystal violet. For determination of CFU-OB, BMP-2 (30 ng/ml) was added to the cell cultures at day 7. After 25 days of culture, CFU-OB colonies were visualized with von Kossa staining. For determination of CFU-AD, the cells were cultured as above but without L-ascorbate-2-phosphate for 7 days. Rosiglita-zone (100 nM) or vehicle (dimethylsulfoxide) was added to the cell cultures. After 10 days, the cultures were stained with Oil red 0 to visualize adipocytes. Colonies containing >50 cells were counted using a dissecting microscope.

Determination of MCFU Replication Capacity.

The replication of MCFUs (F-Tables 1 and 2) was determined by comparing the number present in the initial femoral marrow cell isolate to the number present after 6 days of culture on the various matrices, using a previously described replating assay (Di Gregorio et al., 2001). Freshly isolated bone marrow cells were pooled from six mice, and an aliquot was used to determine CFU-F. CFU-OB, and CFU-AD number as described above. The total number of each type of CFU present in the initial isolate was calculated by multiplying the number of CFUs per cell seeded by the number of cells present in the isolate. Portions of the remaining freshly isolated bone marrow cells were cultured in standard culture medium in 6-well plates at $7 \times 10^6$ cells per 10-cm$^2$ well on tissue culture plastic, the marrow cell-derived ECM, or they were incorporated into a type I collagen gel as previously described (Di Gregorio et al., 2001). After 6 days of culture to allow replication, nonadherent cells were removed; the adherent cells were detached with collagenase. The cells were counted and replated for quantification of CFU-F, CFU-OB, and CFU-AD number using the methods described for the determination of CFUs in the initial marrow isolate. The same number of cells were seeded for determination of CFU number regardless of their substratum used for expansion. The total number of CFUs after expansion (had the entire femoral marrow isolate been cultured on plastic or a particular ECM) was calculated by multiplying the number of CFUs obtained per cell seeded by the number of cells obtained after expansion and dividing the result by the fraction of the initial marrow isolate used for expansion. The fold change in CFU during the expansion was determined by dividing the calculated total number of CFU-F, CFU-OB, and CFU-AD after expansion by the total number of CFU-F, CFU-OB, and CFU-AD present in the initial femoral marrow cell isolate.

Quantification of Gene Expression During Culture of Bone Marrow Cells on Plastic or the Stromal Cell-Derived ECM.

Freshly isolated murine femoral marrow cells, pooled from six mice, were seeded at $3 \times 10^6$ cells/10-cm$^2$ well of a 6-well plate without or with the marrow cell-derived ECM and maintained in standard culture medium for up to 25 days. One half of the medium was replaced every 5 days. To isolate RNA, cells were rinsed three times with ice-cold PBS and extracted using Ultraspec reagent (Biotecx Laboratories, Houston, Tex., USA). RNA (2 µg) was reverse-transcribed using a High Capacity cDNA Archive Kit (Applied Biosystems, Foster City, Calif., USA). The transcripts of interest and that of the housekeeping gene GAPDH were amplified from cDNA by real-time PCR using TaqMan Universal PCR Master Mix and Assay Demand or Assay by Design primer and probe sets (Applied Biosystems). Amplification and detection were carried out with an ABI Prism 7300 Sequence Detection System (Applied Biosystems) as follows: 5-min denaturation at 95° C. for 10 min, 40 cycles of amplification including denaturation at 94° C. for 15 seconds, and annealing/extension at 60° C. for 1 minute. Gene expression was quantified by subtracting the GAPDH threshold cycle (Ct) value from the Ct value of the gene of interest and expressed as $2^{-\Delta Ct}$ as described by the protocol of the manufacturer.

Measurement of Alkaline Phosphatase Activity and Osteocalcin Secretion in Response to BMP-2.

Freshly isolated murine bone marrow cells, pooled from six mice, were seeded on tissue culture plastic or stromal cell-derived ECM at $3\times10^6$ cells per 10-cm² well in standard culture medium and cultured for 15 days. For measurement of alkaline phosphatase (ALP) response, FBS was reduced to 2%, and 3-300 ng/ml human recombinant BMP-2 (R&D Systems, Minneapolis, Minn., USA) was added. After 48 h, cells were lysed with 20 mM Tris, 0.5 mM $MgCl_2$, 0.1 mM $ZnCl_2$, and 0.1% Triton X. ALP activity was determined using a kit from Sigma Chemical Co. The ALP value was normalized for cell number by the amount of protein in the lysates and was expressed as ALP activity per minute per microgram. For measurement of the osteocalcin response, medium was removed 6 days after addition of BMP-2, and the osteocalcin levels were measured by radioimmunoassay (RIA; Biomedical Technologies, Stoughton, Mass., USA).

Measurement of BMP-2.

After extensive rinsing, BMP-2 was extracted from the ECM/cell layer using 2 M urea, 2% SDS, 10% glycerol, and 10 mM Tris-HCl, pH 6.8.[25] The amount of BMP-2 in the culture supernatant and the extracts were measured using a murine-specific ELISA Assay Kit (R&D Systems).

Flow Cytometry.

Single-cell suspensions were obtained from the expanded cells by collagenase treatment (400 U/ml for 10-15 min at 37° C.) followed by two washes in cold PBS containing 5% FCS. For antibody staining, cells ($1-2\times10^6$) were incubated in 100 p,I of diluted (10 p,g/ml) anti-CD45 antibody (BD Biosciences, San Jose, Calif., USA) for 30 min at 4° C. The stained cells were washed twice in staining buffer (PBS containing 5% FCS and 0.01% sodium azide) and incubated in 20 µg/ml of FITC-conjugated goat anti-mouse IgG for 20 min at 4° C., washed twice with staining buffer, and either immediately analyzed by flow cytometry or fixed with 1% paraformaldehyde in PBS and analyzed within 96 h. Cells were stained with isotype IgG as a negative control. The cell suspensions were analyzed using a Becton Dickinson FACStarPlus flow cytometer. For each sample, 10,000 events were collected. The percentage of positive-stained cells was derived directly from the fluorescence-activated cell sorting (FACS).

In Vivo Bone Formation.

Freshly isolated murine marrow cells, pooled from 15 mice, were seeded at $7\times10^6$ cells per 10-cm² well on tissue culture plastic or the marrow cell-derived ECM and cultured for 7 days. After rinsing with PBS, cells were detached with collagenase. The cells ($1\times10^6$) were loaded into hydroxyapatite/tricalcium phosphate (HA/TCP) ceramic powder (Zimmer, Warsaw, Ind., USA) and implanted subcutaneously into the dorsal surface of 10-wk-old immunodeficient beige mice (NIH-bg-nu-xid; Harlan Sprague Dawley, Indianapolis, Ind., USA), as previously described (Krebsbach et al., 1997; Bi et al., 2005). Cells precultured on tissue culture plastic were implanted on the left side, and cells precultured on the marrow-derived ECM were implanted on the right side of each animal. As a negative control, an HA/TCP vehicle without cells was implanted into a mouse. Transplants were harvested after 4 or 8 wk (three animals for each), fixed in 10% phosphate-buffered formalin at 4° C. for 24 h, decalcified with 5% EDTA (pH 8.0) at room temperature for 1-2 wk, and embedded in paraffin. Each ossicle was bisected, and three sections (10 µm thick) were cut starting at the bisection point of each half-ossicle at 100-p.m intervals to yield a total of 18 sections for each ossicle. Sections were stained with H&E, and the percentage of the total ossicle area containing new bone or hematopoietic marrow was measured using Osteometrics image analysis software (Ostomeasure version 3.00; Osteometrics, Atlanta, Ga., USA).

Statistical Analysis.

Data are presented as mean±SD. Statistically significant effects were detected with Student's t-test or one-way ANOVA, using SigmaStat (Systat Software, Point Richmond, Calif., USA). Statistically significant differences among multiple treatment groups were detected after correction by Bonferoni's method. $p<0.05$ was considered significant.

Results

Characteristics of the Marrow Cell-Derived Preservation Matrix.

Consistent with earlier studies (Campbell et al., 1985), adherent cells cultured from murine femoral bone marrow elaborated a fibrillar ECM as revealed by scanning electron microscopy (SEM; FIG. 1A). Some debris remained after removal of cells, as reported previously in the case of epithelial cell-derived ECM preparations (Gospodarowicz et al., 1984). The ECM contained fibers of ~25-50 nm diameter, similar to that of collagenous fibrils seen in the bone marrow. The ECM was ~100 µm thick as determined by transmission electron microscopy (data not shown).

When examined before removal of cells, immunostaining revealed the presence of collagen types I, III, and V, syndecan-1, perlecan, fibronectin, laminin, biglycan, and decorin associated with the ECM, and sometimes within adherent cells (FIG. 1B). The composition of the ECM is consistent with that previously reported for the ECM made by cultured marrow stromal cells and are similar to the composition of the bone marrow ECM (Hamilton and Campbell, 1991; Klein, 1995; Gordon, 1988). For the most part, the cell extraction procedure did not seem to affect the composition of the ECM as determined by the semiquantitative immunostaining procedure; however, collagen type V and syndecan-1 immunostaining was significantly reduced after extraction (FIG. 1B).

Culture on Marrow Cell-Derived Preservation Matrix Restrains Differentiation and Promotes Replication of MCFUs.

The inventor first determined the effect of the ECM on the adherence of MCFUs capable of forming a colony of fibroblastic cells (i.e., CFU-F). In this experiment, freshly isolated murine marrow cells were allowed to adhere for 4 h to plastic, the cell-derived ECM, plastic coated with fibronectin, or plastic coated with type I collagen. Nonadherent cells were removed, and feeder cells (irradiated guinea pig marrow cells) were added to facilitate colony formation at the low seeding density used for this experiment (Kuznetsov and Robey, 1996). The colonies that subsequently formed on the marrow cell-derived ECM appeared larger, and the cells tended to be more densely packed, compared with the colonies that developed on tissue culture plastic or tissue culture plastic coated with fibronectin or type I collagen (FIG. 2A). In addition, there was a 2- to 3-fold increase in the number of CFU-F when seeded on the marrow cell-derived ECM compared with the other matrices tested (FIG. 2B).

The inventor also examined the ability of MSCs to differentiate into osteoblasts in response to addition of BMP-2 or into adipocytes in response to rosiglitazone. MCFUs that gave rise to colonies containing osteoblasts or adipocytes were designated as CFU-osteoblast (CFU-OB) and CFU-adipocyte (CFU-AD), respectively. When cultured in the presence of BMP-2 to stimulate osteoblastogenesis, the number of CFU-OB, as well as the degree of von Kossa staining for mineral within each colony, was increased when the cells were cultured on the ECM (FIG. 2A). The inventor also found that the number of CFU-AD was increased when cells were cultured on the stromal cell-derived ECM, and they contained more Oil red 0-stained adipocytes compared with cells cultured on tissue culture plastic or plastic coated with fibronectin or type I collagen. These observations indicate that more MCFUs adhere to the marrow cell-derived ECM and that they gave a stronger response to pro differentiating factors.

Examination of the morphology of cells within CFU-F colonies by SEM revealed that, after 5 days of culture on tissue culture plastic, cells were round and flat, and there was no evidence of an endogenous ECM. However, cells cultured on the marrow cell-derived ECM were embedded within the matrix, and they exhibited a fibroblastic morphology with extensive cellular processes (FIG. 2C). After 10 days of the culture, some of the cells maintained on plastic had begun to elaborate and become embedded in an ECM; however, they did not exhibit the same morphology as cells cultured on the marrow cell-derived ECM. In both conditions, round cells with a morphology characteristic of hematopoietic cells (Freund et al., 2006) were present at 10 days of culture.

The inventor next studied whether the marrow cell-derived ECM prevented "spontaneous" differentiation of MCFUs. In this experiment, murine bone marrow cell cultures were established at the seeding density commonly used for expansion of MCFUs (i.e., higher than that used for colony assays). Nonadherent cells were not removed, and exogenous guinea pig feeder cells were not added because, at this seeding density, it is thought that endogenous cells serve this function (Chen et al., 2002). Cell number, as reflected by RNA content, progressively increased during the first 15 days of culture (FIG. 3A). However, when examined at day 20, cells were confluent (FIG. 3B). Cells were grouped into nodules when maintained on plastic, whereas cells cultured on the marrow cell-derived ECM were evenly distributed. The expression of the osteoblast markers ALP, osteocalcin, bone sialoprotein, and type I collagen progressively increased during 25 days of culture on plastic (FIG. 3C), consistent with the "spontaneous" differentiation of MCFUs reported previously (Baksh et al., 2004). In contrast, the marrow cell-derived ECM preparation significantly delayed the appearance of these osteoblast markers. In a separate experiment, there was practically no mineral deposition, as determined by von Kossa staining, when cells were maintained on the marrow cell-derived ECM for 25 days (data not shown).

The restraint of osteoblastogenesis seen in cultures of MCFUs maintained on marrow cell-derived ECM was not caused by increased production of antagonists of the bone morphogenetic proteins (BMPs) or Wnt proteins needed for osteoblast differentiation. Indeed, transcript levels of such antagonists, including Sost, Noggin, Dkkl, Twisted gastrulation, Gremlin, and Chordin, in cultures maintained on plastic was significantly higher than in cultures maintained on this ECM (FIG. 3D). The inventor also noted a transient increase in Gremlin on day 7 in cells cultured on either plastic or the ECM.

The inventor has previously shown that autocrine/paracrine production of BMP-2 and BMP-4 mediate the osteoblastogenesis that occurs when MCFUs are cultured on plastic (Abe et al., 2000). Hence, the restraint of osteoblast differentiation observed in cultures maintained on the marrow cell-derived ECM could be caused by decreased synthesis of endogenous BMP-2. However, BMP-2 mRNA levels were similar in both culture conditions (FIG. 4A). In a separate experiment, the inventor determined that cell-free ECM preparations contained no detectable BMP-2 (data not shown). However, the amount of BMP-2 protein was increased by ~30% in cultures maintained for 15 days on the marrow cell-derived ECM compared with plastic (FIG. 4B). Strikingly, and in agreement with evidence that BMPs bind to components of the ECM (Chen et al., 2004), the inventor found that >90% of BMP-2 protein was associated with the cell/matrix layer in cultures maintained on the marrow cell-derived ECM compared with 60% in the case of cultures maintained on the plastic. Moreover, BMP-2 levels in the culture supernatant were 4-fold lower in the ECM cultures compared with cells cultured on plastic. Thus, it is possible that the restraint of osteoblast differentiation when MSCs were cultured on the marrow cell-derived ECM is related to sequestration of BMP-2 by the ECM.

The inventor next examined whether MCFUs retain their osteo-blastogenic response to exogenous BMP-2 when grown on the ECM. In this experiment, BMP-2 was added at 15 days after establishment of the cultures. When cultured on the marrow cell-derived ECM, as little as 3-10 ng/ml recombinant human BMP-2 stimulated ALP activity and osteocalcin secretion (FIG. 4C), as well as the level of ALP and osteocalcin mRNA (FIG. 4D). Basal ALP activity was already elevated in cultures maintained on tissue culture plastic compared with the ECM, consistent with the data of FIG. 3C showing an increase in ALP transcripts at the early stage of culture. These findings indicate that MCFUs retained their ability to differentiate into osteoblasts in response to exogenous BMP-2 when cultured on the marrow cellderived ECM. Addition of exogenous BMP-2 to cells maintained on plastic modestly increased ALP activity and Osteocalcin secretion but only at 30-100 ng/ml of added BMP-2 (FIG. 4C). BMP-2 had no effect on ALP mRNA in these cultures, but osteocalcin mRNA was increased at 100 ng/ml BMP-2. Higher levels of exogenous BMP-2 are evidently needed to further enhance osteoblastogenesis beyond that already stimulated by endogenous BMPs when the cells were cultured on plastic.

Marrow Cell-Derived Preservation Matrix Promotes MCFU Replication while Retaining Multipotentiality.

The replication of MCFUs during culture on the various matrices was determined by measuring the increase in CFU number using a replating assay that the inventor has previously described (Di Gregorio et al., 2001). Freshly isolated bone marrow cells were divided into aliquots for the determination of CFUs present in the initial isolate and after expansion on plastic or the marrow cell-derived ECM, as well as in type I collagen gels, which the inventor has used previously for determination of CFU replication (Di Gregorio et al., 2001). During the 6-day expansion period, non-adherent cells were not removed, and exogenous guinea pig feeder cells were not added. As shown in Table 2, the number of cells obtained after 6 days of culture on the ECM was increased compared with cells cultured on plastic or in type I collagen gels (Di Gregorio et al., 2001). The frequency of the MCFUs in the replating assay was –50% greater than in cells expanded on plastic or type I collagen gel (Table 2). The total number of CFU-F present in the cultures expanded on the marrow cell-derived ECM was increased 47-fold over the number of CFU-F present in the initial bone marrow isolate (Table 2; FIG. 5). In contrast, CFU-F increased 10- and 27-fold in cultures maintained on plastic and type I collagen gel, respectively. The number of MCFUs capable of differentiating into osteoblasts or adipocytes, after expansion, was also measured by inducing differentiation with ascorbate-2-phosphate and BMP-2, or rosiglitazone, respectively. The inventor found that the increase in the number of CFU-OB and CFU-AD was 2- to 4-fold greater when cultured on the marrow cell-derived ECM compared with cultured on plastic or type I collagen gel. CFU-F replication was greater than that of CFU-OB and CFU-AD, regardless of the matrix used for expansion. Hence, even though the expansion of CFU-F, CFU-OB, and CFU-AD was greater when the cells were cultured on the marrow cell-derived ECM, the culture substratum did not alter the proportion of MCFUs that could differentiate into osteoblasts or adipocytes.

In the above experiment, MCFU number was determined using a standard procedure in which cells were assayed on plastic before or after expansion. However, it is possible that MCFUs expanded on plastic versus the preservation ECM have different adhesion characteristics. Such a difference could influence the estimation of MCFU replication because the number of MCFUs (determined in the standard assay) could be different from the number of MCFUs adhering to the preservation ECM during expansion. To study this issue, the inventor performed an experiment in which the same culture substratum was used for both enumeration and expansion of CFU-Fs. As shown in Table 3, more CFU-Fs in the initial marrow isolate adhered to the ECM compared with plastic, consistent with the data of FIG. 2. Nevertheless, the increase in CFU-Fs during culture on the marrow cell-derived preservation ECM was 2-fold greater than when expanded on plastic. Therefore, although there are differences in CFU-F adherence to plastic versus the preservation ECM, such differences do not unfairly bias determination of CFU-F replication. The inventor also found in this experiment that the majority of the expanded cells comprised CD45± hematopoietic cells (determined by flow cytometry), regardless of whether cells were cultured on plastic or the marrow cell-derived preservation ECM, and that the number of CD45+ hematopoietic cells present in cultures maintained on the preservation ECM is higher than that maintained on plastic. Thus, the preservation ECM promoted increased replication of both MCFUs and hematopoietic cells.

TABLE 2

CALCULATION OF CFU REPLICATION

|  | CFU-F | CFU-OB | CFU-AD |
|---|---|---|---|
| CFUs in initial marrow isolate No. CFUs (per $10^6$ cells) | 32 ± 2 | 24 ± 7 | 25 ± 4 |
| Total CFUs (×$10^3$) in 1.8 × $10^8$ BMNCs (total isolate) | 5.7 ± 0.3 | 4.4 ± 1.4 | 4.4 ± 0.7 |
| CFUs after expansion |  |  |  |
| Matrix used for expansion | Tissue culture plastic | Type I collagen gel | Marrow cell ECM |
| Fraction of BMNCs used for expansion* | 0.23 | 0.23 | 0.16 |
| No. adherent cells after expansion (×$10^6$/well) | 0.32 | 1.2 | 1.25 |
| Total no. adherent cells after expansion (×$10^6$)$^t$ | 1.9 | 7.2 | 5.0 |

|  | CFU-F | CFU-OB | CFU-AD | CFU-F | CFU-OB | CFU-AD | CFU-F | CFU-OB | CFU-AD |
|---|---|---|---|---|---|---|---|---|---|
| No. CFUs after expansion (×$10^3$/$10^6$cells) | 6.7 ± 1.1 | 0.8 ± 0.1 | 0.4 ± 0.1 | 4.9 ± 1.0 | 0.6 ± 0.1 | 0.4 ± 0.1 | 8.5 ± 0.8 | 12 ± 0.1 | 0.6 ± 0.1 |
| Total CFUs after expansion (×$10^3$)* | 13.8 ± 2.2 | 1.6 ± 0.2 | 0.7 ± 0.1 | 35.5 ± 7.2 | 4.5 ± 0.5 | 2.6 ± 0.5 | 42.7 ± 4.1 | 5.9 ± 0.1 |  |
| Total CFUs after expansion of | 3.2 ± 06 |  |  |  |  |  |  |  |  |
| Fold change during expansion$^5$ | 55.0 ± 9.5 | 6.8 ± 0.9 | 3.2 ± 0.3 | 154.4 ± 31.6 | 19.6 ± 2.3 | 11.4 ± 2.4 | 266.7 ± 26.0 | 36.7 ± 0.8 | 20.1 ± 3.9 |
| total initial isolate (×$10^3$)$^4$ |  |  |  |  |  |  |  |  | 9.7 ± 1.8 |

*Number of BMNCs used for expansion divided by number of BMNCs in initial isolate.
$^{1.}$ From six wells (tissue culture plastic or type I collagen) or four wells (marrow ECM).
*Number of CFUs per $10^6$ cells multiplied by total number of cells obtained after expansion.
Total number of CFUs after expansion divided by fraction of cells used for expansion.
Total number of CFUs after expansion divided by the total number of CFUs present in the initial isolate.
$^{66}$p < 0.05 by ANOVA vs. fold change of the same type of CFU after expansion on type I collagen gel, and plastic. tt p < 0.05 vs. the same type of CFU after expansion on plastic.
BMNCs, bone marrow mononuclear cells.

TABLE 3

ANALYSIS OF CFU-F AND CD45* CELLS AFTER CULTURE ON PLASTIC OR MARROW CELL-DERIVED PRESERVATION ECM

|  | Plastic | ECM |
|---|---|---|
| | Initial marrow cell isolate | |
| No. CFU-F in initial marrow cell isolate (per $10^6$ cells) | 24 6 | 46 ± 4 |
| Total CFU-F in initial marrow cell isolate ($\times 10^3$) | 10.4 ± 2.7 | 19.6 ± 5.7* |
| | Marrow cell expansion | |
| No. cells after expansion ($10^6$/well) | 0.4 | 1.2 |
| Total cells after expansion ($\times 10^6$)* | 3.5 | 4.9 |
| CD45 cells (%) | 57 | 78 |
| | CFII-F after expansion | |
| No. CFU-F after expansion ($1010^6$ cells) | 10.0 ± 0.4 | 13.6 ± 0.4 |
| Total CFU-Fs after expansion ($\times 10^3$) | 35.0 ± 1.4 | 66.6 ± 2.0 |
| Total CFU-Fs after expansion of total marrow cell isolate ($\times 10^3$)† | 276.5 ± 11.1 | 1046.6 ± 31.2 |
| Fold change during expansion | 27 ± 7 | 53 ± 15 |

*Plastic, pooled from eight wells; ECM, pooled from four wells.
† Total CFU-Fs after expansion divided by fraction of cells used for expansion (plastic, 0.127; ECM, 0.063). *See footnotes for Table 1 for calculation of fold change.
$p < 0.05$ vs. plastic.

To show the capacity of MCFUs expanded on the marrow cell-derived preservation ECM to generate skeletal tissue, the inventor used a transplantation assay (Bi et al., 2005). After 7 days of culture of bone marrow cells on plastic or on marrow cell-derived ECM, $1 \times 10^6$ adherent cells were loaded onto an HA/TCP carrier and implanted subcutaneously into immuno-compromised NIH-bg-nu-xid mice. The inventor found that, whereas little bone was formed at 4 wk after implantation by cells expanded on plastic, there was substantial bone formed by cells expanded on the preservation ECM at this time-point (FIG. 6E). The amount of bone generated at 8 wk after implantation of cells precultured on plastic was ~3% of the total area of the ossicle. This finding is consistent with previous reports that implantation of $3-5 \times 10^6$ murine marrow cells expanded on plastic for at least one passage generated bone ossicles containing ~5-7% bone tissue (Bi et al., 2005; Miura et al., 2004). There was no bone in implants that were not loaded with cells (data not shown). The inventor also found that there was minimal hematopoietic marrow in ossicles made by cells expanded on plastic, and adipocytes and osteoclasts were rarely observed (FIGS. 6A, 6E, and 6F). In contrast, transplantation of $1 \times 10^6$ cells expanded on marrow cell-derived preservation ECM generated five times more bone than the cells precultured on tissue culture plastic (FIGS. 6B and 6E). The hematopoietic marrow of the ossicles made by MCFUs grown on the preservation ECM was characterized by a large number of adipocytes and was observed at 8, but not 4, wk after implantation (FIG. 6C). The area of hematopoietic marrow was 8-fold higher in ossicles made by cells cultured on the preservation ECM compared with cells cultured on plastic (FIG. 6F). Osteoclasts were also present in ossicles made by cells precultured on the preservation ECM (FIG. 6D).

Example 2

Preparation and Characterization of the Preservation Matrix

Materials and Methods

Animals.

Swiss Webster female mice, 6-8 weeks old, were obtained from Harlan (Indianapolis, Ind.). The University of Arkansas for Medical Sciences Division of Laboratory Animal Medicine approved the animal use protocol.

Scanning Electron Microscopy.

Samples were washed three times with PBS and fixed with 2% glutaraldehyde in 0.1M sodium cacodylate buffer (pH 7.2) for one hour and then transferred to 0.1 M cacodylate buffer solution. The specimens were dehydrated in ascending concentrations of ethanol (from 70% to 100%), embedded in peon resin (Poly/bed 812 Polysciences Int., Warrington, Pa.), and then coated with gold and palladium. After dehydration the coverslips were attached to a stub and sputtered with gold-palladium. The gold-palladium-coated cultures were examined using an FRI/Philips XL30 Field emission environmental scanning electron microscope (Hillsboro, Oreg.).

Immunohistochemistry.

Stromal cell-derived preservation ECM, before or after removal of cells, was fixed for 30 minutes with 4% lbrmaldehyde in PBS at room temperature, washed with PBS, and blocked with 5% normal goat serum containing 0.1% BSA in PBS for one hour. The matrices were then incubated with the relevant primary antibodies (1:10 dilution) in 2% goat serum for two hours. Antibodies against biglycan, collagen type I, III, V, fibronectin, decorin, perlecan, syndecan-1, and laminin, were purchased from Santa Cruz Biotechnology (Santa Cruz, Calif.). Non-specific isotype IgG (1:10 dilution) was used as a negative control. After washing with PBS, samples were incubated with the appropriate horseradish peroxidase-conjugated secondary antibody (1:100 dilution) for one hour, developed with a 3,3'-diaminobenzidine substrate-chromogen system (Dako Corp., Carpinteria, Calif.) for five minutes, and then counterstained with methyl green.

Determination of Colony-Forming Unit Fibroblast (CFU-F), Osteoblast (CFU-OB), and Adipocyte (CFU-AD).

Freshly isolated murine femoral marrow cells were plated into 6-well plates at the indicated seeding densities, incubated for four hours at 37° C. to allow attachment of adherent cells, and washed twice with PBS to remove the non-adherent cells. Then, irradiated guinea pig feeder cells ($3 \times 10^6$) were added immediately in 4 ml of the a-MEM medium described above containing 1 mM L-ascorbate-2-phosphate (Wako Chemicals, Richmond, Va.). After approximately 10 to 12 days (CFU-F) or 25 days (CFU-OB), colonies were visualized with crystal violet or Von Kossa staining, respectively. For determination of CFU-AD, 100 nM rosiglitazone or vehicle (dimethylsulfoxide) was added to the cell cultures at day seven. On day 25, the cultures were stained with Von Kossa to visualize colonies containing mineralizing osteoblasts and with Oil Red 0 to visualize adipocytes. Colonies containing more than 50 cells were counted using a dissecting microscope.

Measurement of MSC self-renewal has been previously described. Briefly, freshly isolated bone marrow cells were pre-cultured onto 6-well plates with or without the cell-free preservation ECM or pre-cultured in a type I collagen gel at $7 \times 10$ cells per well for 7 days. Cells were collected following treatment with collagenase and reseeded onto standard tissue culture plastic with irradiated guinea pig feeder cells in 4 ml of the a-MEM medium described above containing 1 mM L-ascorbate-2-phosphate for CFU-F, CFU-OB, and CFU-AD assays.

Quantification of Gene Expression in Cultured Bone Marrow Cells.

Total

RNA was extracted using Ultraspec reagent (Biotecx Laboratories, Inc., Houston, Tex.). RNA (2 lig) was reverse-transcribed using a High Capacity cDNA Archive Kit (Applied Biosystems, Foster City, Calif.). The transcripts of interest, and that of the housekeeping gene GAPDH, were amplified from cDNA by real-time PCR using TaqMan Universal PCR Master Mix and Assay Demand or Assay by Design primer and probe sets (Applied Biosystems). Amplification and detection were carried out with an AB1 Prism 7300 Sequence Detection System (Applied Biosystems) as follows: denaturation at 95° C. for 10 minutes, 40 cycles of amplification including denaturation at 94° C. for 15 seconds and annealing/extension at 60° C. for one minute. Gene expression was quantified by subtracting the GAPD11 threshold cycle (Ct) value from the Ct value of the gene of interest, and expressed as $2^{-\Delta Ct}$, as described by the protocol of the manufacturer.

Measurement of Alkaline Phosphatase (ALP) Activity and Osteocalcin Secretion in Response to BMP2.

Freshly isolated murine bone marrow cells were cultured in a-MEM described above for 15 days. For measurement of ALP response, FBS was reduced to 2% and then human recombinant BMP2 (R&D Systems, Inc., Minneapolis, Minn.) was added. After 48 hours, cells were lysed (20 mM Tris, 0.5 mM $MgCl_2$, 0.1 mM $ZnCl_2$ and 0.1% Triton X) and ALP activity was determined using an alkaline phosphatase kit (Sigma Chemical Co., St. Louis, Mo.). The ALP value was normalized by the amount of protein in the lysates, and was expressed as ALP activity/minute/ug. For measurement of the osteocalcin response, medium was removed six days after addition of BMP2, and the osteocalcin levels were measured by RIA (Biomedical Technologies Inc., Stoughton, Mass.).

Measurement of BMP2.

Murine bone marrow cell cultures were established on plastic or on the marrow stromal cell-derived preservation ECM in 6-well plates. After 15 days, the supernatant was collected. After extensive rinsing, BMP2 was extracted from the ECM/cell layer using 2M urea, 2% SDS, 10% glycerol and 10 mM Tris-HCl pH 6.8.° [8] The amount of BMP2 in the culture supernatant and the extracts was measured using a murine specific ELISA Assay Kit (R&D Systems, Minneapolis, Minn.).

In Vivo Bone Formation.

Marrow cells were cultured for seven days on plastic or the stromal cell-derived preservation ECM. Adherent cells ($1 \times 10^6$) were loaded into a transplantation vehicle such as, for example, hydroxyapatite/tricalcium phosphate (HA/TCP) ceramic powder (Zimmer Inc, Warsaw, Ind., USA), and transplanted subcutaneously into the dorsal surface of 10-week-old immunodeficient beige mice (NIHbg-nu-xid, Harlan Sprague Dawley, Indianapolis, Ind.), as previously described (Krebsbach et al., 1997; Bi et al., 2005). Three transplants were made for each pre-culture system. Transplants were harvested after four or eight weeks, fixed in 10% phosphate buffered formalin at 4° C. for 24 hrs, decalcified with 5% EDTA (pH 8.0) at room temperature for 1-2 weeks, and then embedded in paraffin. Each ossicle was bisected, and three sections (10 Km) were cut from each part at 100 um intervals. A total of nine H&E stained sections were used for quantification. The percentage of the area of new bone and hematopoietic marrow formed in transplants was measured by using Osteometrics image analysis software (Ostomeasure version 3.00, Osteometrics Inc., Atlanta, Ga.).

Statistical Analysis.

All data are presented as mean±standard deviation. Statistical analyses were done by using Student's t test or one-way ANOVA. Differences of $P<0.05$ were considered significant.

Results

Figure 19:
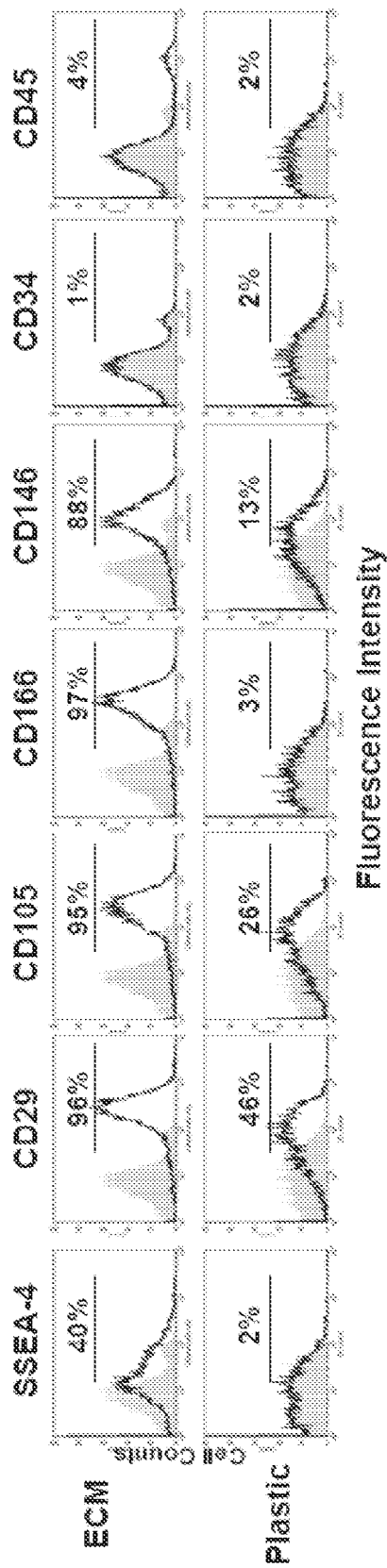
FIG. 19 Flow cytometric analysis of cells isolated by the ECM adhesion method (ECM) vs. cells isolated by a classical plastic adhesion method (Plastic). In the same experiments previously described in FIG. 16, single-cell suspensions were obtained from cell incubation on the ECM or plastic for 72 hrs after treatment with trypsin, and stained with the various primary antibodies and FITC-conjugated secondary antibodies. Cells stained with primary non-specific antibody (isotype, IgG) were serviced as negative control (gray-peaks). The stained cells were analyzed using Becton Dickinson FACStar$^{plus}$ flow cytometer with 10,000 events, collected for each sample. Initial: MNCs from UCB without culturing.

FIG. 19 illustrates an exemplary method for manufacturing a cell culture apparatus for maintaining or propagating MSCs in culture in an undifferentiated state using the preservation matrix.

Freshly isolated murine femoral marrow cells were seeded onto tissue culture plastic at $3 \times 10^5$ cells/$cm^2$, and cultured for seven days in co.-MEM (Life Technologies, Grand Island, N.Y.), supplemented with glutamine (2 mM), penicillin (100 U/ml), streptomycin (100 1.1 g/ml) (Sigma Chemical Company, St. Louis, Mo.), and 15% pre-selected fetal bovine serum (FBS, Atlanta Biologicals, Lawrenceville, Ga.). For preparation of skin fibroblasts, the ventral skin from 2-5 day old mice were removed, rinsed in PBS, and cut into 1-$mm^2$ pieces. The tissue was incubated with 400 U/ml collagenase for 40 minutes at 37° C., rinsed with PBS, and cultured in high glucose DMEM medium containing 10% FBS, glutamine (2 mM) and penicillin (100 U/ml) until primary fibroblasts migrated out of the samples onto the culture plates reaching 70% confluence. Fibroblasts were collected, and frozen for storage or used between passages two and six for the establishment of ECM.

To prepare preservation ECM, cells were seeded onto Thormanox plastic cover slips coated with fibronectin at $1 \times 10^4$ cells/$cm^2$, and cultured for seven days in the $\alpha$-MEM medium described above. Then ascorbic acid (50 ug/ml) (Sigma Chemical Company, St. Louis, Mo.) was added to the cell cultures for an additional eight days. After extensive washing with PBS, cells were removed from the ECM by incubation with 0.5% Triton X-100 containing 20 mM $NFI_4OFI$ in PBS for five minutes at 37° C. The ECM was then treated with DNase at 100 u/ml (Sigma Chemical Company, St. Louis, Mo.) for one hour at 37° C. The plates were washed with PBS three times, then 2.0 ml of PBS containing 50 ug/ml gentamicin and 0.25 ug/ml fungizone was added to the plates, and the plates were stored at 4° C. up to Ibur months.

Preparation of a Marrow Stromal Cell-Derived Preservation Matrix.

Scanning electron microscopy (SEM) revealed that stomal cells cultured from murine femoral bone marrow elaborated a fibrillar ECM (FIG. 1A). Prior to studying the behavior of MSCs on this nascent preservation ECM, the stromal cells were lysed with 0.5% Triton X-100 containing 20 mM $NH_4OH$ be allowed by DNase treatment to digest remaining nuclear contaminants (Gospodarowicz et al., 1984). The resulting 3D matrix contained fibers of approximately 25 nm diameter and was approximately 100 μm thick as determined by transmission electron microscopy (data not shown).

When examined prior to removal of stromal cells, immunostaining revealed high levels of collagen types I, III, V, syndecan-1, perlecan, fibronectin, laininin, biglycan and decorin associated with both stromal cells and the ECM (FIG. 1B). The protein composition of the preservation ECM was only modestly affected by the cell extraction procedure as indicated by retention of immunostaining for all of the proteins that were examined except for collagen type V (FIG. 1B).

Culture on Stromal Cell-Derived Preservation Matrix Facilitates Retention of MSC Properties.

The preservation ECM affects MSC adherence and proliferation. MSCs were detected and quantified by their ability to form a colony of fibroblastic cells (Sethe et al., 2006). These colony-forming cells, called colony forming unit-fibroblasts (CFU-F), comprise MSCs. After five days of culture, most of the cells in the colony were embedded inside of the collagenous matrix and exhibited a fibroblastic morphology with extensive cellular processes. In contrast, cells cultured on tissue culture plastic were round and flat (FIG. 18A).

When cultured on the stromal cell-derived preservation ECM, there was approximately a two to three fold increase in the number of CFU-F as compared to tissue culture plastic, demonstrating that the preservation ECM promoted MSC attachment (FIGS. 17B and 17C). 2D preservation ECM preparations, made by coating tissue culture plasticware with fibronectin or Type I collagen, were less effective (FIGS. 17B and 17C). Moreover, the colonies that developed on the stromal cell-derived preservation ECM contained approximately four-fold more cells than colonies that developed on plastic or fibronectin, whereas colonies formed on Type I collagen matrix contained only approximately twofold more cells than the colonies that developed on plastic or fibronectin (FIG. 17D). These findings indicate that a collagen containing preservation ECM uniquely promotes the proliferative capacity of MSCs and/or their transit amplifying progeny.

Cells in parallel cultures were detached by treating with 400 U/ml collagenase and the total number of cells well was counted using a hemocytometer. The mean number of cells per colony was estimated by dividing the number of cells per well by number of colonies per well.

The inventor further demonstrates that the marrow stromal cell-derived preservation ECM prevented "spontaneous" differentiation of MSCs. The 2D Type I collagen ECM, and a 3D skin fibroblast-derived differentiation ECM (SF-DECM) elaborated by skin fibroblasts obtained from neonatal mice were used as controls. The latter differentiation ECM exhibited a fibrillar structure similar to that of marrow stomal cell-derived preservation ECM (data not shown), consistent with the presence of type I and type III collagens. The proliferation of marrow cells placed on these matrices was similar, as determined by RNA content, and was increased as compared to cells cultured on plastic (FIG. 19A). When cultured on plastic for 20 days, cells were grouped into nodules whereas cells cultured on the collagen-containing ECM preparations were evenly distributed and exhibited a uniform morphology (FIG. 19B). The expression of the osteoblast markers alkaline phosphatase, col1a1, bone sialoprotein, and osteocalcin progressively increased during 25 days of culture (FIG. 19C), consistent with the "spontaneous" differentiation of MSCs reported previously (Baksh et al., 2004). In contrast, stromal cell-derived or skin fibroblast-derived ECM preparations prevented or delayed the appearance of these osteoblast markers. The 2D Type I collagen ECM also retarded osteoblastogenesis, but it was less effective. In a separate experiment, there was minimal mineral deposition, as determined by Von Kossa staining, when cells were maintained on the stromal cell-derived preservation ECM (data not shown).

The restraint of osteoblastogenesis seen in cultures of MSCs maintained on stromal cell-derived preservation ECM did not appear to be due to increased production of antagonists of the bone morphogenetic proteins (BMPs) and Wnt proteins needed for osteoblast differentiation. Specifically, the level of Sost, Noggin, Dkk 1, Chordin, Gremlin, and Twisted gastrulation transcripts in cultures maintained on this preservation ECM were equivalent to, or less than, that of cells cultured on plastic (FIG. 19D). A similar pattern was seen in the case of cells cultured on Type I collagen. On the other hand, transcripts of most of these antagonists were higher in cells cultured on the skin fibroblast-derived differentiation ECM, except for Gremlin 2 (FIG. 19D).

The marrow stromal cell-derived preservation ECM supported MSC function, whereas the differentiation ECM made by skin fibroblasts failed to support responsiveness to exogenous BMP2. The transcript levels of BMP and Wnt antagonists were increased in these cultures.

Autocrine/Paracrine Production of BMP2 Mediates the Osteoblastogenesis that Occurs when MSCs are Cultured on Plastic in the Presence of High Ascorbic Acid.

Hence, the restraint of osteoblast differentiation observed in cultures maintained on the stromal cell-derived preservation ECM could have been due to decreased synthesis of endogenous BMP2. The level of BMP2 transcripts, however, was similar to or higher in cultures maintained on the stromal cell-derived or skin fibroblast-derived ECM as compared to cells maintained on plastic (FIG. 20A), making this possibility unlikely. Murine bone marrow cell cultures were established on plastic or on the stromal cell-derived preservation ECM in 6-well plates. After 15 days, the supernatant was collected. BMP2 was extracted from the preservation ECM/cell layer using 2M urea, 2% SDS, 10% glycerol and 10 mM Tris-HCl pH 6.8. BMP2 in the supernatant and in the preservation ECM/cell layer extract was quantified by ELISA.

The cells maintained on the 2D type I collagen EM expressed low levels of BMP2 compared to the other cultures. A separate experiment demonstrated that the amount of BMP2 protein was increased approximately 2-fold in cultures maintained for 15 days on the stromal cell-derived preservation ECM as compared to plastic (FIG. 20B), and that >90% of BMP2 protein was associated with the cell/matrix in cultures maintained on the stromal cell-derived preservation ECM as compared to only 60% in the case of cultures maintained on the plastic. Thus, the restraint of osteoblast differentiation when MSCs were cultured on this preservation ECM is related to sequestration of BMP2 by the preservation ECM. Moreover, the expression of BMP2R1B transcripts was increased when cells were cultured on collagenous ECM as compared to plastic, indicating that lack of BMP2 receptor does not account for the poor responsiveness of cultures maintained on Type I collagen or skin fibroblast-derived differentiation ECM (data not shown).

Although MSCs did not undergo "spontaneous" osteoblastogenesis when cultured on the stromal cell-derived preservation ECM, they were capable of differentiating into osteoblasts in response to exogenous BMP2. When added 15 days after establishment of the cultures, as little as 3 ng/ml or as little as 10 ng/ml of BMP2 stimulated alkaline phosphatase activity and osteocalcin secretion (FIG. 20C). Consistent with the data of FIG. 19C, which shows an increase in alkaline phosphatase transcripts, basal alkaline phosphatase activity was elevated in cultures maintained on tissue culture plastic as compared to the preservation ECM. Addition of exogenous BMP2 to cells maintained on plastic modestly increased alkaline phosphatase activity, as well as osteocalcin secretion, but these effects required 10-fold higher concentrations than the cells cultured on the preservation ECM. BMP2 increased alkaline phosphatase activity, but not osteocalcin secretion, in MSCs maintained on the 2D Type I collagen ECM. MSCs failed to respond to exogenous BMP2 when cultured on skin fibroblast-derived differentiation ECM.

Murine bone marrow cell cultures were established either on plastic or plastic coated with a collagenous matrix including marrow stromal cell-derived preservation ECM, skin fibroblast-derived differentiation ECM or Type I collagen. After 15 days of culture, human recombinant BMP2 was added at the indicated concentrations. Alkaline phosphatase activity was determined after two days. Osteocalcin from conditioned medium was measured by RIA after six days.

Culture of MSCs on Stromal Cell-Derived Preservation Matrix Promotes Self-Renewal and Retention of Multipotentiality.

Figure 20A:
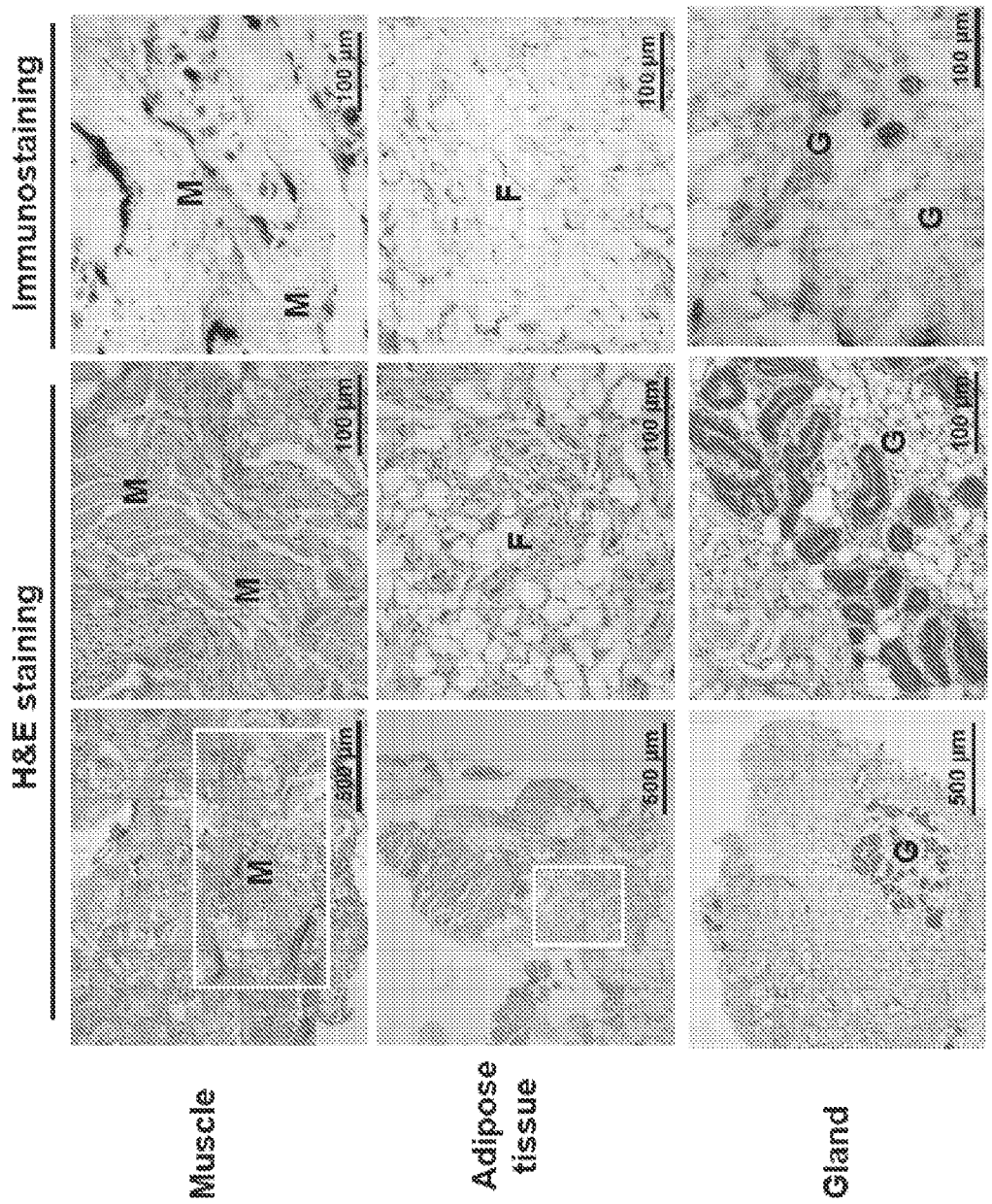
FIGS. 20A-B UCB-MSCs isolated by the ECM generated tissues originated from 3 embryonic germ layers in vivo. UCB-MSCs isolated by the ECM and continuously expanded on the ECM or UCB-MSCs isolated by plastic and continuously expanded on plastic were loaded onto Gelfoam or hydroxyapatite/tricalcium phosphate (HA/TCP) that favorably induces skeletogenesis, and implanted subcutaneously into the dorsal surface of 10-wk-old immunodeficient beige mice. Each vehicle was loaded with $0.5\times10^6$ cells. Three implantations were performed for each condition. Implants were harvested after 8 wks of implantation and processed for histological analysis. The sections were stained with H&E. In addition, Bielschowsky's silver staining was used to specifically identify nerve (see middle panel of Nerve fibers). To determine the origin of generated tissue, a section adjacent to the H&E stained section was stained with an antibody specifically against human nuclear ribonucleoprotein purchased from Millipore (Billerica, Mass.). Mouse and human tissues served as negative and positive controls, respectively. Skeletal tissue generated in ossicles has been defined as from donor origin. A, artery; B, bone; C, capillary; E, endothelial cells; F, fat; G, gland; M, muscle; and N, nerve.

The self-renewal of MSCs was determined using a replating assay in which the increase in colony forming cells following seven days of pre-culture of MSCs was quantified (Di Gregorio et al., 2001). Self-renewal of MSCs was measured for MSCs cultured on plastic, the 3D stromal cell-derived preservation ECM, or 3D Type I collagen gels that have been previously described (Abe et al., 2000). Differentiation ECM from skin fibroblasts was not examined as BMP2 responsiveness of MSCs was lost in such cultures. The number of CFU-F colonies was increased approximately 48-fold when the cells were precultured on stromal cell-derived preservation ECM as compared approximately 9-fold or approximately 27-fold in cultures maintained on plastic or Type I collagen gel, respectively (FIG. 20A). Self-renewal of MSCs. Murine bone marrow cells were cultured on plastic, or 3D Type I collagen gel, or the stromal cell-derived preservation ECM at $5 \times 10^6$ cells per 10 cm$^2$ well. Some of the bone marrow cells were used to determine the number of CFU-F, CFU-OB, and CFU-AD present in the initial isolate. After seven days of pre-culture, the adherent cells were detached and harvested with collagenase, and reseeded into tissue culture plastic for measuring CFU-F, CFU-OB and CFU-AD.

Similarly, the replication of colony-forming progenitors capable of differentiating into osteoblasts [CFU osteoblast (CFU-OB)] and/or adipocytes [CFU-adipocyte (CFU-AD)], was significantly higher when MSCs were pre-cultured on the stromal cell-derived preservation ECM, as compared to cells cultured on plastic or Type I collagen gel. Indeed, CFUOB did not significantly increase when pre-cultured on plastic, consistent with the evidence of FIG. 18C that MSCs divided and differentiated toward the osteoblast lineage, instead of dividing to produce identical colony-forming MSCs.

Figure 20B:
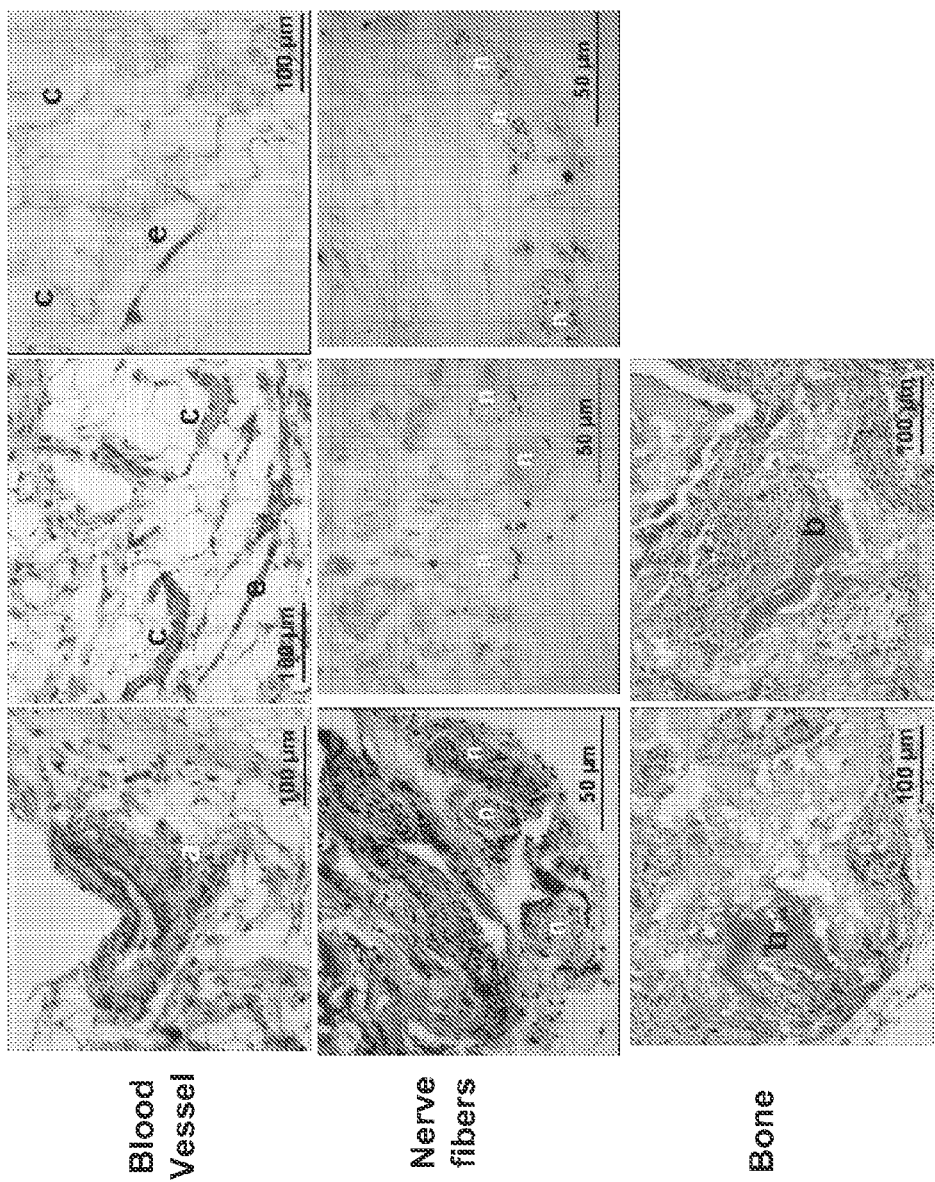

The proportion of CFU-OB and CFU-AD among the entire population of colony-forming MSCs (as detected by CFU-F) declined approximately 3-fold during expansion, from approximately 50% in the initial marrow cell isolate to approximately 15% after pre-culture on plastic, Type I collagen gel, or stromal cell-derived preservation ECM (FIGS. 20B and 20C). This may reflect the heterogeneity of the colony forming cells present in the initial isolate, and the fact that some of the progenitors in the CFU-F population divided more frequently than others during the pre-culture period.

Figure 21:
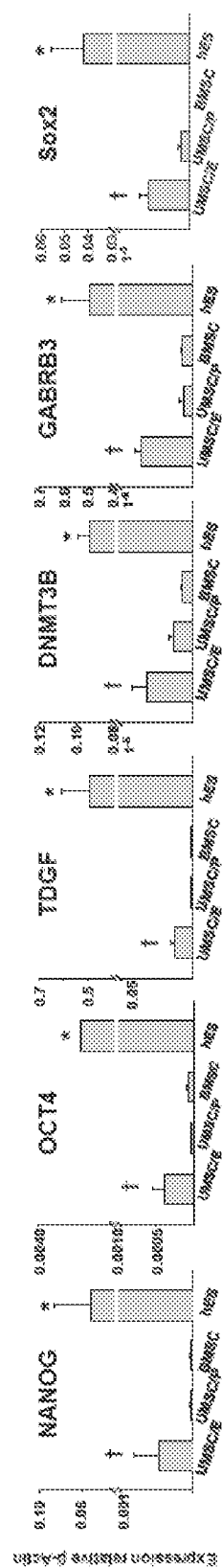
FIG. 21 Gene expression profiles of UCB cells isolated by the ECM adhesion method. RNA was prepared from UCB cells (passage 1) pre-isolated and maintained on the ECM (UMSC/E) or on plastic (UMSC/P) separately from 4 individual donors. The transcripts of interest were determined by real-time PCR using TaqMan PCR Master Mix and Assay Demand (Applied Biosystems). RNA isolated from human ES cells [(hES) cell line H7] was kindly provided by Dr. Christopher Navara from UTSA. RNA for human MSCs (BMSC) was prepared from human bone marrow cells purchased from ALLCELLS (Emeryville, Calif.) as described in Method. *$P<0.01$ (n=4), hES vs. UMSC/E, or UMSC/P, or BMSC. †$P<0.01$ (n=4) UMSC/E vs. UMSC/P, or BMSC.

In view of the likely heterogeneity of the colony forming cell population, the inventor compared the capacity of MSCs expanded on plastic or the stromal cell-derived preservation ECM to form bone and hematopoietic marrow in vivo using a transplantation assay.[19] Following seven days of culture on plastic or on stromal cell-derived F,CM, the cells were loaded onto a hydroxyapatite/tricalcium phosphate (HA/TCP) carrier and implanted subcutaneously into immunocompromised NIH-bg-nu-xid mice. The amount of bone generated at eight weeks after implantation by MSCs pre-cultured on plastic was approximately 3% of bone of the total area of the ossicle. However, there was minimal hematopoietic marrow, and adipocytes and osteoclasts were rarely observed (FIGS. 21A, 21B and 21E). Importantly, MSCs pre-cultured on stromal cell-derived preservation ECM generated approximately five times more bone than the cells pre-cultured on tissue culture plastic (FIGS. 21B through 21E), which corresponds with the approximately 5-fold greater increase in CFU-OB replication during pre-culture on the preservation ECM as compared to plastic (FIG. 20B).

Bone marrow cells were pre-cultured for seven days on plastic or the stromal cell-derived preservation ECM. The cells were then loaded onto HA/TCP and implanted subcutaneously into the dorsal surface of 10-week-old immunodeficient beige NIH-bg-nu-xid mice. Three transplants were made for each group. The transplants were harvested after four or eight weeks, fixed, decalcified and then processed for paraffin embedding.

Osteoclasts were also present in ossicles made by cells pre-cultured on the preservation ECM (FIG. 21D), indicating the presence of stromal cells that support osteoclast differentiation. Extensive hematopoietic marrow characterized by a large number of adipocytes was observed at 8, but not 4, weeks after implantation (FIG. 21C). The area of hematopoietic marrow was increased by 8-fold in ossicles made by cells cultured on the preservation ECM as compared to cells cultured on plastic (FIG. 21F). Each ossicle was bisected. Then, 10 um sections were cut from the bisection point of one portion at 100 um intervals for measurement of the mean bone area for each ossicle.

Primary human bone marrow mononuclear cells (hBMCs, purchased from AllCells, LLC.) were placed onto either the preservation ECM made by human marrow stromal cells (hMSC-ECM) or tissue culture plastic at various cell seeding densities (2, 1, and $0.5 \times 10^6$ cells per well). After 4 hours of incubation, the non-adherent cells were removed by rinsing with PBS once. Then the cells were cultured in a-MEM containing 15% FCS for 2 weeks.

Figure 22:
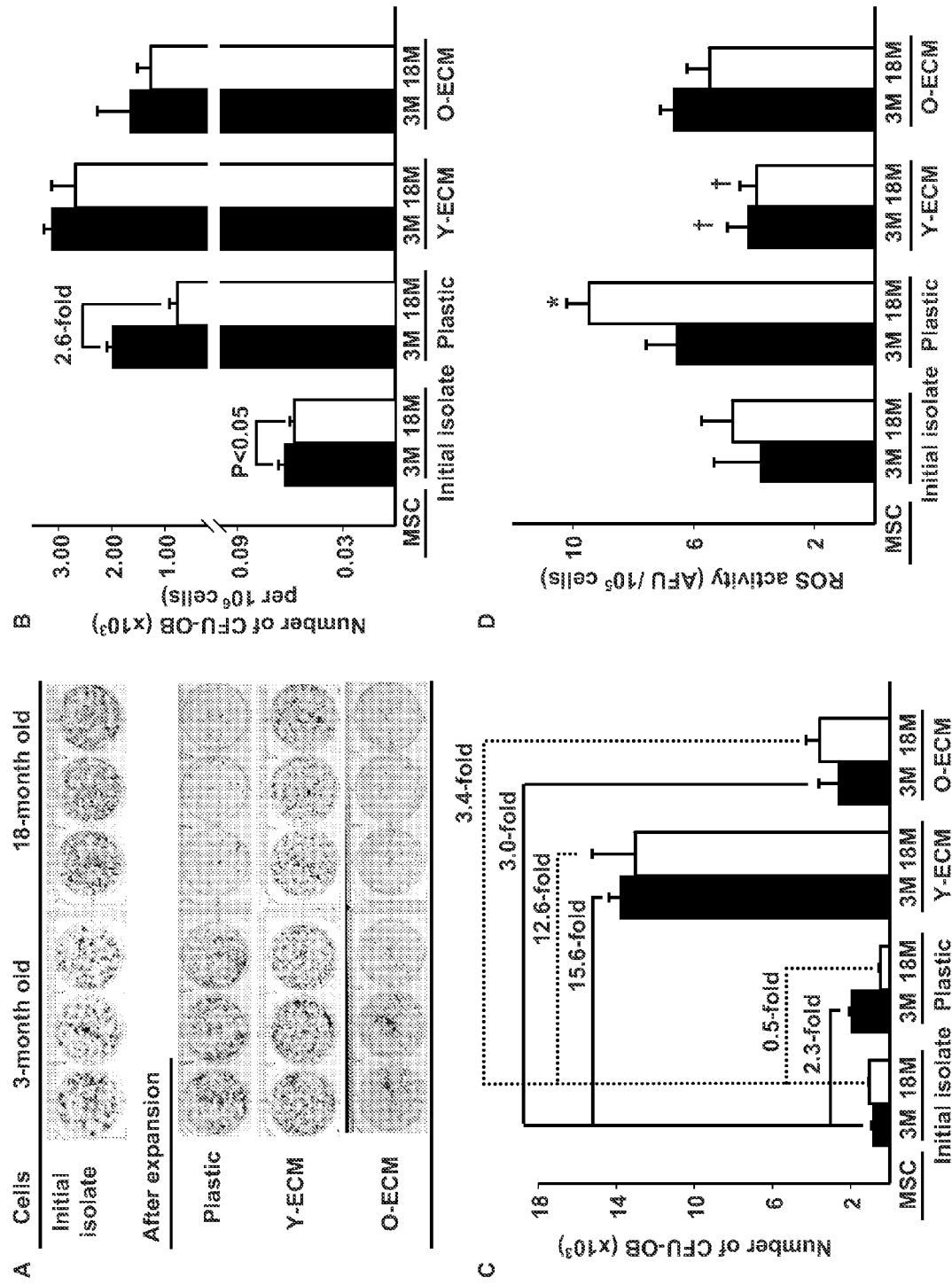
FIGS. 22A-D Correction of a defect in the replication of MSCs from old mice by exposure to an ECM made by marrow stromal cells from young mice. Aliquots of freshly isolated bone marrow cells from either 3-month (3M) or 18-month (18M) old mice were used to determine the numbers of CFU-OB in initial isolate, and portions of the remaining cells were seeded onto tissue culture plastic (Plastic), or tissue culture plastic coated with young-ECM (Y-ECM) or old-ECM (O-ECM). After 7 days of culture, adherent cells were detached from the various substrata, and then re-seeded on plastic separately for determination of CFU-OB by visualization with Von Kossa stain, which appears dark. The replication of CFU-OB was determined by comparing the number present in the initial femoral marrow cell isolate to the number present after 7 days of culture on the various matrices as described (Chen et al., 2007).

FIG. 22 illustrates preservation ECM made by human marrow stromal cells promotes colony forming unit-osteoblast (CFUOB) and colony forming unit-fibroblast (CFU-F) formation. CFU-F were visualized by crystal violet shown in blue (right panel). In addition, cells were cultured in osteogenic induction medium (a-MEM containing 15% FCS, 100 uM A2P, 10 mM β-glycerophosphate, and 10 nM dexamethasone) for 4 weeks, and then CFU-OB was determined by Von Kossa staining shown in black (left panel).

Figure 23:
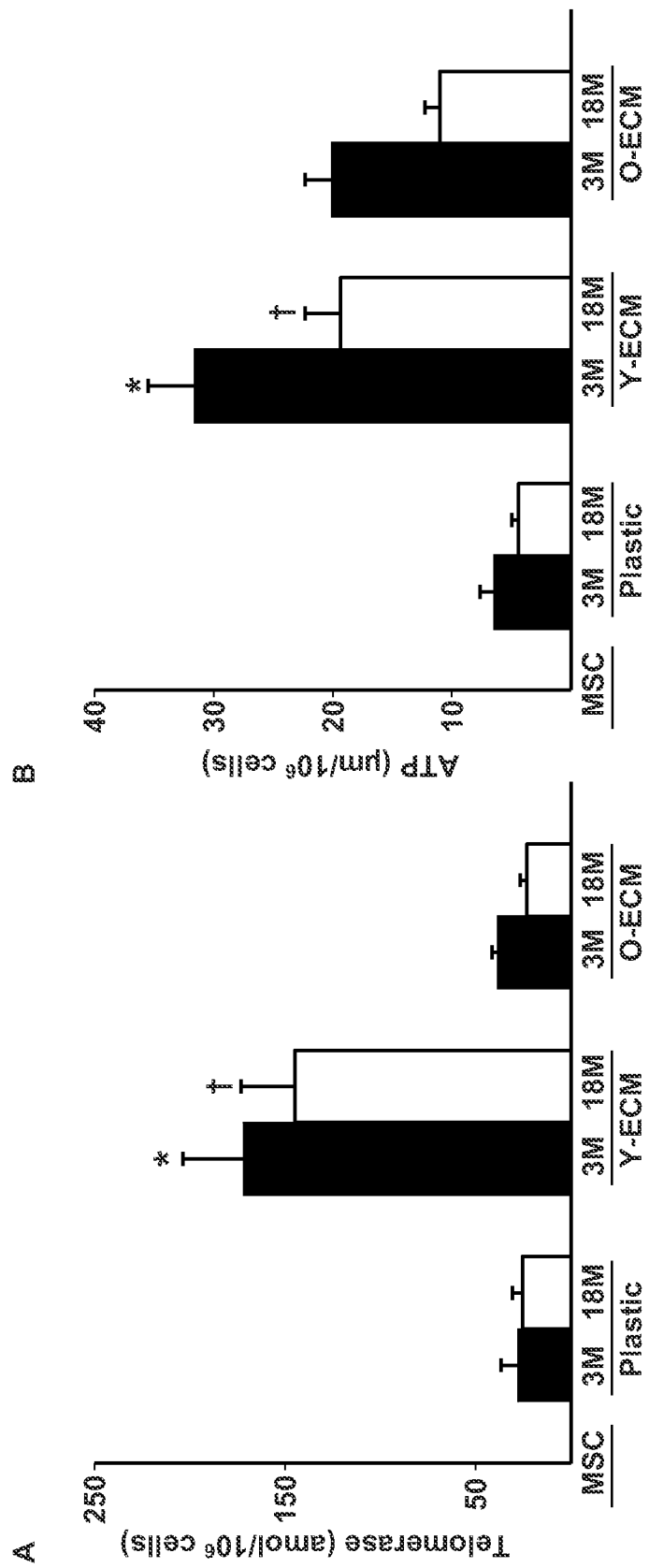
FIGS. 23A-B Bone marrow cells cultured on young-ECM increased the levels of intracellular telomerase and ATP. Freshly isolated bone marrow cells from either young (3M) or old mice (18M) were seeded onto tissue culture plastic (Plastic), young-ECM (Y-ECM) or old-ECM (O-ECM), and cultured for 7 days. After rinsing with PBS to remove nonadherent cells, adherent cells were detached with collagenase. Adherent bone marrow cells ($1 \times 10^6$) collected from the various substrates were used for the measurements of telomerase or ATP levels.

The colonies formed by cells cultured on the preservation ECM contained both osteoblasts as visualized by the deposition of mineral stained with Von Kossa (black), and adipocytes stained with Oil Red 0 (red). The colonies formed by cells cultured on tissue plastic contained less mineral content and fewer adipocytes. FIG. 23 illustrates microscopic appearance of CFU-OR.

Primary human bone marrow mononuclear cells (AllCells, LLC.) were pre-cultured for 14 days on tissue culture plastic or the human stromal cell-derived preservation ECM. The cells were then loaded onto a transplantation vehicle I hydroxyapatite/tricalcium phosphate (HA/TCP) particles] and implanted subcutaneously into the dorsal surface of 10 weeks old immunodeficient beige NIII-bg-nu-xid mice. The transplants were harvested after 8 weeks, fixed, decalcified and then processed for paraffin embedding.

Figure 24:
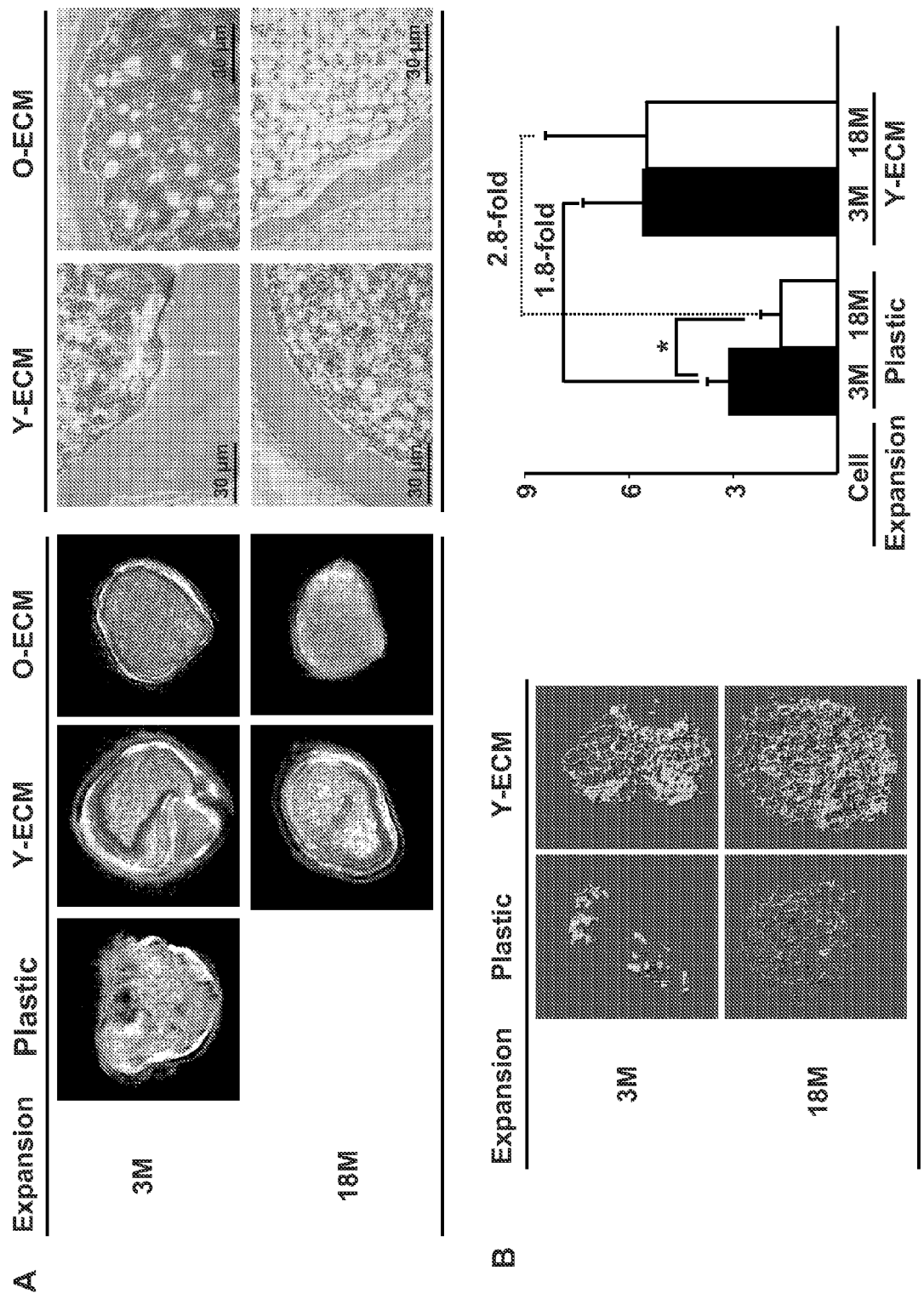

FIG. 24 illustrates bone formation in vivo by transplanted human MSCs. Bone was generated by cells pre-cultured on the preservation ECM (left panel). Bone was generated by cells pre-cultured on tissue culture plastic (right panel).

Figure 36C:
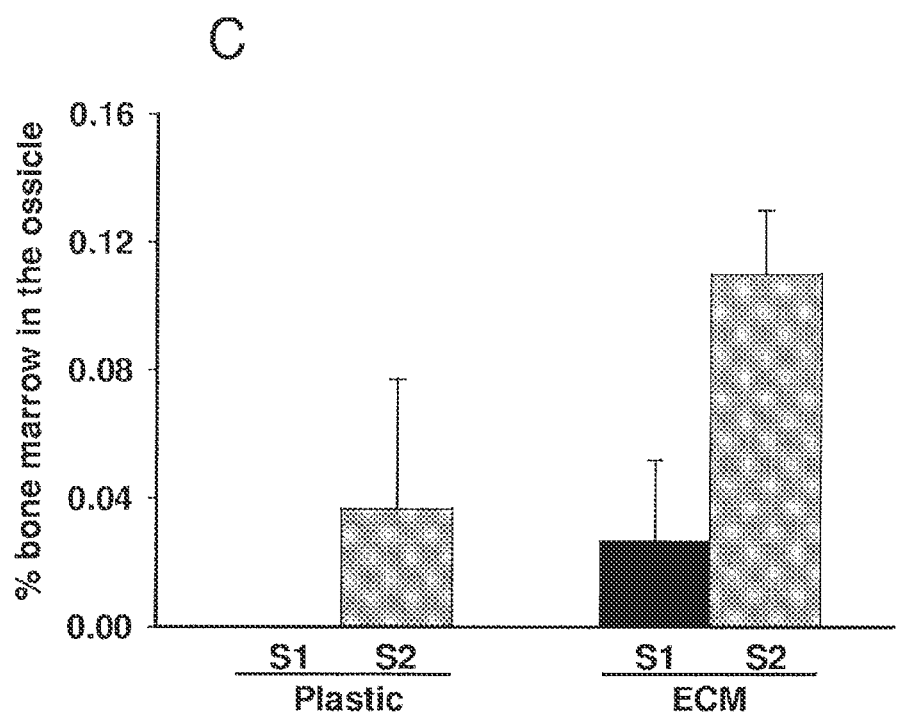

FIGS. 36A and B illustrate quantification of bone in ossicles. Each ossicle was bisected. Then, three 10 μm sections were cut from the center part at 100 μm intervals. FIG. 36A shows the measurements of bone area from 3 individual sections for each sample (S1 or S2). FIG. 36B shows the mean bone area calculated from 3 individual sections for each sample (S1 or S2). FIG. 36C illustrates quantification of bone marrow in ossicles with mean bone marrow (hematopoietic tissue) calculated from 3 individual sections for each sample.

Example 3

Preparation and Characterization of the Preservation Matrix

Materials and Methods
Cells.

Freshly isolated human bone marrow mononuclear cells obtained from 20-30 year old donors were purchased from ALLCELLS (Emeryville, Calif., USA), and grown on tissue culture plastic at an initial seeding of $3\times10^5$ cells/cm² until 70% confluence (2-3 weeks) in the expansion medium [a-MEM (Life Technologies, Grand Island, N.Y., USA), glutamine (2 mM), penicillin (100 U/ml), streptomycin (100 pg/ml, Biofluids, Rockville, Md., USA), and 15% preselected fetal bovine serum (FBS, Becton Dickinson, Franklin Lakes, N.J., USA)]. After washing with phosphate-buffered saline (PBS) to remove non-adherent cells, the adherent cells, considered as passage 1, were detached by trypsin treatment (0.02% for 2 minutes at 37° C.), and collected for storage or directly used for the establishment of preservation ECM or the investigation of the behavior of MSCs maintained on the various substrata.

Preparation of Cell-Free Preservation ECM from Cultured Bone Marrow Cells, and Tissue Culture Plates Coated with Fibronectin or Collagen Type I.

A standard procedure based on the previous studies was utilized (Chen et al., 2007). Cells from passages 1 or 2 were seeded onto tissue culture plastic at $1\times10^4$ cells/cm², and cultured for 15 days. The medium was changed every 3-4 days, and ascorbic acid (50 μM) was added during the final 8 days of culture. After extensive washing with PBS, cells were removed by incubation with 0.5% Triton X-100 containing 20 mM $NH_4OH$ in PBS for 5 minutes at room temperature. After washing with PBS 4 times, PBS containing 50 μg/ml gentamicin and 0.25 μg/ml fungizone was added to the plates, which were stored at 4° C. for up to 4 months. Tissue culture plates coated with fibronectin or collagen type I were prepared as previously described (Cukierman et al., 2001).

Scanning Electron Microscopy (SEM).

Cultures seeded onto coverslips coated with or without the preservation ECM were washed 3 times with PBS and fixed with 2% glutaraldehyde in 0.1M sodium cacodylate buffer (pH 7.2) for 1 h and then transferred to 0.1 M cacodylate buffer solution. The specimens were dehydrated in ascending concentrations of ethanol (from 70% to 100%). After dehydration, the coverslips were attached to a stub and sputtered with gold-palladium. The specimens were examined using an EVO-50EP SEM manufactured by Carl-Zeiss SMT.

Immunohistochemistry.

Stromal cell-derived preservation ECM was fixed for 30 min with 4% formaldehyde in PBS at room temperature, washed with PBS, and blocked with 5% normal goat serum containing 0.1% BSA in PBS for 1 hour. The matrices were then incubated with the relevant primary antibodies (1:10 dilution, Santa Cruz Biotechnology, Santa Cruz, Calif., USA) in 2% goat serum for 2 hours. Non-specific isotype IgG (1:10 dilution) was used as a negative control. After washing with PBS, samples were incubated with the appropriate FITC-conjugated second antibody and washed. Specimens were mounted using DAPI containing mounting medium (Vector Laboratories, Burlingame, Calif., USA), and visualized using a FV500 Fluoview Confocal Microscope equipped with image analysis software to quantify fluorescence intensity in a given region of interest.

Determination of Colony-Forming Unit Fibroblasts (CFU-F), Osteoblasts (CFU-OB), and Adipocytes (CFU-AD).

Freshly isolated human bone marrow mononuclear cells obtained from 20-30 year old donors were plated into 6-well plates uncoated or coated with the indicated matrices at $3\times10^4$ cells/cm², incubated for 4 hrs at 37° C., and washed twice with PBS to remove non-adherent cells. Then, the cells were cultured to generate CFU-F colonies in the expansion medium. After 14 days of culture, CFU-F colonies were visualized with crystal violet staining To assess CFU-OB colony formation, CFU-F colonies were maintained for an additional 25 days in osteoblast differentiation medium [expansion medium supplemented with $10^{-7}M$ dexamethasone (Sigma) and $10^{-4}M$ L-ascorbate-2-phosphate (Wako Chemicals, Richmond, Va.)]. The CFU-OB colonies were detected by von Kossa staining To assess CFU-AD colony formation, CFU-F colonies were maintained for an additional 10 days in adipogenic medium (DMEM containing 10% FBS, 0.5 mM IBMX, $10^{-6}M$ dexamethasone, 10 μM insulin, 200 μM indomethacin) (Zuk et al., 2001). CFUAD colonies were visualized with Oil Red O staining. Average size and intensity of CFU-F and CFU-AD colonies were quantified using the NIH ImageJ program. Osteocalcin secretion in the supernatant collected from the primary CFU-OB assay before von Kossa staining was measured using Metra Osteocalcin EIA kit (QUIDEL Corporation, San Diego, Calif., USA) following the manufacturer's instructions. MSC self-renewal was determined by the replication assay as described previously (Chen et al., 2007; De Gregorio et al., 2001). Basically, MSCs were sub-cultured on preservation ECM or plastic for serial passages, and colony assay was performed separately on plastic following each passage. Since freshly isolated human bone marrow cells maintained on the preservation ECM proliferated considerable faster (~10 days for the cells reached to confluence) than those grown on plastic (~20 days for the cells reached to confluence), comparative replication assays could not be carried out at the same time following the primary culture. Thus, the inventor used the pre-cultured cells on plastic (passage 2 or 3) as the starting cell population. Aliquots ($2\times10^5$ cells) of passage 3 (P3) human bone marrow cells, which the inventor also used to determine the initial numbers of CFUs including CFU-F, CFU-AD, and CFU-OB, were seeded onto 100 mm plastic or plastic coated with the preservation ECM. After 7 days of culture (70-90% confluent, P4), the cells were detached from the various substrata, counted, and then re-seeded on plastic separately for determination of CFUs. The remaining P4 cells were replated onto 100 mm plastic or plastic coated with the preservation ECM at the same starting density of 2×10⁵ cells. After 7 days of culture (P5), the cells were detached and CFUs determined. Subsequent serial passages were obtained by repeating the same procedure as with P4. The number of CFUs following each passage was determined as previously described (Chen et al., 2007. MSC replication was expressed by the fold change in CFUs during the expansion [total number of CFUs obtained from P(n) divided by total number of CFUs obtained from P(n−1), where n is the number of passages].

Flow Cytometry.

Single-cell suspensions (1-2×10⁶) were incubated in 100 ml of diluted antiSSEA-4 antibodies (10 pg/ml) (R&D Systems, Minneapolis, Minn., USA) for 30 minutes at 4° C. The stained cells were washed twice in staining buffer (PBS containing 5% FCS and 0.01% sodium azide) and incubated in 20 pg/ml of FITC-conjugated goat anti-mouse IgG for 20 minutes at 4° C. The cells were then washed twice with staining buffer and either immediately analyzed or fixed with 1% paraformaldehyde in PBS and analyzed within 96 hours using a Becton Dickinson FACStarPlus flow cytometer with 10,000 events, collected for each sample and the percentage of positively stained cells determined from fluorescence-activated cell sorting (FACS). Cells were stained with isotype IgG as a negative control. To access MSCs enriched in SSEA-4⁺ cell population, both SSEA-4⁺ and SSEA-4⁻ cells were sorted separately from primary human bone marrow cell culture.

Measurements of Intracellular Reactive Oxygen Species (ROS) and Telomerase Activity.

Intracellular ROS generation was measured with 2',7'-dichlorodihydrofluorescein diacetate (H2DCFDA) using a ROS Assay Kit (Invitrogen, Eugene, Oreg., USA) following the manufacturer's recommendations. ROS levels were expressed as arbitrary units (AU) of DCF fluorescence per 10⁵ cells. Telomerase activity was measured using the quantitative telomerase detection kit (Allied Biotech, Inc., Twinsburg, Ohio, USA) according to manufacturer's instructions. A breast cancer cell line (MDA231) served as a positive control and human red blood cells were used as a negative control. Experiments were performed in triplicate, and telomerase levels were expressed as amoles per 2×10⁵ cells.

Quantification of Osteocalcin and Bone Sialoprotein Gene Expression in Response to BMP-2.

Human bone marrow cells (passage 2) were cultured on plastic with or without the preservation ECM in the expansion medium for 10 days, and then cultured in osteoblast differentiation medium with 2% FBS overnight and treated with BMP-2 in various doses for 3 days. Total RNA was extracted and reverse-transcribed using a High Capacity cDNA Archive Kit (Applied Biosystems, Foster City, Calif.). The transcripts of interest were amplified from cDNA by real-time PCR using TaqMan Universal PCR Master Mix and Assay Demand or Assay by Design primer and probe sets (Applied Biosystems, Foster City, Calif., USA). Amplification and detection were carried out with an ABI 7500 Real Time PCR System (Applied Biosystems). Gene expression was quantified by subtracting the GAPDH threshold cycle (Ct) value from the Ct value of the gene of interest, and expressed as $2^{-\Delta ct}$.

Microarray and Data Analysis.

SSEA-4⁺ cells were isolated from primary human bone marrow cell culture using FACS sorting and cultured separately on plastic or the preservation ECM in the expansion medium (a-MEM containing 15% FCS) for 12 days. The total RNA was isolated using Ultraspec™ RNA (Biotecx, Houston, Tex.) according to the manufacturer's protocol. RNA was quantitated by measuring ultraviolet absorption at 260 nm and adjusted to 1 pg/pl with RNAse-free water.

In this experiment, RNA samples were collected separately from the cultured cells obtained from 15 different donors (20-30 year-old) purchased from ALLCELLS (Emeryville, Calif.). The inventor used the "subpooling" approach whereby 3 subsets of RNA samples within each "Plastic" or "ECM" group were made, each subset comprising RNA pooled from 5 individuals for subsequent hybridization on one chip. This pooling strategy effectively normalizes inter-individual noise while still retaining enough statistical power to identify most genes whose expression has changed during expansion of MSCs on the preservation ECM versus plastic (Bakay et al., 2002; Peng et. al., 2003).

After pooling, RNA was sent to Genome Explorations (available on the world wide web at qenomeexplorations.com). There, RNA was converted to DNA and the labeled cRNA was prepared, which were hybridized onto Affymetrix Human Genome U133 Plus 2.0 chips. The chips were scanned, and data were pre-analyzed using Affymetrix MAS 5.0. Gene expression levels on "Plastic" chips (Plastic-A, Plastic-B, and Plastic-C) were compared with levels on "ECM" chips (ECM-A, ECM-B, and ECM-C) to determine expression differences between "Plastic" and "ECM" groups using the statistical program Significance Analysis of Microarrays (SAM) at a false discovery rate of 1%.

After pre-selecting genes with differential expression, advanced analysis including hierarchical clustering, functional classification, and reconstruction of biological pathways were performed using the software GeneSpring™ from Silicon Genetics (Redwood City, Calif.), and Gene Ontology (GO), a public database (Holmes and Brown, 2004). The genes highly associated with the functional groups were determined by Fisher's Exact Test (Manoli et al., 2006), and then organized into virtual pathways using PathwayAssist 3.0 (available on the world wide web at.ariadne-qenomics.com) based on literature references. In order to further demonstrate the similarity with all published stem cell gene expression profiles, Gene Set Enrichment Analysis (GSEA) was used to examine a variety of data sets from the NCBI GEO database that are enriched with the same genes as expressed in the MSC gene set (Sweet-Cordero et al., 2005; Yang et al., 2009).

In Vivo Bone Formation.

Human bone marrow cells were cultured for 7 days on plastic or preservation ECM for 10 passages. Following each passage, the cells (1×10⁶) were loaded into a transplantation vehicle [hydroxyapatite/tricalcium phosphate (HA/TCP) ceramic powder (Zimmer Inc, Warsaw, Ind., USA), or Gelfoam (Pfizer, N.Y., USA)] and transplanted subcutaneously into the dorsal surface of 10-week-old immunodeficient beige mice (NIH-bg-nu-xid, Harlan Sprague Dawley, Indianapolis, Ind., USA), as previously described (Bi et al., 2005). Three transplants were made for each pre-culture system, harvested after 8 weeks, fixed in 10% phosphate buffered formalin at 4° C. for 24 hrs, decalcified with 10% EDTA (pH8.0) at room temperature for 1-2 weeks, and then embedded in paraffin. Each ossicle was bisected, and each half sectioned at 10 pm thickness at 100 pm intervals. A total of 9 hematoxylin-eosin (H&E) stained sections were used for quantification. The extent of new bone formation in the implants was histomorphometrically determined as areas measured by using ImageJ analysis software (NIH Image).

Statistical Analysis.

All data are presented as mean±standard deviation calculated, with n=3 or 6, depending on the experiments. Statistical analyses were done by using Student's t test or one-way ANOVA with significance at P<0.05. All the results were reproduced in at least 3 independent experiments.

Results

Preparation of a Marrow Stromal Cell-Derived Preservation ECM.

Scanning electron microscopy (SEM) revealed that stromal cells cultured from human bone marrow elaborated a fibrillar ECM (FIG. 7A). The effect of cell extraction on specific components of ECM was examined by comparing the localization of collagen types I and III, fibronectin, biglycan, decorin, perlecan, and laminin in the marrow cell-derived preservation ECM before and after cell extraction using immuno-confocal microscopy for semi-quantitative visualization (FIG. 7B). These proteins were selected because of their importance in mediating growth factors binding to the ECM and possible role in controlling MSC behavior. Collagen types I and III clearly showed a directional alignment and orientation, different from other ECM components examined, which exhibited a random distribution. Interestingly, the preservation ECM made by the cultured stromal cells contained an abundant amount of laminin, a major component of basement membrane. Confocal microscopic analysis indicated that the ECM was approximately 20 μm thick (data not shown). Cells (blue) were absent following extraction, but the protein composition of the ECM was well preserved as indicated by retention of immunostaining for all of the proteins examined.

Marrow Stromal Cell-Derived Preservation ECM Enhances Colony Formation of Human MSCs.

MSCs were detected and quantified by their ability to form a colony of fibroblastic cells (Fuchs et al., 2004). These colony-forming cells, termed colony forming unit-fibroblasts (CFU-F), are comprised of MSCs as well as the transit amplifying progeny of MSCs (Di Gregorio et al., 2001). The ability of MSCs to differentiate into adipocytes or osteoblasts in response to specific differentiation medium was examined by measuring CFUadipocytes (CFU-AD) and CFU-osteoblasts (CFU-OB), respectively. When cultured on marrow stromal cell-derived preservation ECM, MSCs developed larger and denser CFU-F, CFU-AD, and CFU-OB than those cultured on tissue culture plastic, or plastic pre-coated with fibronectin or collagen type I (FIG. 8A). Microscopic analysis revealed that CFU-F, CFU-AD and CFU-OB on the preservation ECM contained more methyl violet-stained fibroblast-like cells, more Oil red O-stained adipocytes (shown in red), and more von Kossa staining for mineral (shown in dark), respectively, as compared to those on plastic (FIG. 8B). ImageJ-based histomorphometry was used to estimate the average size (number of pixels) and density (pixel intensity) of CFU-F and CFU-AD, and osteocalcin secretion in medium was measured for CFU-OB. Two- to 4-fold increases were seen in the size and density of CFU-F and CFU-AD cultures on the preservation ECM, as compared to the other matrices (FIG. 8C, left and middle panels). Osteocalcin protein secreted by CFU-OB cultured on the preservation ECM or on collagen type I coated plastic was ~4-fold greater than those cultured on the uncoated or fibronectin coated plastic (FIG. 8C, right panel). However, there was no significant difference in the levels of osteocalcin produced by CFU-OB developed on the preservation ECM versus collagen type I coated plastic.

Marrow Stromal Cell-Derived Preservation ECM Promotes Human MSC Proliferation and Suppresses Reactive Oxygen Species (ROS).

Human bone marrow cells (passage 2) were seeded onto plastic with or without preservation ECM, or onto plastic coated with fibronectin or collagen type I at ~5,000 cells/cm2, and maintained in the expansion medium for up to 14 days. The proportion of human MSCs in the cultures after 3, 7 10 and 14 days was determined by flow cytometric analysis, on the basis of positive staining for SSEA-4 (Stage-specific Embryonic Antigen-4), which was originally identified as an early embryonic glycolipid antigen (Kannagi et al., 1983), but also shown to identify human MSCs from bone marrow (Gang et al., 2007). The inventor found that the percentage of SSEA-4+ cells progressively decreased during 14 days of culture on plastic, and on plastic coated with either fibronectin or collagen type I (FIG. 9A). In contrast, the preservation ECM retained 70-82% of SSEA-4+ cells during the entire 14 days of culture. The number of cells grown on plastic, or plastic coated with either fibronectin or collagen type I, reached a plateau at day 10, while the number of cells grown on preservation ECM continued to increase during 14 days of culture (FIG. 9B, left panel). More importantly, the increase in the number of SSEA-4+ cells was approximately 7- to 10-fold more when cells were cultured on preservation ECM than on other substrata at day 14 of cultures (FIG. 9B, middle panel). Strikingly, the intracellular level of reactive oxygen species (ROS) was significantly lower in cells maintained on preservation ECM than in cells maintained on other substrata (FIG. 9B, right panel).

Figure 9C:
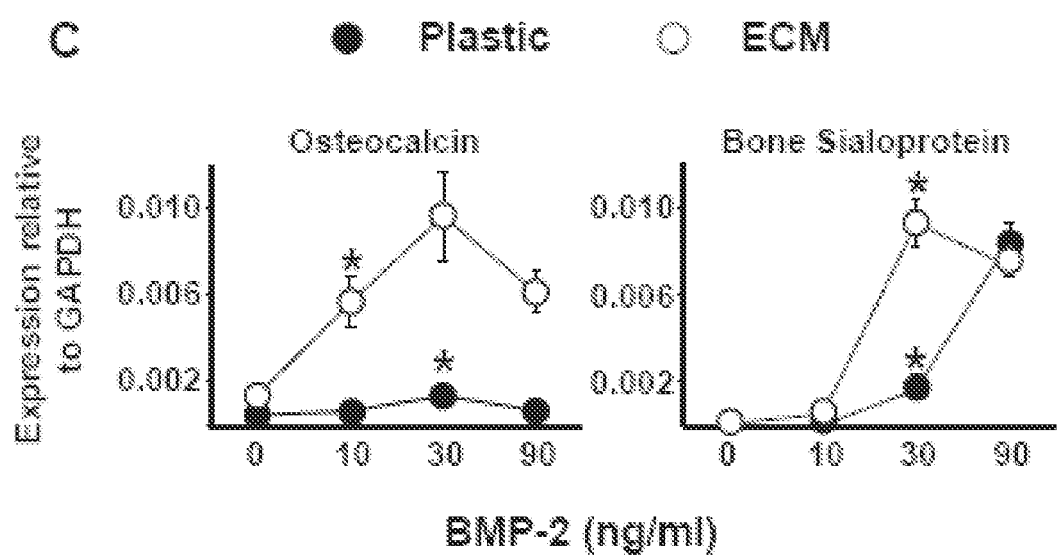
(FIG. 9C) Enhanced BMP-2 responsiveness of MSCs cultured on ECM. Cells were cultured on ECM or uncoated plastic (Plastic) or plastic coated with fibronectin (Fn) or collagen type I (Col. I) in the expansion medium for 10 days, and then cultured in osteoblast differentiation medium with 2% FBS overnight and then treated for 3 days with varying doses of BMP-2, as indicated. Gene expression of osteocalcin and bone sialoprotein was determined by quantitative RT-PCR (TaqMan). NI=3; *P<0.05, value at the lowest dose needed for the stimulation vs. vehicle control.

The inventor next examined whether cells grown on preservation ECM retained their osteoblastogenic response to BMP-2 stimulation. BMP-2 was added at day 10 of culture when preservation ECM and plastic with or without pre-coating fibronectin or collagen type I retained ~80% or ~24% of SSEA-4+ cells, respectively (FIG. 9A). The cells on the preservation ECM required as little as 10 ng/ml BMP-2 to stimulate osteocalcin expression with a ~5-fold increase, reaching a peak with a ~25-fold increase when the dose was increased to 30 ng/ml (FIG. 9C). In contrast, the cells cultured on plastic or plastic coated with fibronectin or collagen type I required 30 ng/ml BMP-2 to stimulate osteocalcin expression, exhibiting a small peak with a ~5- to 10-fold increase (FIG. 9C). The patterns of bone sialoprotein expression in response to BMP-2 were very similar to those of osteocalcin when cells were maintained on the preservation ECM versus plastic or plastic coated with fibronectin or collagen type I. The levels of bone sialoprotein expressed by cells maintained on the preservation ECM were-6- to 8-fold higher than those maintained on plastic as well as plastic coated with fibronectin or collagen type I when treated with 30 ng/ml BMP-2 (FIG. 9C).

Marrow Stromal Cell-Derived Preservation ECM Retains SSEA-4$^+$ Cells and Enrich Colony-Forming Cells.

Figure 10:
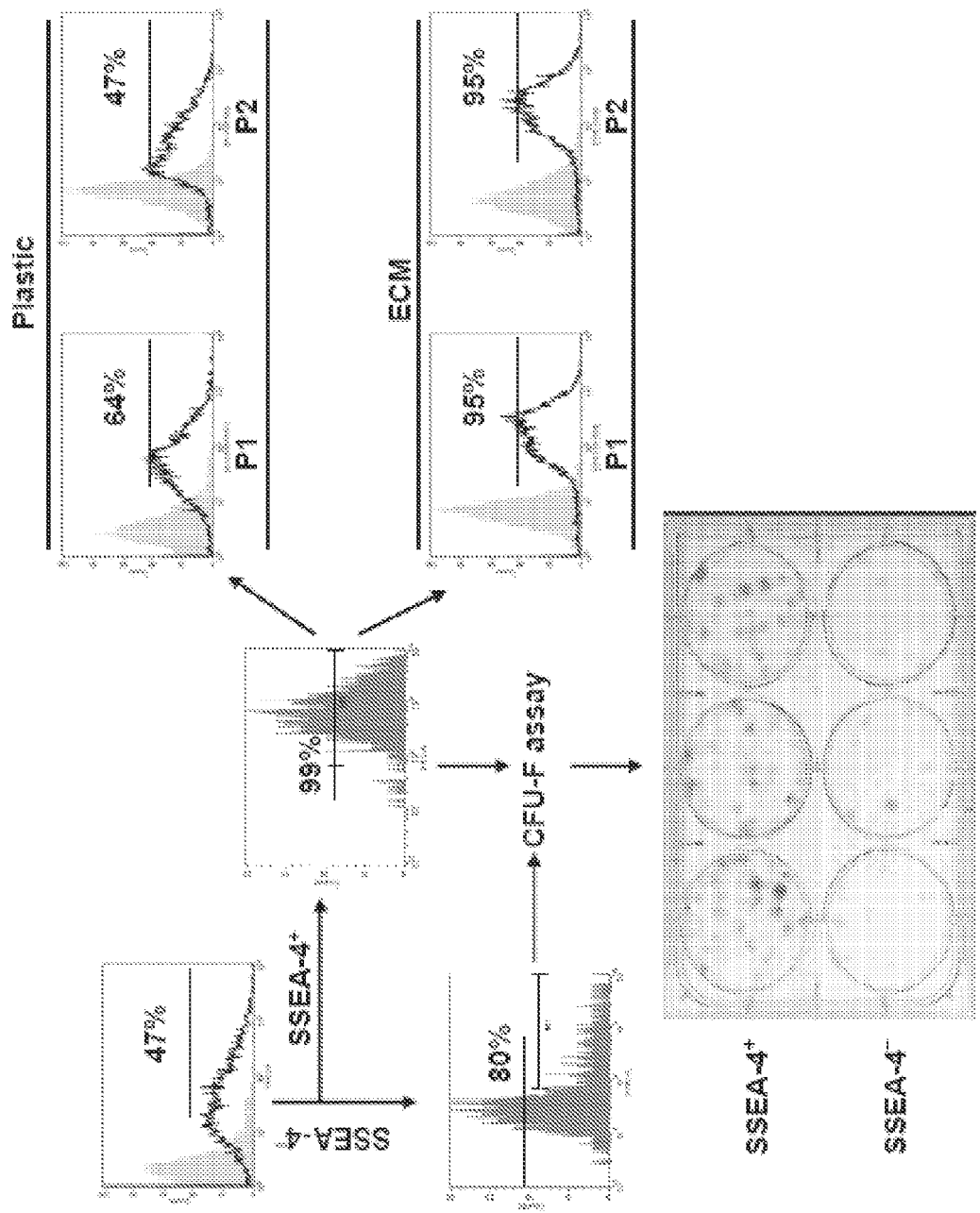
FIG. 10 Marrow Stromal Cell-derived ECM Retains SSEA-4$^+$ Cells and Enriches Colony Forming Cells. Freshly isolated human bone marrow mononuclear cells were cultured on tissue culture plastic at an initial seeding $3 \times 10^5$ cells/cm$^2$ until 70% confluence (2-3 weeks) in the expansion medium. After removal of non-adherent cells, the cultured bone marrow adherent cells were detached and stained with a specific antibody against SSEA-4. SSEA-4$^+$ cells and SSEA-4$^-$ cells were sorted using FACS. CFU-F assay was performed to determine the frequency of CFU-F in the sorted SSEA-4$^+$ and SSEA-4$^-$ cell populations. In addition, SSEA-4$^+$ cells were subcultured on either ECM or tissue culture plastic (Plastic) for 2 passages (P1 and P2). SSEA-4 expression was analyzed by FACS following each passage. For a negative control (gray-peak), cells were stained with primary non-specific antibody (isotype). Simultaneously, the sorted SSEA-4$^+$ or SSEA-4$^-$ cells were placed onto tissue culture plastic at 300 cells per well (10 cm$^2$ area) in triplicate and cultured for 14 days in 3 ml α-MEM containing 15% FBS. CFU-F colonies were then visualized with crystal violet staining.
Figure 13:
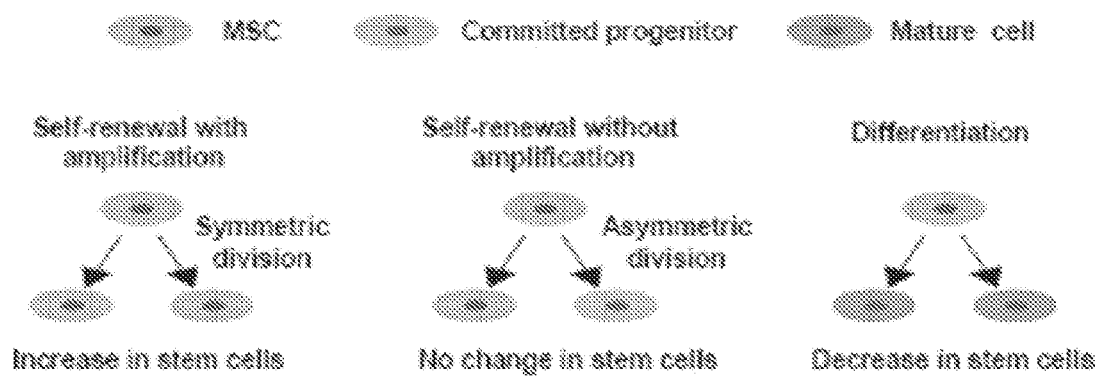
FIG. 13 Potential fates of mesenchymal stem cells (MSCs). MSCs are indicated in green, committed progenitors are indicated in pink, and the mature cells are fully differentiated and are shown in red.
Figure 14:
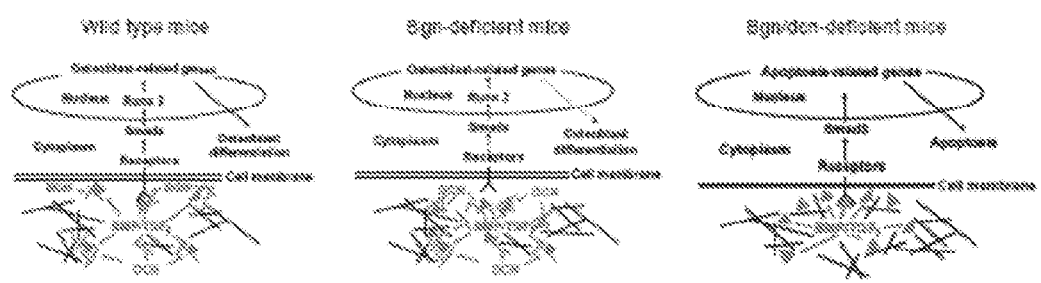
FIG. 14 Model of biglycan (bgn) and decorin (dcn) modulation of BMP and TGF-b to control the fate of MSCs. bgn and dcn normally compete to bind BMPs and TGF-b, thus regulating the exposure of these growth factors to the target cells (left diagram). When bgn is absent (bgn-deficient mice), BMP and TGF-β availability may be reduced because of increased expression and/or altered distribution of dcn (middle diagram). As a result of reduced autocrine/paracrine growth factor signaling, osteoblastic differentiation is impaired, judged by expression and activation of Runx2. When both bgn and dcn are absent (bgn/dcn-deficient mice), higher levels of free BMPs and TGF-β availability may initiate an apoptosis pathway, leading to cell death (right diagram).

To further access MSCs enriched in SSEA-4$^+$ cell population, the inventor sorted both SSEA-4$^+$ cells and SSEA-4$^-$ cells from primary human bone marrow cell culture using FACS. In this case, over 99% positive cells, and 80% negative cells were obtained separately (FIG. 10). Then CFU-F assays were performed to determine the frequency of CFU-F in both the SSEA-4$^+$ cell population and the SSEA-4$^-$ cell population. The results suggested that the number of CFU-F in the SSEA-4$^+$ cell population was at least 5- to 6-fold greater than that in the SSEA-4$^-$ cell population. A few of the CFU-F shown in the SSEA-4$^-$ cell population could have been generated from contaminated SSEA-4$^+$ cells (the sorted SSEA-4⁻ cell population contained ~20% SSEA⁺ cells). To identify how SSEA-4⁺ cells were retained on preservation ECM versus tissue culture plastic (Plastic), the inventor cultured the purified SSEA-4⁺ cells on either preservation ECM or tissue culture plastic up to 2 passages, and then analyzed SSEA-4⁺ cells by FACS following each passage. It was found that preservation ECM retained ~95% SSEA-4⁺ cells, whereas SSEA-4⁺ cells maintained on plastic dropped to ~50% over 2 passages (FIG. 10). However, the majority of SSEA-4⁻ cells failed to grow on either preservation ECM or plastic, which was consistent with the previous observation reported by Gang et al. (2007).

A Gene Expression Signature of Human MSCs Maintained on the Preservation ECM.

To comprehensively demonstrate how different are MSCs maintained on preservation ECM versus plastic, the inventor compared global patterns of gene expression in human MSCs (pre-purified SSEA-4⁺ cells) cultured on plastic (Plastic) versus on stromal cell derived-ECM (ECM) in the expansion medium for 12 days. The inventor identified 1741 transcripts either up- or down-regulated in cells cultured on preservation ECM versus on plastic using the statistical program Significance Analysis of Microarrays (SAM) at a false discovery rate of 1% (FIG. 11A). Then, 1741 transcripts were classified based on their biological function using the Gene Ontology (GO) database. Strikingly, based on the lowest p-value, the top 3 clusters mapped by these 1741 genes were associated with cell division (cell cycle), chromosome part, and cell movement (cytoskeleton), respectively (Table 4). Furthermore, 721 up-regulated transcripts were separated from the 1741 transcripts, and analyzed for statistically significant enrichment of human MSCs gene expression pattern [datasetsGSE10315 (available on the world wide web at ncbi.nlm.nih.qov/qeo/querv/acc.cqi?acc=GSE10 315)] found in public gene sets from the NCBI GEO database using the software Gene Set Enrichment Analysis (GSEA), as previously described (Yang et al., 2009). FIG. 11B shows that this 721 gene set was highly enriched in genes related to undifferentiated human MSCs with a Normalized Enrichment Score (NES) of 1.76 and a Family Wise-error Rate (FWER) p-value of 0.016, as compared to human MSCs treated with BMP-2. This strongly suggested that the genes expressed by cells maintained on the preservation ECM were most likely the undifferentiated MSC gene set when compared with differentiated MSCs induced by BMP-2 treatment. The inventor was not able to examine gene expression profiles of SSEA-4-cells because these cells failed to grow.

Gene set enrichment analysis (GSEA). Total RNA was obtained from MSCs, defined as SSEA-4⁺ cells, cultured on the preservation ECM or uncoated plastic for 10 days, and analyzed on the basis of expression of 54,676 transcripts using Affymetrix Human Genome U133 Plus 2.0 chips. Transcripts (1741) either upregulated or downregulated in cells cultured on the preservation ECM versus on plastic were obtained based on using the statistical program significance analysis of microarrays (SAM) at a false discovery rate of 1%. The 721 upregulated transcripts were further analyzed for statistically significant enrichment of human MSCs gene expression pattern found in public gene sets from the NCBI GEO database (available on the world wide web at ncbi.nlm.nih.gov/geo/query/acc.cgi?acc 5 GSE10315) using the GSEA. The 721 upregulated gene set from cells cultured on the preservation ECM was highly overrepresented with a ranked list (red) of genes expressed by undifferentiated human bone marrow-derived MSCs. A Normalized Enrichment Score (NES) was 1.76 (actual ES divided by mean [ESs against all permutations of the dataset]); the Family Wise-error Rate (FWER) p-value was 0.016, which estimates the probability that the normalized enrichment score represents a false positive finding.

TABLE 4

Functional Annotation Clustering (Gene Ontology)

| | Count | P-value |
|---|---|---|
| Annotation Cluster 1 | | Enrichment Score: 23.86 |
| Cell cycle process | 141 | 4.7E−30 |
| Cell cycle | 157 | 5.2E−30 |
| Mitosis | 70 | 8.1E−28 |
| M phase of mitotic cell cycle | 70 | 1.5E−27 |
| Mitotic cell cycle | 81 | 5.8E−26 |
| Cell Division | 64 | 4.7E−22 |
| Regulation of cell cycle | 88 | 2.3E−15 |
| Annotation Cluster 2 | | Enrichment Score: 12.84 |
| Chromosome, pericentric region | 29 | 7.5E−15 |
| Chromosome | 68 | 5.3E−13 |
| Chromosomal part | 61 | 7.6E−13 |
| Annotation Cluster 3 | | Enrichment Score: 10.78 |
| Microtubule cytoskeleton | 77 | 2.7E−16 |
| Intracellular non-membrane-bound organelle | 219 | 7.7E−15 |
| Microtubnule | 49 | 2.4E−12 |
| Cytoskeleton | 140 | 2.6E−12 |
| Microtubule-based movement | 66 | 7.4E−8 |
| Cytoskeleton-dependent intracellular transport | 27 | 4.8E−7 |

Culture of MSCs on Marrow Stromal Cell-Derived Preservation Matrix Promotes Self-Renewal and Retention of Multipotentiality.

Self-renewal of MSCs was determined using a re-plating assay in which the increase in colony-forming cells following 7 days of pre-culture of MSCs was quantified (Di Gregorio et al., 2001). Because the previous experiments suggested that the effects of tissue culture plastic with and without coatings of purified collagen I or fibronectin on MSC colony formation and proliferation were similar, the following comparisons were only performed between the preservation ECM and the uncoated plastic.

FIG. 12A shows an example of colony formation generated by cells expanded on plastic or the preservation ECM after 7 passages, and clearly demonstrated that the number of colonies on plastic was lower than that on the preservation ECM. Next, the changes in replication of CFUs following serial passages were determined. The results showed that the replication of MSCs expanded on plastic was initially lower than that of MSCs expanded on the preservation ECM. Following serial passages, the replicative activity of the MSCs rapidly decreased when the cells were expanded on plastic as compared to those on preservation ECM (FIG. 12B, upper panels). When the accumulation of colony forming cells following serial passages was determined, the increase in the numbers of CFU-F, CFU-AD and CFU-OB were approximately 425-fold, 555-fold, and 336-fold greater after 9 to 10 passages, respectively, when cells were expanded on preservation ECM compared to plastic (FIG. 12B).

In view of the involvement of telomerase in the extension of telomere length associated with cellular life-span (Cong and Shay, 2008), the inventor also measured intracellular telomerase activity of expanded cells following each passage. During the entire subculturing time course, telomerase activity remained highly stable in cells maintained on the preservation ECM, but rapidly decreased in cells maintained on plastic.

Next, the inventor compared the influence of expansion on the preservation ECM on the capacity of MSCs to form bone in vivo using a transplantation assay (Bi et al., 2005). Following each expansion on the preservation ECM or plastic, the cells were loaded onto a hydroxyapatite/tricalcium phosphate (HA/TCP) carrier and implanted subcutaneously into immuno-compromised NIH-bg-nu-xid mice. Indeed, the amount of bone generated after 8 weeks by MSCs expanded on plastic and on the preservation ECM was very similar before passage 4, which was approximately 10-20% of bone in the total area of the ossicle (FIG. 12D & FIG. 12E). However, the differential amount of bone formed by cells cultured on these 2 systems was exaggerated after 7 passages. FIG. 12E shows that the amount of bone generated by MSCs expanded on plastic was dramatically decreased, to approximately <2% of bone in the total area of the ossicle. In contrast, MSCs expanded on preservation ECM for 7 passages still retained their ability to form bone, generating approximately 15% of bone in the total area of the ossicle (FIG. 12E).

Example 4

Preparation of Tissue-Specific Differentiation Matrices

1) Preparation of Human Skin Differentiation Matrix
Cells: HFF-1 fibroblast (human foreskin) purchased from ATCC(SCRC-1041, Lot. 5001118)
Procedures: One vial of human HFF-1 fibroblast (bought from ATCC) was thawed and plated into 3×T-175 flasks in 30 ml of DMEM/15% FCS per flask. The cells were cultured for 7-10 days reaching to 90% confluence, and then detached by treating with trypsin. The collected cells from 3×T-175 flasks were counted and frozen with label: HFF-1 (P1), $3×10^6$/vial.
Cultured human HFF-1 fibroblast (P3) were seeded into 6-well plates pre-coated with fibronectin at $2×10^4$ cells/ml in 3 ml of α-MEM/15% FCS or into 100 mm dishes pre-coated with fibronectin at $2×10^4$ cells/ml in 10 ml of α-MEM/15% FCS and cultured for 15 days. The medium was changed every 3-4 days; ascorbic acid (50 µM) was added during the final 8 days of culture. After extensive washing with PBS, cells were removed from the ECM by incubation with 0.5% Triton X-100 containing 20 mM $NH_4OH$ in PBS for 5 min at 37° C. The cell-free skin fibroblast-derived differentiation ECM dishes were stored in fungizone/PBS at 4° C.
2) Preparation of Mouse Muscle-Derived Differentiation Matrix
Cells: Fresh mouse muscle cells were acquired and plated onto one, 100 mm tissue culture dish in 10 ml of α-MEM/20% FCS and cultured until confluence.
Procedures: Cultured mouse muscle (P2) were seeded into 6-well plates pre-coated with fibronectin at $2×10^4$ cells/ml in 3 ml of α-MEM/20% FCS or into 100 mm dishes pre-coated with fibronectin at $2×10^4$ cells/ml in 10 ml of α-MEM/20% FCS and cultured for 15 days. The medium was changed every 3-4 days; ascorbic acid (50 µM) was added during the final 8 days of culture. After extensive washing with PBS, cells were removed from the differentiation ECM by incubation with 0.5% Triton X-100 containing 20 mM $NH_4OH$ in PBS for 5 min at 37° C. The cell-free mouse muscle-derived differentiation ECM dishes were stored in fungizone/PBS at 4° C.

3) Preparation of Human Fat Tissue-Derived Differentiation Matrix
Cells: Human fat stem cells (HADSC) purchased from GIBCO.
Procedures: HADSC (P2) were seeded into 6-well plates pre-coated with fibronectin at $2×10^4$ cells/ml in 3 ml of α-MEM/15% FCS or into 100 mm dishes pre-coated with fibronectin at $2×10^4$ cells/ml in 10 ml of α-MEM/15% FCS and cultured for 15 days. The medium was changed every 3-4 days; ascorbic acid (50 µM) was added during the final 8 days of culture. After extensive washing with PBS, cells were removed from the differentiation ECM by incubation with 0.5% Triton X-100 containing 20 mM $NH_4OH$ in PBS for 5 min at 37° C. The cell-free human fat tissue-derived ECM dishes were stored in fungizone/PBS at 4° C.
4) Preparation of Human Pancreas Tissue-Derived Differentiation Matrix
Cells: Human pancreas mixture cells (20% purity islet cells) in 2×T-25 flask (in ice box) in full medium (DMEM/15% FCS) were used. Cells reached 80% confluence.
Procedures: Pancreas cells (P2) were seeded into 6-well plates pre-coated with fibronectin at $2×10^4$ cells/ml in 3 ml of MEM/15% FCS or into 100 mm dishes pre-coated with fibronectin at $2×10^4$ cells/ml in 10 ml of MEM/15% FCS and cultured for 15 days. The medium was changed every 3-4 days; ascorbic acid (50 µM) was added during the final 8 days of culture. After extensive washing with PBS, cells were removed from the differentiation ECM by incubation with 0.5% Triton X-100 containing 20 mM $NH_4OH$ in PBS for 5 min at 37° C. The cell-free human pancreas tissue-derived ECM dishes were stored in fungizone/PBS at 4° C.
5) Preparation of Mouse Cardiac Muscle-Derived Differentiation Matrix
Cells: Cardiac muscle cells were harvested from 2 to 3 days old mice and cultured onto plastic in DMEM/15% FCS until confluence.
Procedures: The cultured cells (P1 or P2) were detached and reseeded into E-well plates pre-coated with fibronectin at $2×10^4$ cells/ml in 3 ml of MEM/15% FCS or into 100 mm dishes pre-coated with fibronectin at $2×10^4$ cells/ml in 10 ml of MEM/15% FCS and cultured for 15 days. The medium was changed every 3-4 days; ascorbic acid (50 µM) was added during the final 8 days of culture. After extensive washing with PBS, cells were removed from the differentiation ECM by incubation with 0.5% Triton X-100 containing 20 mM $NH_4OH$ in PBS for 5 min at 37° C. The cell-free mouse cardiac muscle-derived ECM dishes were stored in fungizone/PBS at 4° C.

Example 5

Isolation of MSCs Using the Cell-Derived Preservation Matrix

Cell-Free Extracellular Matrix (ECM) Made by Human Marrow Stromal Cells Isolates MSCs from hUCB.
Previous studies showed that the inventor successfully established a reproducible cell-free preservation ECM made by either human or mouse marrow stromal cells. In the present study, a preservation ECM derived from human marrow stromal cells is used for isolating mesenchymal stem cells (MSCs) from human umbilical cord blood (UCB). FIG. 7A shows cultured human marrow stromal cells elaborated a fibrillar ECM, as revealed by scanning electron microscopy (SEM) before and after cell removal. Confocal microscopic analysis indicated that the preservation ECM was comprised of at least collagen types I and III, fibronectin, biglycan, decorin, perlecan, and laminin (FIG. 7B). These proteins are important for binding growth factors to ECM and may play an important role in controlling MSC behavior. FIG. 7B shows that cells (blue) were absent following extraction, but the protein composition of the preservation ECM was well preserved as indicated by retention of immunostaining for all of the proteins examined.

Human UCB Contains a Large Number of Embryonic-Like Stem Cells.

UCB cells adhered to preservation ECM expressed SSEA-4 and other MSC markers, but no hematopoietic cell markers after 7 days of culture. The phenotypes of cells adhered to the preservation ECM were determined by flow cytometric analysis, indicating that ~50% of these cells expressed an ES cell marker SSEA-4 (21), and 80-90% of the cells also expressed several MSC markers including CD29, CD105, CD166 and CD146 (9), but none expressed CD34 and CD45 hematopoietic cell markers (FIG. 29). In contrast, cells adhered to plastic contained fewer SSEA-4$^+$ cells and small numbers of cells expressing those MSC markers. These results suggest that the phenotypes of cells adhered to preservation ECM are very different from those adhered to plastic.

UCB Cells Adhered to Preservation ECM Expressed Modest Levels of NANOG, OCT4, TDGF1, DNMT3B, GABRB3 and Sox2.

Figure 30:
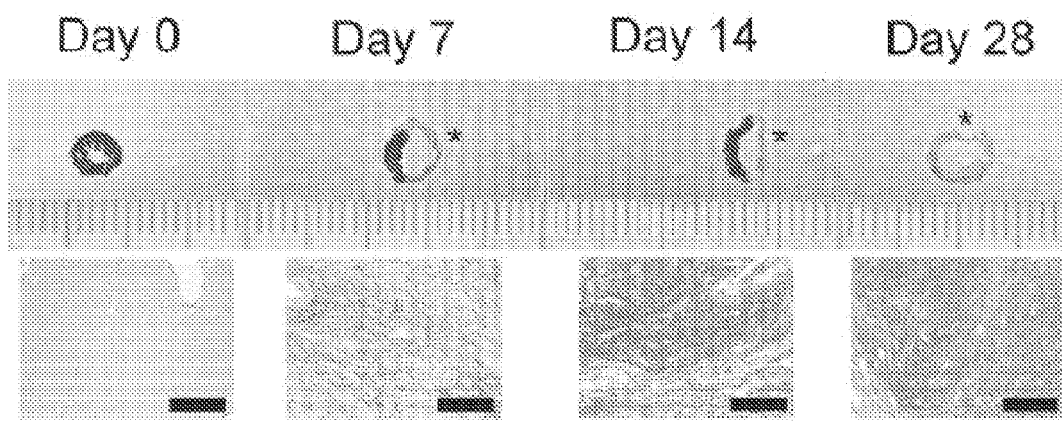
FIG. 30 MI time course. Top) Colorized hematoxylin and eosin stained images (*; scale is mm). Bottom) Picrosirius red stained section from the same LVs (scale=100 μm).

To further define this cell population, the inventor examined whether these cells expressed NANOG, OCT4, TDGF1, DNMT3B, GABRB3 and Sox2 that have been used to define undifferentiated hES cells. As previously reported, these genes were strongly up-regulated in hES cells as compared to any somatic stem cells tested (FIG. 30). However, the levels of those genes expressed by cells isolated from UCB by the preservation ECM were significantly higher than these cells isolated by plastic adhesion or bone marrow-derived MSCs. The results in gene expression profiles and phenotypes of surface antigens indicate that cells isolated by preservation ECM adhesion are a novel population that may exhibit unique characteristics, combining those from both MSCs and ES cells.

A large number of UCB-MSCs adhered to the preservation ECM, but not to plastic. The studies suggest that most adherent cells from UCB need as little as 20 minutes of incubation to attach to the preservation ECM (data not shown). FIG. 31A shows an abundance of UCB-derived fibroblast-like cells attached to the preservation ECM after 8, 24, and 72 hrs of incubation. Strikingly, some of these cells maintained on the preservation ECM had already developed colonies in 24 hrs. Additional colonies formed when cells were maintained on the preservation ECM for 72 hrs. In contrast, few cells attached to plastic, and no colonies were formed at any time points. This data indicates that MSCs isolated by the preservation ECM have much greater colonogenic capability than BM-MSCs. To determine whether non-adherent cells from uncoated plastic could further attach to the preservation ECM, non-adherent cells collected from plastic and preservation ECM after 8 or 72 hrs of incubation were reseeded onto preservation ECM plates. After incubation for additional 24 hrs, at least 10 times more non-adherent cells collected from plastic attached to the preservation ECM than those collected from the preservation ECM (FIG. 31B).

Figure 28:
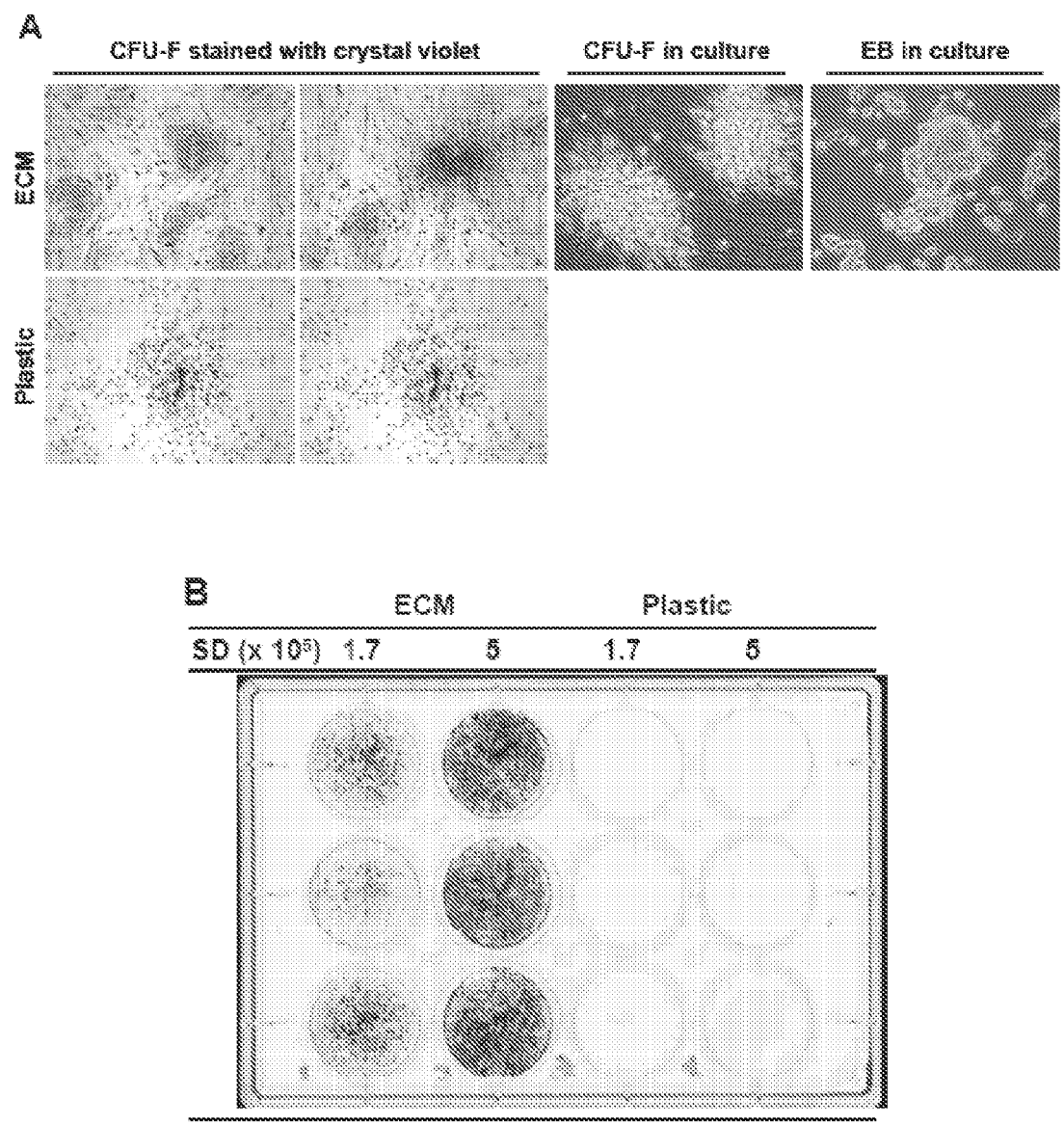
FIGS. 28A-B UCB-MSCs isolated by ECM adhesion formed numerous colonies. MNCs from UCB were seeded onto ECM or uncoated plastic at a low seeding density ($1 \times 10^5$ MNCs/CM$^2$) at 37° C.

Next, the inventor determined the frequency of MSCs by measuring the efficiency of colony forming unit-fibroblasts (CFU-F) (FIG. 28A, left and middle panels). Surprisingly, numerous colonies were formed when cells were cultured on the preservation ECM with a low seeding density ($1 \times 10^5$ MNCs/cm$^2$), suggesting that the frequency of MSCs in UCB was approximately $1.5 \times 10^4$ colonies/$10^8$ MNCs, at least $1.5 \times 10^4$-fold greater than that reported by others. Moreover, it appeared that some of the cells isolated by the preservation ECM generated embryonic bodies, a unique feature of hES cells (FIG. 28A, right panel). To assess colony formation of CFU-osteoblasts (CFU-OB), CFU-F colonies were maintained for an additional 25 days in an osteoblast differentiation medium described in the Methods section. When cultured on preservation ECM, UCB-MSCs developed CFU-OB (FIG. 28B). The number of CFU-OB formation was seeding-density dependent. In contrast, no CFU-OB formation was found in cells cultured on plastic. Taken together, the data indicates that preservation ECM strongly enhances the attachment and proliferation of UCB-MSCs as well as retains their ability to differentiate into osteoblasts.

UCB-MSCs adhered to preservation ECM differentiated into functional mature cardiomyocytes in vitro. The differentiation procedures have been previously described. Briefly, UCB-derived cells (P1) were seeded at $1 \times 10^6$ cells/cm$^2$ and cultured for 2 days in a growth medium, followed by the addition of 5 µM 5-azacytidine (Sigma), and cultured for an additional 3 days. Then the cells were maintained in the differentiation medium [DMEM containing 10% FBS, $10^{-4}$ M ascorbic acid (Sigma), 10 ng/ml TGF-β] up to 25 days. The medium was replaced every 4 days. In this experiment, UCB-MSCs obtained by plastic adhesion procedures failed to grow in long-term expansion. Only the cells adhered to preservation ECM were able to grow reaching confluence. FIG. 29A shows that treated UCB-MSCs differentiated into myogenic cells with formation of myotubes. Specifically, beating cells (~45 beats/min) were observed in dense cell areas, indicated by white circles. Moreover, the treated cells expressed significantly higher levels of cardiomyocyte specific transcripts such as cardiac troponin T (TropT), and β-myocin heavy chain (βMHC) than the controls. These primers were provided by Applied Biosystems Inc (Foster City, Calif.) for detecting the expression of TropT and βMHC from either human or mouse (FIG. 29B).

UCB-MSCs isolated by preservation ECM adhesion generated tissues originated from 3 embryonic germ layers in vivo. To evaluate the ability of these cells to generate functional tissues, the inventor transplanted the cells into immunocompromised mice subcutaneously, and found that cells obtained by preservation ECM generated tissues originated from 3 germ layers: mesoderm origin including muscle, fat, bone and blood vessel; endoderm origin such as gland; and ectoderm origin such as nerve (FIG. 34). Moreover, UCB-MSCs isolated by the preservation ECM generated enormous amounts of muscle, gland and blood vessels, which have never been reported in UCB-MSCs isolated by plastic or BM-MSCs. In the experiments, most implants contained heterogeneous tissues generated by cells like hES cells, however, no teratoma occurred. It is possible that modest expression of these six genes may prevent teratoma formation.

Human umbilical cord blood (UCB) will be purchased from Texas Cord Blood Bank (San Antonio, Tex.); and human bone marrow cells from 20-30 year old donors will be purchased from ALLCELLS (Emeryville, Calif.).

Initially, mononuclear cells (MNCs) will be isolated from human UCB using the Ficoll-Paque Premium density solution (GE Healthcare) as described previously in PCT/US2009/047981. Then MNCs will be seeded onto uncoated tissue culture plastic or tissue culture plastic coated with human extracellular matrix (ECM) made by cultured human marrow stromal cells at $1 \times 10^6$ MNCs/cm2, and grown to 80% confluence (2 to 3 weeks) in a growth medium containing aMEM (Life Technologies, Grand Island, N.Y., USA), 20% fetal bovine serum, 0.1 mg/ml Primocin (Invitrogen) 15 mM HEPES, 4 mM L-glutamine, 2 mM GlutaMax (Invitrogen), 1×ITS+3 (Sigma), 0.1 mM 2-2-mercaptoenthanol, 0.1 mM non-essential amino acid, 4 ng/ml bFGF. The cultures will be washed with phosphate-buffered saline (PBS) to remove non-adherent cells. Then adherent cells, considered as passage 1 (P1), will be detached by trypsin treatment for uncoated plastic or by collagenase treatment for the preservation ECM coated plastic, collected and frozen for storage or directly used for RNA preparations or the investigation of the behavior of cells. The data obtained from the fluorescence-activated cell sorting (FACS) analysis suggest that there are fewer hematopoietic cells in this adherent cell population (P1) (FIG. 24). The same procedure will be used to culture human bone marrow cells. Human embryonic stem (hES) cells will serve as a positive control.

Characteristics of the hUCB-MSCs Isolated by Cell-Derived Preservation Matrix Adhesion.

RNA will be harvested from MSCs (P1) using the "subpooling" approach whereby 3 subsets of RNA samples within each group will be made, each subset comprising RNA pooled from 3 individuals for subsequent hybridization on one chip. After pooling, RNA will be sent to Genome Explorations (available on the world wide web at genome-explorations.com). There, RNA will be converted to DNA and labeled cRNA prepared, which will be hybridized onto the chips. The chips will be scanned, and data will be pre-analyzed using Affymetrix MAS 5.0. Gene expression levels on ES cell chips (ES-A, ES-B, and ES-C) will be compared with levels on UCB-MSC (the cells obtained by ECM) chips (UCB/ECM-A, UCB/ECM-B, and UCB/ECM-C), or UCB-MSC (the cells obtained by plastic) chips (UCB/plastic-A, UCB/plastic-B, and UCB/plastic-C), or BM-MSC chips (BM-A, BM-B, and BM-C) to determine expression differences among these groups. One-way ANOVA will be performed for each gene. Genes with p values less than 0.05 will be considered significant.

After pre-selecting genes with differential expression, advanced analysis including hierarchical clustering, functional classification, and reconstruction of biological pathways will be performed using the software GeneSpring™ from Silicon Genetics (Redwood City, Calif.), and Gene Ontology (GO), a public database. The genes highly associated with the functional groups will be determined by Fisher's Exact Test, and then organized into virtual pathways using PathwayAssist 3.0 (available on the world wide web at ariadne-genomics.com). In order to further demonstrate the similarity with all published stem cell gene expression profiles, Gene Set Enrichment Analysis (GSEA) will be used to examine a variety of data sets from the NCBI GEO database that have enrichment of the same genes expressed in the UCB-MSC gene set.

According to the previous results shown in FIG. 30, NANOG, OCT4, TDGF1, DNMT3B, GABRB3 and Sox2 were strongly up-regulated by hES cells, suggesting that the properties of hES cells are appropriately retained in the culture system. Studies showed the modest expression of hES cell-specific genes in UCB-MSCs/ECM, which could be very important in maintaining stem cell pluripotentiality without causing teratoma formation.

Example 6

Tissue-Specific Cell-Derived Differentiation Matrix Induces Tissue-Specific Differentiation of Stem Cells Studies suggest that UCB-MSCs isolated and expanded by this unique preservation ECM culture system can be selectively induced to commit to a homogenous osteoblast or cardiomyocyte lineage. Implantation of UCB-MSCs obtained by cell-derived preservation ECM adhesion into immunocompromised mice generated tissues of 3 embryonic germ layers (FIG. 34), but no teratoma occurred. Also, these cells expressed a modest level of 6 hES cell-specific genes (FIG. 30). These findings indicate that UCB-MSCs isolated by cell-derived preservation ECM have unique features that may combine some of the characteristics of both adult MSCs and ES cells. Moreover, recent evidence suggests that UCB-MSCs isolated and expanded by the unique cell-derived preservation ECM culture system can be selectively induced to commit to a homogenous osteoblast or myoblast lineage (FIG. 28B & FIG. 33).

MSCs isolated from UCB will be seeded onto uncoated tissue culture plastic or tissue culture plastic coated with human cell-derived preservation ECM made by cultured human marrow stromal cells and grown to 70% confluence (~2 to 3 weeks). The cultures will be washed with PBS to remove non-adherent cells. Then the adherent cells (P1) will be detached and maintained on ordinary plastic under conditions known to induce commitment to a specific cell lineage from mesoderm including osteoblasts, adipocytes, and chondrocytes, ectoderm such as neurons, and endoderm such as hepatocytes, using previously described culture conditions and assays. The presence of differentiated progeny will be detected using histochemical staining for calcified matrix (Von Kossa), lipid (Oil Red O), and cartilaginous matrix (Alcian blue), Nestin, and albumin expressed by hepatocytes, respectively.

It has been reported that UCB-MSCs can be induced to commitment to cardiomyocytes by treating with bFGF and azacytidine (Sigma Aldrich). UCB-MSCs (P1) isolated by cell-derived preservation ECM adhesion as well as those isolated by plastic adhesion will be maintained on ordinary plastic under this condition. The presence of differentiated progeny will be detected using immunohistochemical staining for human cardiac troponin I and myosin ventricular heavy chain α/β, and using TaqMan PCR to detect cardiac specific transcription factors Nkx2.5 and GATA-4, and other markers including cardiac troponin T (TropT), β-myocin heavy chain (βMHC) and cardiac actin (cActin). Beating cells occurring during cell culture will be recorded by video. For a positive control, BM-MSCs or hES cells will be treated in the same way as UCB-MSCs, and for a negative control, the cells will be treated with a regular growth medium.

To direct these cells to differentiate into a specific lineage, they may be induced by being maintained on a tissue-specific differentiation ECM that simulates a specific microenvironment in vivo. Interestingly, ECMs grown from fibroblasts isolated from tissues associated with specific cell types provide tissue-specific cues to stem cells. For example, ES cells form a polarized epithelium when cultured on Matrigel, but form a cartilaginous structure when cultured on matrices prepared from cartilage extracts. As shown previously, synovium derived stem cells (SDSC) maintained on a cell-derived preservation ECM made by synovium-derived cells diminished their ability to differentiate into osteoblasts and adipocytes, which is evidence that tissue-specific cell-derived ECMs may play a role in directing stem cell differentiation. Moreover, the sensitivity of BM-MSCs to exogenous BMP-2 was dramatically increased when they were grown on a bone marrow-derived tissue specific ECM as compared to culture on a skin tissue-specific ECM made by skin fibroblasts (unpublished results). This is interesting because others have shown that BM-MSCs have the ability to differentiate into (among others) bone and skin cells. If the microenvironment provided by the ECM was irrelevant, one could logically conclude that BM-MSCs cultured on a skin tissue-specific ECM with exogenous BMP-2 added compared to an identical sample of BM-MSCs cultured on a bone marrow tissue-specifc ECM with exogenous BMP-2 added would react similarly. Of course, this is not the result achieved. The fact that the bone marrow ECM cultured MSCs were dramatically more sensitive to the exogenous BMP-2 vs. the skin tissue-specific ECM cultured MSCs suggests the microenvironment presents powerful cues to stem cells that, at least in this case, were sufficiently powerful to overcome the powerful bone induction signal provided by the BMP-2. Thus, tissue specific differentiation ECMs provide a powerful but reasonably 'natural' and practical in-vitro method to cause stem cells to selectively differentiate into a desired cell lineage for clinical and research applications and the treatment of physiologic deficiencies, tissue regeneration and other cell-based therapies. In addition to bone marrow-derived ECM, in vitro reconsitution of at least skin-, muscle-, adipose tissue-, and cartilage-derived differentiation ECMs has been performed.

Example 7

Repair of Damaged Tissues In Vivo with the Isolated MSCs

Studies in vitro have indicated that UCB-MSCs obtained by cell-derived preservation ECM adhesion can differentiate into myoblasts (FIG. 33) and by those in vivo implying that these cells may favor muscular genesis and angiogenesis (FIG. 34). Traditionally, stem cells are considered for the regeneration of tissue, but evidence suggests that stem cells can produce various cytokines needed and deliver them to a local area for the repair of defects. Transplantation of these cells into myocardium after a myocardial infarction (MI) may not only give rise to cardiomyocytes, but also increase the neovascularization that is critical to improve myocardial function.

Performing Mouse MI Surgeries to Obtain Samples Up to 28 Days Post-MI.

Mice were sacrificed at 0, 7, 14, and 28 days post-MI (n=3 males for each time; FIG. 30). The average infarct size was 47±4% and cumulative post-MI mortality was 26%.

Induction of MI.

MI will be induced in 6-month old female immunodeficient beige mice (NIH-bg-nu-xid). The mouse left coronary artery crosses the left ventricle (LV) free wall, similar to the human ramus intermedius coronary artery, such that ligation results in reproducibly large MI's involving the anterolateral, posterior, and apical regions. Under anesthesia, the heart will be exposed via a left thoracotomy and the left anterior descending coronary artery will be ligated using a 8-0 silk suture. Sham mice will serve as surgical controls.

Injection of Cells.

Immediately following the induction of MI before the chest is closed, the inventor will inject $1 \times 10^6$ cells suspended in 35 µl PBS into the intramyocardium at the LV. The inventor will inject approximately 10 µl into each of 3 locations that are within the region that will become infarcted. For comparison, mice will be administrated UCB-MSCs isolated by preservation ECM adhesion (UCB-MSCs/ECM), or UCB-MSCs isolated by plastic adhesion (UCB-MSCs/Plastic), or hES cells (hESCs) serving as a positive control. The negative control will be MI mice which do not receive cells.

TABLE 5

| | Number of animals requested | | | |
|---|---|---|---|---|
| | Number of mice | | | |
| Post-injection | Day 1 | Day 7 | Day 14 | Day 28 |
| Sham/No inj. | 8 | 8 | 8 | 8 |
| Sham/inj. UCM-MSCs/ECM | 16 | 16 | 16 | 16 |
| MI/No inj. | 12 | 12 | 12 | 12 |
| MI/inj. UCB-MSCs/ECM | 18 | 18 | 18 | 18 |
| MI/inj. UCB-MSCs/Plastic | 18 | 18 | 18 | 18 |
| MI/inj. hESCs | 18 | 18 | 18 | 18 |

Total animals: 352; the number of animals per group is decided based on the survival rate (70%) after MI and achievement of 80% power to detect a significant effect when the effect size is only 1.5 (56). In each group, 6 mice will be used for examining LV function; and 6 mice will be used for histological analysis.

Examination of Mouse LV Function.

Cardiac function (LV) will be measured at days 1, 7, 14 and 28 after cell transplantation using echocardiography and hemodynamics. Echocardiography (FIGS. 31 & 32) is a non-invasive procedure that allows assessment of both systolic and diastolic function, and will be performed serially on the mice to determine temporal changes. Serial imaging will show the temporal effects of MI on LV structure and function. The baseline for each animal will be obtained before surgery. Pressure-volume loops will demonstrate changes in hemodynamics post-MI. From these parameters, the inventor will calculate thinning index as infarct to septal wall thickness ratio; dilation index as ratio of LV cavity to entire area; and expansion index as ratio of dilation index to thinning index.

Histological Analysis.

Mice will be killed at days 1, 7, 14 and 28 after cell transplantation. The LV will be sectioned into 3 transverse slices and incubated in 1% 2,3,5-triphenyltetrazolium chloride (Sigma Chemical Co) dissolved in saline for infarct size determination (mid section shown in FIG. 33). To visualize human cells (the implanted cells) in vivo, the frozen sections will be stained with immunofluorescence conjugated antibodies (Millipore, Billerica, Mass.) specifically against a human nuclear matrix antigen, which can detect the presence of UCB-MSCs in the mouse infarct zone. Sarcomeric structure generated by the differentiated UCB-MSCs will be determined by double-stained for human nuclear matrix antigen and cardiac troponin T (TropT), or β-myocin heavy chain (βMHC), or cardiac actin (cActin).

Methods

Preparation of Cell-Free Preservation ECM from Cultured Bone Marrow Cells.

Freshly isolated human bone marrow mononuclear cells (containing MSCs) obtained from 20-30 year old donors will be purchased from ALLCELLS (Emeryville, Calif.). These cells will be seeded onto tissue culture plastic at $3 \times 10^5$ cells/cm$^2$, and grown to 70% confluence (2-3 weeks) in α-MEM (Life Technologies, Grand Island, N.Y., USA), glutamine (2 mM), penicillin (100 U/ml), streptomycin (100 µg/ml, Biofluids, Rockville, Md., USA), and 15% pre-selected fetal bovine serum (FBS, Becton Dickinson, Franklin Lakes, N.J., USA). The cultures will be washed with PBS to remove non-adherent cells. Then, the adherent cells will be detached by trypsin treatment (0.02% for 2 minutes at 37° C.), and reseeded into tissue culture plastic at $1 \times 10^4$ cells/cm$^2$ and cultured for 15 days. The medium will be changed every 3-4 days; ascorbic acid (50 µM) will be added during the final 8 days of culture. After extensive washing with PBS, cells will be removed by incubation of 0.5% Triton X-100 containing 20 mM NH4OH in PBS for 5 minutes at room temperature. The plates will be then washed with PBS 4 times, added PBS containing 50 µg/ml gentamicin and 0.25 µg/ml Fungizone, and store at 4° C. up to 4 months.

Isolation and Culture of MSCs from Human Umbilical Cord Blood.

Mononuclear cells (MNCs) will be isolated from human umbilical cord blood (UCB) using the Ficoll-Paque Premium density solution as described previously in PCT/US2009/047981. Briefly, the anticoagulated cord blood will be diluted (1:1) with balanced salt solution (BSS), laid on 10 ml of Ficoll-Paque PREMIUM solution (GE Healthcare BioSciences Corp., Piscataway, N.J.) layer (ratio 4:1) in a 50 ml tube, and centrifuged at 480 g for 30 min at 18-20° C. Then the mononuclear/white layer will be collected and transferred to a new 50 ml tube. The collected MNCs will be added 3 volumes of BSS, centrifuged at 480 g for 6 min at 18-20° C., and the pellet will be re-suspended in 10 ml aMEM containing 2% FBS. The MNCs will be seeded onto tissue culture plastic either uncoated or coated with preservation ECM made by cultured human bone marrow stromal cells at a density of $1 \times 10^6$ MNCs/cm$^2$, incubated for 24 hrs at 37° C. to allow attachment of adherent cells, and washed twice with PBS to remove non-adherent cells. Then, a growth medium (α-MEM containing 20% FBS, 15 mM HEPES, 4.5 g/L glucose, 4 mM glutamine, 1 mM sodium pyruvate, 0.1 mM non-essential amino acid, 0.1 mM 2-mercaptoenthanol, 1 U/ml insulin, and 5.5 mg/L transferrin) will be added. The adherent cells will be cultured at 37° C. in a humidified atmosphere containing 5% $CO_2$ until they reach 70% to 90% confluence. Then adherent cells, considered as passage 1 (P1), will be detached by trypsin treatment for uncoated plastic or by collagenase treatment for the preservation ECM coated plastic, collected and frozen for storage or directly used for RNA preparations or the investigation of the behavior of cells. The results from FACS analysis indicate that these cells exhibit MSC phenotypes. This population contains fewer hematopoietic cells (FIG. 29).

Maintenance of hES Cells.

Cell line H7 purchased from National Stem Cell Bank (Madison, Wis.) will be maintained by biweekly passage in tissue culture plastic pre-coated with a substrate (Cellstart) provided by Invitrogen Co (Carlsbad, Calif.) and in a growth medium (StemProhESC SFM) provided by Invitoigen Co. (Carlsbad, Calif.) according to the manufacturer's instructions.

Surgical Procedures for Induction of Myocardial Infarction (MI) and Injection of Cells.

A surgical plane of anesthesia will be achieved by placing the mouse in a flow-through system containing 3-4% isoflurane in a 100% oxygen mix. Following loss of consciousness, the mice will be placed on a modified mask assembly that allows a continuous flow of 2-3% isoflurane in an oxygen mix. The mice will be taped on the surgical board in the supine position. The board contains a warming element that is regulated by the rectal temperature of the mouse and can be adjusted as needed. The board also allows us to monitor and record EKG and heart rate before, during, and after the surgery. A midline cervical incision will be made along the reflection of the muscles overlying the trachea to allow visualization of the endotracheal tube to confirm correct placement. The endotracheal tube, PE size 90, will be inserted 5-8 mm from the larynx, taped to prevent dislodgement, and connected to the mouse ventilator. The ventilator is set at a volume of 0.20-0.25 cc and a rate of 180-200 cycles/minute maintaining a flow rate of 2-3% isoflurane. The inhalation anesthetic flow rate will be adjusted based upon heart rate and pedal reflex response and will be regularly assessed during the surgical procedure.

The chest will be prepped in sterile fashion, including removing hair with Nair. A 1 cm vertical incision will be made about 1 cm above the xiphoid. Pectoralis muscles will be refracted apart with 8-0 prolene sutures exposing the ribs. An incision will be made between the 3rd-4-th intercostal muscles and the ribs will be refracted with a retractor to expose the heart and lungs. A small piece of gauze will be inserted to separate the heart and lungs. After opening the pericardium, a 8-0 prolene suture that has an atraumatic needle (Ethicon, K801) will be placed underneath the left anterior descending coronary artery 1-3 mm from the tip of the left atrium just proximal to the main bifurcation of the artery, and the artery will be then ligated. Infarction will be defined by ST elevation on the electrocardiogram and will be confirmed at necropsy.

Immediately following the induction of MI, $1 \times 10^6$ cells suspended in 35 µl PBS will be injected into the infarct. Successful injections should be characterized by the formation of a discolored bleb near the site of injection. The ribs will be closed with 8-O prolene. The retracted pectoralis muscles will be put back in their original position to cover the ribs, the skin will be closed with 5-0 silk, and the animal will be extubated. After extubation, the mouse will be given buprenorphine (0.05-0.1 mg/kg SC) and oxygen by mask and placed on a warming blanket during recovery. The mice will be monitored closely until they are alert and freely moving around. The mice will be checked daily.

Cardiac Function Measurements.

Figure 31:
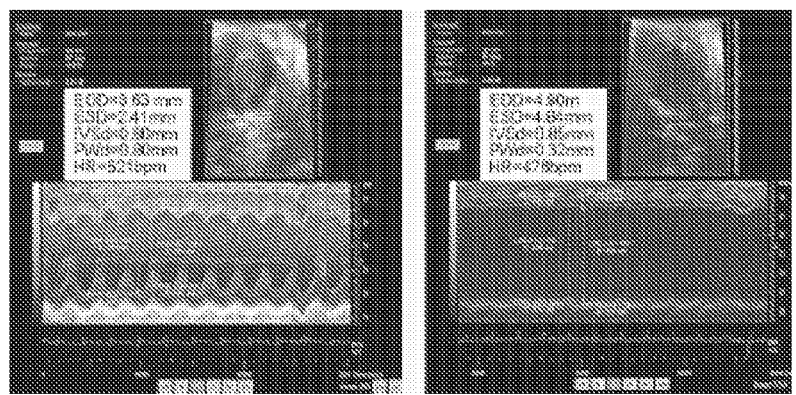
FIG. 31 Echocardiograms showing short axis (top) and m-mode (bottom) images and calculations from same mouse at baseline (left) and 7 days post MI (right).

The Vevo 770™ High-Resolution In Vivo Imaging System (120V) from Visual Sonics will be used for echocardiographic assessments. The Vevo 770 offers spatial resolution down to 30µ, which is currently the highest resolution available in real-time. For the echocardiographic studies, the mice will be initially anesthetized by placing them in a flow-through system containing 3-4% isoflurane in a 100% oxygen mix. Following loss of consciousness, the mice will be placed on a modified mask assembly that allows a continuous flow of 1-2% isoflurane in an oxygen mix, and maintained at 37° C. EKG and heart rate will be monitored throughout the imaging procedure, using a surface electrocardiogram. From a transthoracic approach, two-dimensional targeted M-mode echocardiographic recordings will be obtained. Briefly, the two-dimensional parasternal long-axis view of the LV will be first recorded in order to precisely define the LV long axis and papillary muscles (FIG. 32). A perpendicular view with respect to the LV long axis will then be obtained in order to view the two-dimensional parasternal short axis. LV short-axis two-dimensional and M-mode echocardiographic recordings will then be recorded (FIG. 31). The LV dimensions will be taken from the septum to the posterior LV free wall with the cursor directed between the papillary muscles. The measurements will be repeated serially, such that every mouse will have echocardiography for all time points up to sacrifice.

Hemodynamic Analysis.

Hemodynamic measurements will be made at the end of the study to assess left ventricular pressure and volume. This procedure is a non-survival surgery that will be performed before sacrifice. The inventor will use Millar's Aria™-1 Pressure-Volume Conductance Unit (MPCU-200) to acquire the hemodynamic data and the PV Analysis for Windows® (PVAN) software package for pressure-volume analysis. Following the final echocardiogram, the right carotid artery will be exposed, and a microtipped transducer catheter (1.2 French, Millar SPR-671, TX) and will be advanced into the LV. After obtaining baseline measurements, a small volume (10-20 µl) of hypertonic saline will be injected via the cannulated left jugular vein in order to calibrate the volume. Then, a lateral incision below the diaphragm will be made and the diaphragm will be cauterized to expose the inferior vena cava (IVC) and thoracic artery. The IVC will be transiently occluded for 4-5 seconds while the measurements are recorded. Likewise, the thoracic artery will be transiently occluded for 4-5 seconds while the measurements are recorded. There should be minimal blood loss during this procedure. A flow probe will then be placed adjacent to the thoracic artery to obtain cardiac output. Following these measurements, the catheter will be removed. The mouse will be euthanized by removing the heart under continuous isoflurane (5%).

Histological Analysis.

Following 0, 1, 3, 5, 7, 14, and 28 days MI with or without injection of cells, the mice will be euthanized to obtain tissue samples. Briefly, the mice will be anesthetized with inhalational isoflurane and the coronary vasculature will be flushed with saline. The hearts will be excised, the right and left ventricles separated, and the left ventricle sliced into 3 slices from apex to base. These slices are incubated in 1% 2,3,5-triphenyltetrazolium chloride (TTC, Sigma Chemical Co, St. Louis, Mo.) dissolved in saline and warmed to 37° C., to stain viable myocardium red and infarct areas white. The slices are photographed for infarct size determination (FIG. 34). For histological analysis, the slices will be fixed in 10% zinc-buffered formalin (Z-Fix; Anatech Ltd) and embedded in paraffin. Paraffin embedded sections will be stained with hematoxylin and eosin and picrosirius red (FIG. 39) for routine histological evaluation.

To visualize human cells (the implanted cells) in vivo, the frozen sections will be performed and stained with immunofluorescence conjugated antibodies (Millipore, Billerica, Mass.) specifically against a human nuclear matrix antigen, which can detect the presence of UCB-MSCs in the mouse infarct zone. Sarcomeric structure generated by the differentiated UCB-MSCs will be determined by double-stained for human nuclear matrix antigen and cardiac troponin T (TropT), or β-myocin heavy chain (βMHC), or cardiac actin (cActin).

Osteogenesis.

UCB-derived cells (P1) will be maintained for up to 25 days in osteogenic medium (DMEM containing 10% FBS, $10^{-8}$ M dexamethasone and $10^{-4}$ M L-ascorbate-2-phosphate). One-half of the medium will be replaced every 5 days. Transcript levels of osteoblast differentiation markers including alkaline phosphatase, osteocalcin, bone sialoprotein, and Type I collagen will be determined by TaqMan PCR on day 5, 7, 14, and 25 of culture. For determination of sensitivity to BMP-2, recombinant BMP-2 (R&D systems, Inc., Minneapolis, Minn.) will be added to the cultures. Alkaline phosphatase activity will be determined after 2 days, and osteocalcin secretion will be measured by RIA after 6 days. The dose and time for adding BMP-2 will be determined by the pilot experiments.

Adipogenesis.

UCB-derived cells (P1) will be maintained for 14 days in adipogenic medium (DMEM containing 10% FBS, 0.5 mM IBMX, $10^{-7}$ M dexamethasone, 10 µM insulin, 200 µM indomethacin). One-half of the medium will be replaced every 5 days. Adipocytes will be visualized with Oil Red O staining. Transcript levels of adipocyte markers including PPARγ2 and AP2 will be determined by TaqMan PCR on day 5, 7, and 14 of culture.

Chondrogenesis.

Chondrogenic differentiation will be induced. Briefly, UCB-derived cells (P1) suspended in 10 µl of 8×106 cells/ml will be plated into the center of individual wells of 24-well plates, and allowed to attach for 3 hrs at 37° C. Then chondrogenic medium (DMEM containing 1% FBS, 6.25 µg/ml insulin, 10 ng/ml TGF-α1, 50 nM ascorbate-2-phosphate) will be gently overlaid, and cultures will maintained for 2 weeks. Transcript levels of type II collagen will be determined by TaqMan PCR. Chondrogenesis will be further confirmed using the histologic stain with Alcian Blue.

Neuronal Differentiation.

The procedure used will be a modification of the technique previously described in PCT/US2009/047981. Briefly, UCB-derived cells (P1) will be seeded at 1×10$^6$ cells/cm$^2$ and maintained for 14 days in neuronal differentiation medium [DMEM/F-12 containing 10% FBS, 10 ng/ml human epidermal growth factor (hEGF), 10 ng/ml stem cell factor (SCF) 10 ng/ml human neural growth factor (hNGF), 10 ng/ml basic fibroblast growth factor (bFGF)]. One-half of the medium will be replaced every days. Neuroblasts will be determined by immunohistochemical staining with specific monoclonal antibodies against Nestin and glial fibrillary acidic protein (GFAP).

Hepatocyte Differentiation.

UCB-derived cells (P1) will be seeded at 1×10$^6$ cells/cm$^2$ and maintained for up to 25 days in DMEM containing 15% FBS, 10 ng/ml FGF-1, ng/ml FGF-2, 10 ng/ml leukemia inhibitory factor (LIF), 10 ng/ml stem cell factor (SCF), ng/ml hepatocytes growth factor (HGF) and 10 ng/ml oncostatin M (OSM). The medium will be replaced every 7 days. Hepatocytes will be determined by immunohistochemical staining with specific antibodies against hepatocyte markers including human albumin (ALB) and human cytokeratin (CK)-18. Transcript levels of ALB and CK-18 and others hepatocytes markers including human glutamine synthetase (GS) and human alpha-fetoprotein (AFP) will be quantified by TaqMan PCR on day 7, 14, 21, and 25 of culture.

Cardiomyocyte Differentiation.

UCB-derived cells (P1) will be seeded at 1×10$^6$ cells/cm$^2$ and cultured for 2 days in DMEM containing 10% FBS, then 5 µM 5-azacytidine (Sigma) will be added, and cultured for additional 3 days. Then the cells will be maintained in the differentiation medium [DMEM containing 10% FBS, $10^{-4}$ M ascorbic acid (Sigma), 10 ng/ml TGF-β] up to 25 days. The medium will be replaced every 4 days. Cardiomyocytes will be determined by immunohistochemical staining with specific antibodies against sarcomeric proteins including troponin-I and α-actinin. Transcript levels of cardiomyocyte specific transcription factors MEF2C, GATA-4, and NKx-2.5, and other markers including cardiac troponin T (TropT), β-myocin heavy chain (βMHC) and cardia actin (cActin) will be quantified by TaqMan PCR on day 7, 14, 21, and 25 of culture. Beating cells occurring during cell culture will be recorded by video.

Preparation of RNA, and Real Time PCR.

Total RNA will be extracted from cultured cells using Ultraspec™ RNA (Biotecx, Houston, Tex.). RNA (2 µg) will be reverse-transcribed using a High Capacity cDNA Archive Kit (Applied Biosystems, Foster City, Calif.). The transcripts of interest, and that of the housekeeping gene GAPDH, will be amplified from cDNA by real-time PCR using TaqMan Universal PCR Master Mix and Assay Demand or Assay by Design primer and probe sets (Applied Biosystems). Amplification and detection will be carried out with an ABI Prism 7500 Sequence Detection System (Applied Biosystems) as follows: 5-min denaturation at 95 C for 10 min, 40 cycles of amplification including denaturation at 94 C for 15 sec and annealing/extension at 60 C for 1 min. Gene expression will be quantified by subtracting the GAPDH threshold cycle (Ct) value from the Ct value of the gene of interest, and expressed as $2^{-\Delta ct}$, as described by the protocol of the manufacturer.

Example 8

Regeneration of Stem Cells from Old Subjects by Exposure to a Preservation ECM Derived from Cells of a Young Subject In the present study, the inventor propose a model to study the roles of MSC aging (cell intrinsic) and preservation ECM or niche aging (cell extrinsic). Studies revealed that defects in replication (in vitro) and bone formation capacity (in vivo) of aged MSCs were very remarkable and reproducible. Moreover, the increased oxidative stress associated with old age exhausts a limited pool of MSC or osteoblast progenitors, and the old-ECM itself, and/or factors embedded in it, contributes by increasing ROS or reducing defenses against oxidative stress. More importantly, this study indicates that aging negatively impacts the formation of an endogenous ECM that normally preserves MSC function, and MSCs from aged animals can be improved by culture on a preservation ECM made by stromal cells from young mice. Taken together, the inventor suggest that culture of aged MSCs on a young preservation ECM may improve their number and quality, thereby optimizing the effectiveness of autologous MSC administration for future therapeutic applications.

Preparation of Cell-Free Preservation Matrix Generated by Cultured Bone Marrow Cells from Either Young or Old Mice.

A cell-free differentiation matrix was prepared from cultured femoral marrow cells from either 3-month-old (young) or 18-month-old C57BL/6 mice (young preservation ECM, or old preservation ECM, respectively). Briefly, freshly isolated bone marrow cells from either young or old mice were cultured in E-well plates (Corning Inc, Corning, N.Y.) at $3\times10^6$ cells/10 cm² well in 4 ml of a standard culture medium comprising α-MEM (Life Technologies, Grand Island, N.Y.) supplemented with glutamine (2 mM), penicillin (100 U/ml), streptomycin (100 µg/ml) (Sigma Chemical Company, St. Louis, Mo.), and 20% pre-selected fetal bovine serum (FBS, Atlanta Biologicals, Lawrenceville, Ga.). After 7 days of culture, non-adherent cells were removed by rinsing with PBS. The adherent stromal cell layer was dispersed with PBS containing 400 U/ml type II collagenase (Worthington Biochemical Inc, Lakewood, N.J.) for 10 min at 37° C., then $1\times10^5$ adherent cells were seeded into a 10 cm² well of a 6-well plate containing a 24 mm×30 mm Thermanox plastic coverslip (Nalge Nunc International, Rochester, N.Y.), and cultured for an additional 15 days. The medium was changed every 3-4 days; ascorbic acid (50 µM) (Sigma Chemical Company) was added during the final 8 days of culture. After extensive washing with PBS, cells were removed from the ECM by incubation with 0.5% Triton X-100 containing 20 mM $NH_4OH$ in PBS for 5 minutes at 37° C., similar to a previously described procedure (Vlodaysky, 1999). The ECM was washed with PBS 3 times, and stored in 2.0 ml of PBS containing penicillin (100 U/ml), streptomycin (100 µg/ml) and fungizone (0.25 µg/ml) at 4° C. for up to 4 months.

The replication and osteogenesis of young or old MSCs maintained on young preservation ECM versus old preservation ECM as well as plastic were examined in vitro and in vivo.

Defective Replication of Aged MSCs is Restored by Exposure to a Young-Preservation Matrix.

The inventor first examined whether aging negatively impacted the number and ex vivo replication of MSCs by comparing femoral marrow cells isolated from 3-month old (young) to 18-month old (old) female C57BL/6 mice. In this experiment, MSCs and osteoblast progenitors were defined by their ability to form a colony of osteoblastic cells (CFU-OB). Freshly isolated bone marrow cells obtained from either young or old mice were divided into aliquots for the determination of CFU-OB present in the initial isolate as well as for culture on plastic or on a preservation ECM made by marrow stromal cells from young animals (young preservation ECM) or from old animals (old preservation ECM). After the 7-day culture period, nonadherent cells were removed, and adherent cells were detached from the various matrices and reseeded onto plastic for colony assay.

The number of MSCs in marrow of old mice, as measured by their ability to form a colony of osteoblastic cells (CFU-OB), was 5-10% lower as compared to young mice. FIGS. 22A and 1B show that the frequency of CFU-OB in initial isolates from old mice was approximately 57 colonies per $10^6$ mononuclear cells (MNCs), which was only 5-10% less than those from young mice (p<0.05 from FIG. 22B). However, most MSCs and osteoblast progenitors from old mice were depleted, showing fewer CFU-OB compared to those from young mice, after the 7-day culture on ordinary tissue culture plastic. Importantly, the decreased number of CFU-OB from old mice was restored when they were cultured on a young-ECM (FIGS. 22A & 22B). In contrast, defects in the self-renewal and bone formation capacity of old MSCs were not corrected by exposure to an old-ECM.

Interestingly, the numbers of CFU-OB from both young and old mice were significantly decreased after culture on old-ECM, as compared to those cultured on young-ECM (FIGS. 22A & 22B). The replication of MSCs or colony forming cells during 7 days of culture on plastic, young-, or old-ECM was determined by measuring the fold increase in CFU-OB shown in Table 6. The number of CFU-OB in initial isolate was not significantly different between young and old mice (Table 6; FIG. 22C). After 7 days of culture on plastic, the numbers of CFU-OB from young mice increased 2.0-fold, whereas those from old mice decreased (0.5-fold) (FIG. 22C). Parallel experiments were performed with MSCs cultured for 7 days on either young- or old-ECM. Under the former condition, the replication of MSCs from both young and old mice increased indistinguishably (15.6- and 12.6-fold, respectively) (Table 6; FIG. 22C). Under the latter condition, the replication of MSCs from young and old mice increased only 3.0- and 3.4-fold, respectively, a dramatic decrease when compared to MSCs cultured on young-ECM (FIG. 22C).

To determine whether the restoration of age-related MSC replication was associated with the reduction of oxidative stress, the intracellular level of reactive oxygen species (ROS) was also measured in the above experiments. It was found that ROS was 20% higher in cultured bone marrow cells from old mice than young mice when cultures were performed on plastic (p<0.05 from FIG. 22D). In parallel cultures maintained on the young-ECM, ROS levels in bone marrow-cultured cells from both young and old mice were dramatically reduced 30 to 50% when compared to those maintained on plastic as well as the old-ECM (FIG. 22D).

Determination of Colony-Forming Unit-Osteoblast (CFU-OB) Replication Capacity.

Replication of CFU-OB (Table 6) was determined by comparing the number present in the initial femoral marrow cell isolate to the number present after 7 days of culture on the various matrices as described previously (Chen et al., 2007). Freshly isolated bone marrow cells were pooled from 3 to 6 mice and an aliquot was used to determine CFU-OB number. The total number of CFU-OB present in the initial isolate was calculated by multiplying the number of CFU-OB per cell seeded by the number of cells present in the isolate. Portions of the remaining freshly isolated bone marrow cells were cultured in standard culture medium in 6-well plates at $7\times10^6$ cells per 10 cm$^2$ well on either tissue culture plastic, or on ECMs prepared from either young or old mice. After 7 days of culture to allow replication, non-adherent cells were removed; adherent cells were then detached with collagenase. The cells were then counted and replated for quantification of CFUOB. The same number of cells was seeded onto plastic for determination of CFU-OB number regardless of the substratum used for expansion. The total number of CFU-OB after expansion (had the entire femoral marrow isolate been cultured on plastic or a particular ECM) was calculated by multiplying the number of CFU-OB obtained per cell seeded by the number of cells obtained after expansion, and then dividing the result by the fraction of the initial marrow isolate used for expansion (Table 6).

cells were added immediately in 3 ml of standard culture medium containing 1 mM L-ascorbate-2-phosphate (Wako Chemicals, Richmond, Va.). One-half of the medium was replaced every 5 days. After 25 days of culture, CFU-OB colonies were visualized with Von Kossa staining. Measurements of intracellular reactive oxygen species (ROS) Intracellular ROS generation was measured with 2′,7′-dichlorodihydrofluorescein diacetate (H2DCFDA) using a ROS Assay Kit (Invitrogen, Eugene, Oreg., USA) following the manufacturer's recommendations. ROS levels were expressed as arbitrary units (AU) of DCF fluorescence per $10^5$ cells.

The data reveals that defects in the replication of aged MSC were completely restored by exposure to a preservation ECM made by marrow stromal cells from young animals. Under this condition, both number and replication of MSCs were dramatically increased regardless of age. More importantly, such improvement was extremely diminished when cells (from either young or old mice) were cultured on preservation ECM made by marrow stromal cells from old animals. Consistent with the results from the in vitro studies, increased skeletal tissue formation occurred by MSCs (from either young or old mice) expanded on young-ECM, but not on old-ECM. In particular, both young and old MSCs pre-cultured on old-ECM generated more adipose tissue in vivo, suggesting that old-ECM may accelerate aging of MSCs. Taken together, the uniqueness of the present study is to provide strong evidence that the aging of

TABLE 6

Analysis of CFU-OB After Culture On Plastic, Young- Or Old-ECM

|  | Initial Marrow Cell Isolate | |
| --- | --- | --- |
|  | 3M | 18M |
| Frequency of CFU-OB in initial marrow cell isolate (per $10^6$ cells) | 64 ± 4 | 57 ± 3 |
| Total CFU-OB in initial marrow cell isolate ($\times10^3$ per femur)* | 0.887 ± 0.049 | 1.038 ± 0.453 |

|  | After expansion | | | | | |
| --- | --- | --- | --- | --- | --- | --- |
|  | Plastic | | Young-ECM | | Old-ECM | |
|  | 3M | 18M | 3M | 18M | 3M | 18M |
| Average no. cells after expansion ($\times10^6$ per well) | 0.5 | 0.25 | 2.2 | 1.9 | 0.8 | 1.1 |
| No. CFU-OB after expansion ($\times10^3/10^6$ cells) | 2.0 ± 0.1 | 0.8 ± 0.2 | 3.1 ± 0.1 | 2.7 ± 0.5 | 1.7 ± 0.6 | 1.3 ± 0.3 |
| Total CFU-OB after expansion ($\times10^3$)† | 1.0 ± 0.1 | 0.2 ± 0.1 | 6.9 ± 0.3 | 5.1 ± 0.9 | 1.3 ± 0.5 | 1.4 ± 0.3 |
| Total CFU-OB after expansion of marrow cells isolate per femur ($\times10^3$)‡ | 2.0 ± 0.1 | 0.5 ± 0.1 | 13.8 ± 0.6 | 13.0 ± 2.2 | 2.7 ± 1.0 | 3.6 ± 1.0 |
| Fold change during expansion$^a$ | 2.3 ± 0.1** | 0.5 ± 0.2 | 15.6 ± 1.1†† | 12.6 ± 4.4†† | 3.0 ± 1.0 | 3.4 ± 1.7 |

*Number of CFU-OB per $10^6$ cells multiplied by average number of BMNCs per femur (3M, $1.4 \times 10^7$ BMNCs per femur, and 18M, $1.8 \times 10^7$ BMNCs per femur).
†Number of CFU-OB per $10^6$ cells multiplied by average number of cells obtained per well after expansion.
‡Total number of CFU-OB after expansion divided by fraction of cells used for expansion (3M, 0.5; 18M, 0.39)
$^a$Total CFU-OB after expansion of marrow cells isolate per femur divided by the total amount of CFU-OB present in the initial isolate per femur
**$p < 0.05$ vs 18M on plastic
††$p < 0.05$ by ANOVA vs fold change of CFU-OB after expansion on plastic, and old-ECM The replication MSCs expanded on the various substrata was presented by fold changes as previously described (Chen et al., 2007), which was determined by dividing the calculated total number of CFU-OB after expansion by the total number of CFU-OB present in the initial femoral marrow cell isolate (Table 6).

The CFU-OB assay has been described previously (Chen et al., 2007). Cells were placed into 6-well plates at $1\times10^6$ cells/10 cm$^2$ well for primary CFU-OB (before expansion) or at $5\times10^4$ cells/10 cm$^2$ well for secondary CFU-OB (after expansion), incubated for 4 hrs at 37° C. to allow attachment of adherent cells, and washed twice with PBS to remove nonadherent cells. Then, $3\times10^6$ irradiated guinea pig feeder the endogenous ECM as surrounding tissue is the major determinant driving MSCs to age. Moreover, aged MSCs themselves can also alter the composition of the preservation ECM. Clearly, the data suggested that preservation ECM prepared from cultured bone marrow stromal cells from old animals contained more mineral phosphate and less collagen than those from young animals. It has been known that calcium phosphate particles impair osteoblast progenitor viability and proliferation (Pioletti et al., 2000), which could explain that the capacity of young MSCs to self-renew and generate skeletal tissue was diminished after exposure to old preservation ECM.

A Young-Preservation Matrix Enriches Bone Marrow Adherent Cells that Exhibit High Levels of Telomerase and ATP Activities.

Figure 27:
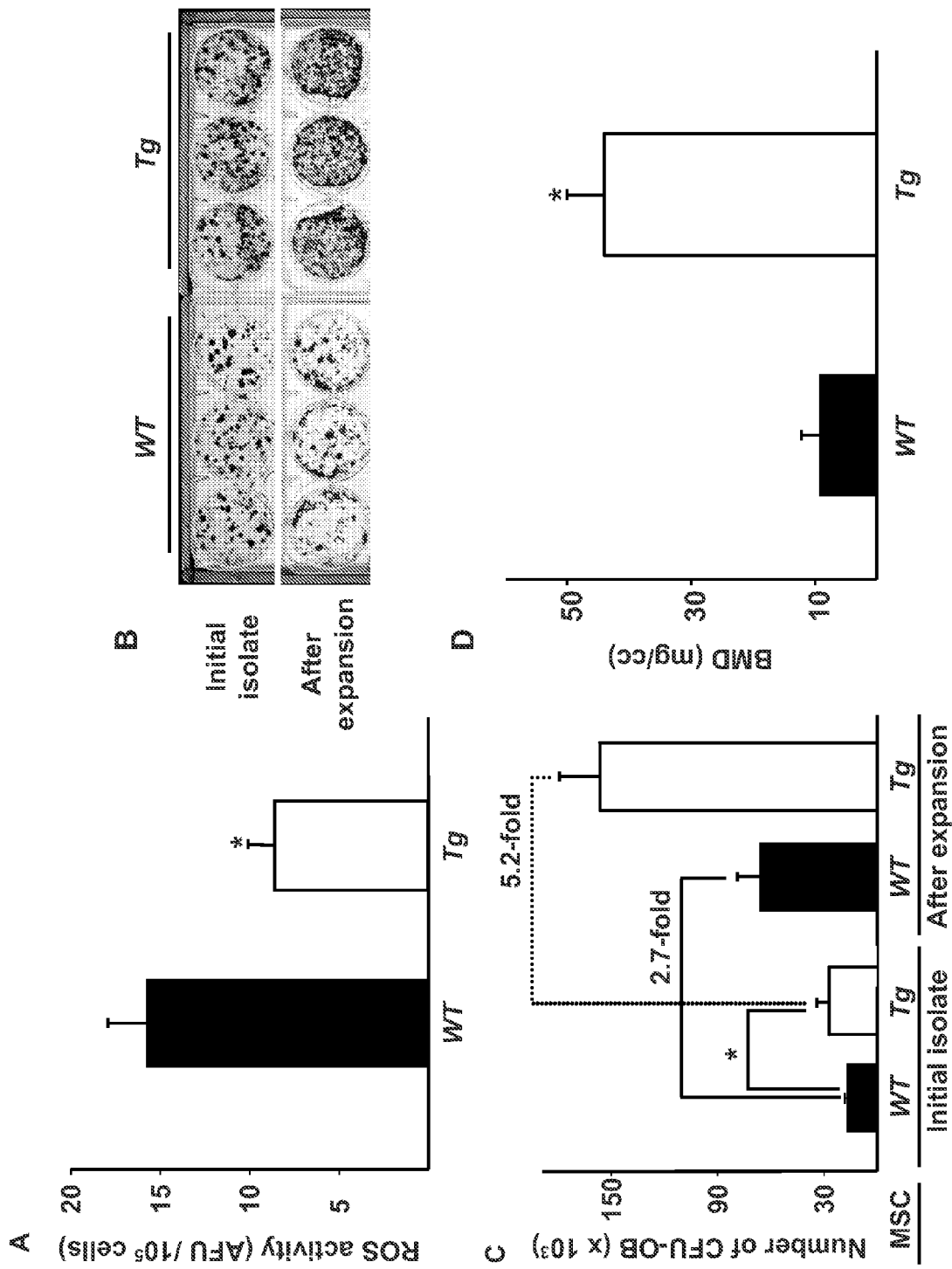
FIGS. 27A-D MSCs from Tg(Gpx4)$^{+/0}$ mice exhibit increased replication as well as skeletal tissue formation.

Since telomerase is required for the extension of telomere length associated with cellular life-span and evidence that MSCs maintained on the preservation ECM retain a high level of telomerase activity (Lai et al., 2009; Cong and Shay, 2008), the inventor measured intracellular telomerase activity of cultured cells on the various matrices. Indeed, cells either from young or old mice exhibited significantly higher levels of telomerase activity when they were cultured on a young-ECM versus those cultured on an old-ECM as well as on plastic (p<0.05 from FIG. 23A). There was no significant difference in the levels of telomerase activity between young and old cells when they both were cultured on the young-ECM. In view of a significant correlation between ATP activity and number of highly functional stem cells (Reems et al., 2008), the intracellular ATP activity of cultured cells was measured in the parallel experiments. Overall, both young and old cells cultured on preservation ECM showed significantly increased ATP levels as compared to plastic (p<0.05 from FIG. 23B). However, the increase in the levels of ATP was approximately 1.5 to 2-fold greater when cultured on young-ECM compared to old-ECM, regardless of aging (FIG. 27B). To further determine whether these results were related to the alteration of cellular composition caused by aging and/or the various culture conditions, wethe inventor also examined a series of MSC-related markers including SSEA-4, CD44, CD90, and Sca-1 (Kannagi et al., 1983; Adewumi et al., 2007), and a hematopoietic cell marker CD45. The results indicated that levels of all markers expressed by young cells were higher than those expressed by old cells in initial cell isolate (Table 7). After culture on the various matrices, cells maintained on either young- or old-ECM contained approximately 23% SSEA-4 positive cells, which was significantly higher than when these cells were maintained on plastic (p<0.05 from Table 7). Unexpectedly, the inventor found that there were no significant differences in the proportions of those positive cells after culture on young-ECM versus old-ECM.

collagenase. The pre-cultured cells ($1\times10^6$) from the various matrices were resuspended in 200 μl of lysis buffer, and incubated on ice for 30 min. The protein samples were centrifuged at 12,000×g for 30 minutes at 4° C. After the protein concentration was determined, the aliquots were quick-frozen, and stored at −80° C. for assay. The heat inactivated cell extract were used as a negative control. Experiments were performed in triplicate, and telomerase levels were expressed as amoles per $10^6$ cells. To measure intracellular ATP levels, the assays were performed with ATP standard curves including high and low controls according to the manufacturer's instructions (HemoGenix, Inc., Colorado Springs, Colo., USA). Briefly, $1\times10^6$ pre-cultured cells were collected from the various matrices. 2,500, 5,000, and 7,500 cells/100 μl per well were added to the wells of the 96-well plate provided with the kit. Experiments were performed in triplicate, and ATP levels were expressed as μmoles per $10^6$ cells.

In order to further demonstrate the functional potential of progenitors, the inventor compared intracellular telomerase and ATP activities from cells cultured on the various matrices since the former is associated with cellular life-span and the latter is directly correlated to the proliferation status of stem cells (Cong and Shay, 2008; Reems et al., 2008). Based on the levels of telomerase and ATP activities, it was suggested that a high quality of stem cells was enriched from bone marrow cells by exposure to a young-ECM, supporting the observation that young-ECM promoted MSCs for osteoblastogenesis in vitro and in vivo. To test the related probability that cellular compositions varied with age and that a different cell population could be selectively enriched by exposure to the different matrices, the inventor measured several MSC related markers such as SSEA-4, CD44, CD90, and Sca-1. Unexpectedly, the inventor found no significant difference in the proportion of those positive cells when cells were maintained on young-versus an old-ECM. Although SSEA-4 originally identified as an early embryonic glycolipid antigen, has been utilized to identify MSCs from bone marrow (Kannagi et al., 1983; Gang et al., 2007), the previous studies indicate that SSEA-4 is mainly expressed

TABLE 7

FACs Analysis Before And After Bone Marrow Cells Cultured On The Various Matrices

| % | Initial marrow cell isolate | | Plastic | | Young-ECM | | Old-Ecm | |
|---|---|---|---|---|---|---|---|---|
| | 3M* | 18M | 3M | 18M | 3M | 18M | 3M | 18M |
| SSEA-4+ | 37 ± 4 | 18 ± 3 | 12 ± 2† | 15 ± 2† | 22 ± 3 | 24 ± 2 | 24 ± 2 | 25 ± 3 |
| CD44+ | 67 ± 5 | 45 ± 4 | 84 ± 8 | 79 ± 6 | 88 ± 7 | 88 ± 6 | 86 ± 8 | 85 ± 7 |
| CD90+ | 18 ± 3 | 11 ± 2 | 20 ± 3 | 25 ± 3 | 11 ± 2 | 13 ± 2 | 17 ± 3 | 12 ± 3 |
| Sca-1+ | 37 ± 3 | 26 ± 3 | 50 ± 4 | 48 ± 3 | 50 ± 3 | 49 ± 4 | 63 ± 7 | 54 ± 5 |
| CD45+ | 63 ± 7 | 46 ± 5 | 72 ± 8† | 76 ± 6† | 89 ± 8 | 90 ± 9 | 86 ± 7 | 89 ± 9 |

*p < 0.05 vs 18M initial marrow cell isolate; and
†p < 0.05 vs cells cultured on Young- or Old-ECM.

Measurements of Intracellular Telomerase Activity and ATP Concentration.

Intracellular telomerase activity was measured using the quantitative telomerase detection kit (Allied Biotech, Inc., Twinsburg, Ohio, USA) according to the manufacturer's instructions. Briefly, freshly isolated bone marrow cells from either young or old mice were seeded at $7\times10^6$ cells per 10 cm² well onto tissue culture plastic, or onto young- or old-ECM, and cultured for 7 days. After rinsing with PBS to remove nonadherent cells, adherent cells were detached with by dividing cells that do not necessarily represent pluripotent MSCs (Lai et al., 2009). Thus, the findings suggest that these markers may not be specific enough to define highly functional MSCs.

The Preservation Matrix Promotes Bone-Forming Capacity of MSCs from Either Young or Old Mice.

Next, the inventor compared the influence of culture on young-versus old-ECM on the capacity of old MSCs or young MSCs to form bone in vivo using an implantation assay, as previously described (Chen et al., 2007). After 7 days of culture of either young or old bone marrow cells on plastic, or on young- or old-ECM, 1×10⁶ cells were loaded onto Gelfoam and implanted subcutaneously into the dorsal surface of immunodeficient mice. The implants were harvested 8 weeks following implantation. Bone formed was quantified using µCT. As shown in FIG. 24A as well as Table 8, no or less bone was generated from old MSCs pre-cultured on plastic, or old-ECM, respectively. In contrast, old MSCs as well as young MSCs pre-cultured on young-ECM formed the same amount of bone as determined by bone mineral density (BMD), which was ~2 to 3 times more than that formed by young MSCs pre-cultured on plastic or old-ECM. Histological analysis showed that either young cells or old cells pre-cultured on old-ECM generated skeletal tissues with many large pale spaces, formerly filled by large fat droplets, suggesting formation of more adipose tissue than with cells pre-cultured on young-ECM (FIG. 24A, right panels). In a second experiment shown in FIG. 24B, old MSCs formed less bone than young MSCs when they both were cultured on plastic. Consistent with the previous experiment, increased skeletal tissue formation by MSCs (from either young or old mice) expanded on young-ECM was determined by the percentage of bone volume in the total area of ossicle. Implantation of cells pre-cultured on a young-ECM generated 1.8-2.8 times more cancellous bone than did cells pre-cultured on plastic (FIG. 36B, right panel). These findings suggested that culture of old MSCs on a young-ECM improved their quantity and quality.

Figure 26:
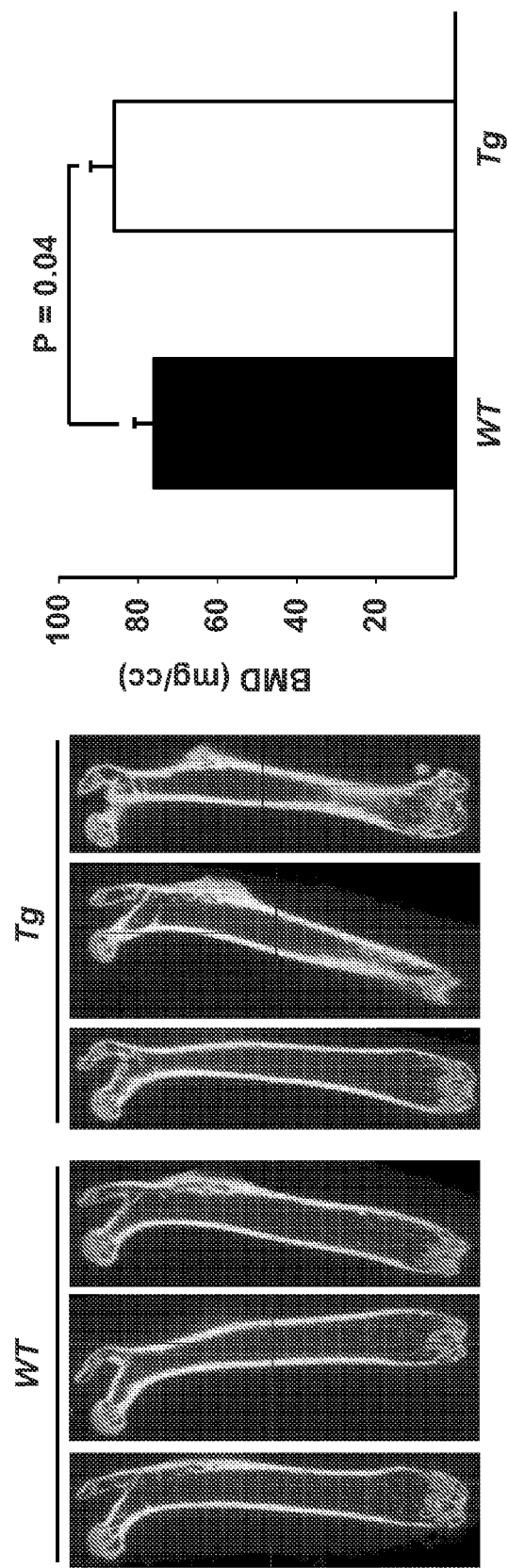
FIG. 26 Tg(Gpx4)$^{+/0}$ mice exhibit increased BMD in the femur compared to wt mice. Femoral BMD in 3-month old female Tg(Gpx4)$^{+/0}$ mice and wt littermates was measured using an eXplore Locus RS Small Animal MicroCT (μCT) scanner (GE Healthcare, London, Ontario). A. Images of μCT of femora from Tg(Gpx4)$^{+/0}$ mice and wt littermates. B. Femoral BMD in Tg(Gpx4)$^{+/0}$ mice and wt littermates. *p<0.05, n=3 vs. wt littermates.

[Tg(Gpx4)$^{+/0}$] that has been reported to reduce oxidative stress-induced apoptosis (Ran et al., 2004). In the present study, the inventor found that bone mass, measured with BMD, in the femur of 3-month old Tg(Gpx4)$^{+/0}$ mice was significantly higher than that of wt littermates ($p<0.05$ from FIG. 26). Indeed, ROS levels from freshly isolated bone marrow cells from Tg(Gpx4)$^{+/0}$ mice was ~50% less than those from wt littermates (FIG. 27A). Consistent with decreased ROS levels, the initial number of MSCs from Tg(Gpx4)$^{+/0}$ mice was significantly higher than that of MSCs from wt littermates (FIGS. 27B & $p<0.05$ from 27C). Importantly, the replication of MSCs from Tg(Gpx4)$^{+/0}$ mice during 7 days of culture on plastic was markedly increased, as compared to that of MSCs from the wt (5.2-fold vs. 2.7-fold, respectively) (FIGS. 27B & 27C). To show the capacity of MSCs from Tg(Gpx4)$^{+/0}$ mice to generate skeletal tissue, the inventor used an implantation assay. The inventor found that BMD in bone ossicles generated by MSCs or osteoblast progenitors from Tg(Gpx4)$^{+/0}$ mice was remarkably increased, as compared to that generated by cells from wt littermates (FIG. 27D).

Analysis of Bone Mineral Density (BMD) in the Femur of Tg(Gpx4)+/0 Mice Versus wt Littermates.

Femora were dissected from 3-month old female Tg(Gpx4)$^{+/0}$ mice or wt littermates. After removal of soft tissue, the femora were stored in 70% ethanol until analyzed. The femora were scanned on volumetric µCT at 27-µm³ voxel resolution using an eXplore Locus RS Small Animal

TABLE 8

Measurement Of Bone Mineral Density

| | Plastic | | Young-ECM | | Old-ECM | |
|---|---|---|---|---|---|---|
| Expansion | 3M | 18M | 3M | 18M | 3M | 18M |
| BMD (mg/cc) | 13 15 9 | ND ND ND | 43 32 46 | 29 67 34 | 20 22 24 | 1.2 ND ND |
| Mean ± SD | 12.3 ± 3.1 | | 40.3 ± 7.3* | 43.3 ± 20.0 | 22.0 ± 2.0† | |

Figure 25:
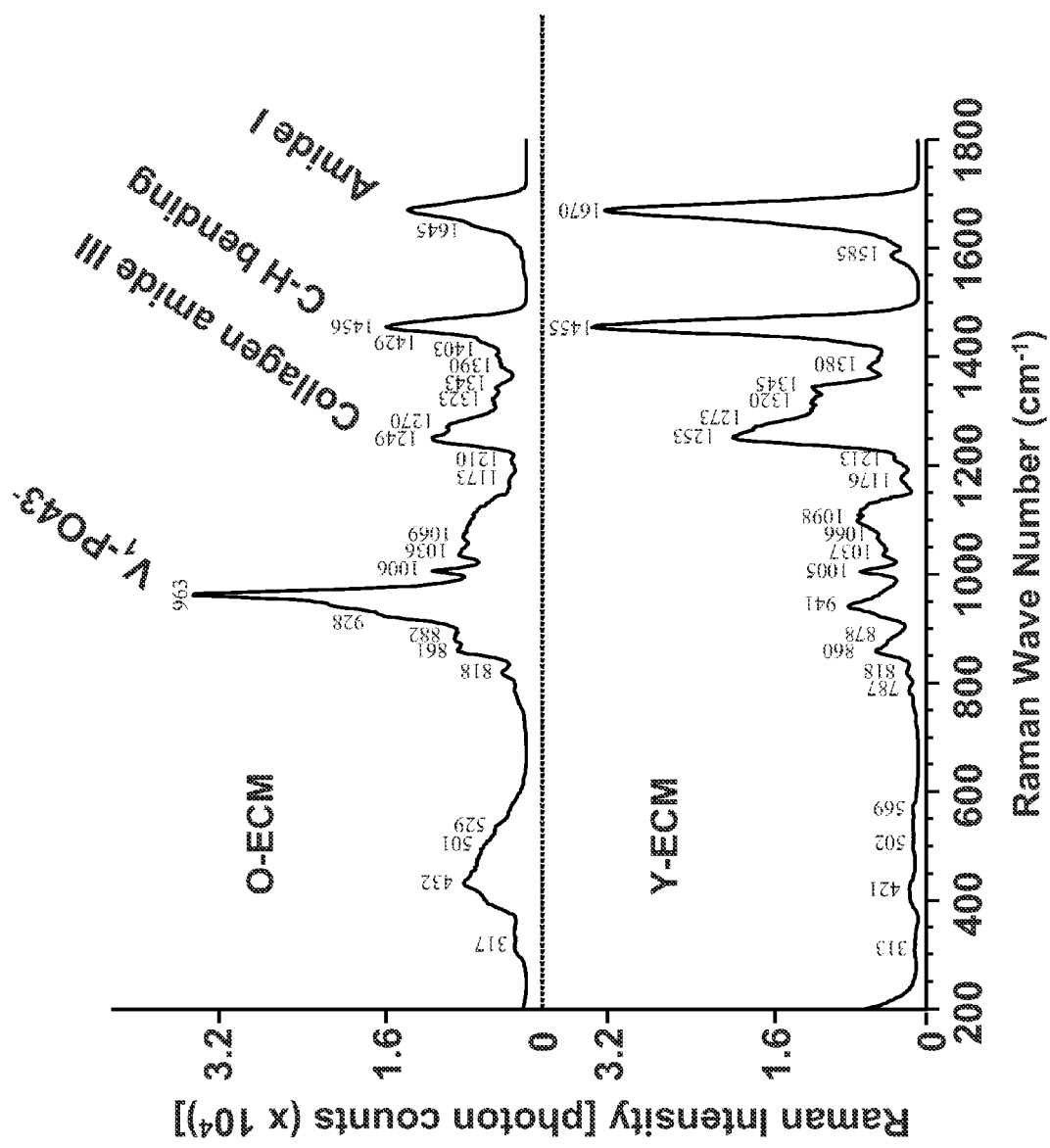
FIG. 25 Raman spectrum: the differential composition of young-ECM versus old-ECM. Five randomly selected areas were imaged in each sample, and 6 samples were examined for either young- or old-ECMs prepared from the independent experiments. The spectra from young- or old-ECMs were averaged, respectively. The graph was represented as an ensemble average of Raman spectrum. The old-ECM exhibited a sharp peak at ~960 cm$^{-1}$ related to mineral phosphate (V1-PO4 3−), and a few smaller peaks at 1249 and 1270 cm-1, ~1455 cm$^{-1}$ and ~1670 cm$^{-1}$ corresponding to collagen amide III, CH bending and amide I, respectively, as compared to the young-ECM.

*$p < 0.05$ vs young cells (3M) expanded on Plastic, or on Old-ECM; and
†$p < 0.5$ vs young cells (3M) expanded on Plastic Due to the differential features of MSCs when exposed to young-versus old-preservation ECM, the inventor compared the composition of these two preservation ECMs using confocal Raman microscopy (FIG. 25). Compared to young-ECM, old-ECM exhibited a distinct, sharp Raman peak at 960 cm-1, consistent with symmetric stretching vibrations of phosphate ions ($V_1$—$PO_4^{3-}$), suggesting that mineral was deposited on the ECM. The presence of a broad bump around 430 cm-1 (hydroxyapatite $V_2$—$PO_4^{3-}$) and the absence of a well-defined characteristic peak of bone phosphate at 589 cm-1 ($V_4$—$PO_4^{3-}$) indicated that the mineral deposited in ECM may not be as well-organized as in bone. In contrast, no evidence of mineral phosphate was observed in young-ECM. In addition, young-ECM showed high peaks at 1249 and 1270 cm$^{-1}$, ~1455 cm$^{-1}$ and ~1670 cm$^{-1}$ corresponding to collagen amide III, C—H bending and amide I, respectively, which suggested that young-ECM contained more collagens. Apparently, the ratio of mineral to collagen was higher in the old-ECM than in the young-ECM.

Since the improvement of MSC self-renewal by exposure to a young-ECM was associated with the reduction of ROS, it was necessary to further assess whether a decrease in ROS level helped facilitate MSC self-renewal. Therefore, the inventor examined the replication of MSCs from transgenic mice (C57BL6) overexpressing glutathione peroxidase 4

µCT scanner (GE Healthcare, London, Ontario) for 10 frames per view for a total of 125 min of image acquisition time. Images were reconstructed with the manufacturer's proprietary EVSBeam software and calibrated to standard CT number, measured in Hounsfield Units (HU), and furthermore calibrated to permit determination of equivalent mass of hydroxyapatite. The bone analysis was performed on MicroView (available on the world wide web at microview.sourceforge.net.). Two-dimensional transfer function (2DTF) visualizations were performed on the obtained datasets with software from the University of Utah Scientific Computing Institute (Imagevis3D, available on the world wide web at sci.utah.edu/cibc/software).

Increasing evidence indicates that the continuous production of intracellular reactive oxygen species (ROS), including superoxide anions, hydroxyl radicals and hydrogen peroxide, are a major determinant of life span (Balaban et al., 2005). Although the mechanisms underlying the influence of life span are not completely understood, increased ROS is thought to cause cell death and accelerate the aging process by, at least in part, stimulation of stem cells or progenitors into a state of replicative senescence in which they are growth-arrested (Kirkwood, 2005). Recent studies in hematopoietic stem cells have shown that a high level of ROS is associated with loss of stem cell self-renewal and increased differentiation as well as their apoptosis (Tothova et al., 2007). Moreover, culture of MSCs under low oxygen tension (3%) to mimic the microenvironment of the bone marrow enhances MSC "stemness" (D'Ippolito et al., 2006). Evidence obtained from the present studies showed that intracellular level of ROS was higher with a decrease in the number of CFU-OB, and vice versa. Fascinatingly, in cultures maintained on young-ECM, ROS levels from both old and young mice were reduced 50% and 30%, respectively. Under this condition, the number of CFU-OB from old and young mice increased 13- and 16-fold, respectively. In contrast, ROS levels were elevated in cultured MSCs (from either young or old animals) on old-ECM, which was accompanied by a decrease in the number of CFU-OB. To further confirm whether preservation ECM restored the replication of aged MSCs by means of reducing ROS, the inventor tried the alternative approach of attempting to enhance antioxidant defenses through genetic modification—mouse overexpression of glutathione peroxidase 4 [Tg(Gpx4)$^{+/o}$ mice]. Antioxidant enzymes mainly include superoxide dismutase (SOD), catalase and glutathione peroxidase (Gpx), which act to remove ROS production by free radical reactions (McCord and Fridovich, 1969a; McCord and Fridovich, 1969b). Based on differential tissue-specific distribution, the Gpx family has been classified into at least 4 types (Brigelius-Flohe, 1999). It is considered that Gpx4 plays an important role in protecting against oxidative stressinduced apoptosis via the stabilization or the repair of mitochondrial membranes as well as cellular membranes (Brigelius-Flohe, 1999). The present studies showed that intracellular ROS levels in bone marrow cells from Tg(Gpx4)$^{+/o}$ mice were reduced 40-50%, and the capacity for replication as well as bone generation of MSCs from Tg(Gpx4)$^{+/o}$ mice was markedly enhanced, as compared to wt mice. These findings indicate that increased oxidative stress is associated with defects in the self-renewal of aged MSCs and osteoblast progenitors, and that such defects may be corrected by reducing ROS. Although Tg(Gpx4)$^{+/o}$ mice had only a marginally increased BMD compared to wt mice at 3 months of age, the inventor speculate that Tg(Gpx4)$^{+/o}$ mice may delay their bone loss during aging.

Materials and Methods

Animals.

C57BL6 female mice, 3-month old (young) and 18-month old (old), were obtained from The National Institute on Aging (NIA). The generation of glutathione peroxidase 4 (Gpx4) transgenic mice [Tg(GPX4)$^{+/o}$] was previously reported (Yant et al., 2003). Tg(GPX4)$^{+/o}$ mice were generated using a human endogenous GPX4 gene, and showed overexpression of Gpx4 in all tissues (Yant et al., 2003; Ran et al., 2004). It has been reported that Tg(GPX4)$^{+/o}$ mice are resistant to the administration of diquat that induces hepatotoxicity and apoptosis, as compared to wild type (wt) mice (Ran et al., 2004). In the present study, 3-month old C57BL6 female Tg(GPX4)$^{+/o}$ mice were used. All animal procedures were approved by the UTHSCSA Institutional Animal Care and Use Committee.

Flow Cytometry.

Anti-SSEA-4 antibodies were purchased from R&D Systems (Minneapolis, Minn., USA). Anti-CD44, CD90, and Sca-1 antibodies were purchased from eBioscience (San Diego, Calif., USA). Anti-CD45 antibodies were purchased from BD Bioscience (San Jose, Calif., USA). Single-cell suspensions (1×10$^6$) were incubated in 100 µl of tested antibodies (10 µg/ml) for 30 minutes at 4° C. The stained cells were washed twice in staining buffer (PBS containing 5% FCS and 0.01% sodium azide) and incubated in 20 µg/ml of FITC-conjugated goat anti-mouse IgG for 20 minutes at 4° C. The cells were then washed twice with staining buffer and either immediately analyzed or fixed with 1% paraformaldehyde in PBS and analyzed within 96 hours using a Becton Dickinson FACStarplus flow cytometer with 10,000 events, collected for each sample. The percentage of positively stained cells was determined from fluorescence-activated cell sorting (FACS). Cells were stained with isotype IgG as a negative control.

In Vivo Bone Formation.

Freshly isolated marrow cells from either young or old mice, pooled from 3 to 6 mice for each age, were seeded at 7×10$^6$ cells per 10 cm$^2$ well onto tissue culture plastic or marrow cell-derived preservation ECM prepared by either young or old mice, and cultured for 7 days. After rinsing with PBS to remove nonadherent cells, adherent cells were detached with collagenase. The cells (1×10$^6$) were loaded onto Gelfoam (Pharmacia & Upjohn Company, MI, USA), and implanted subcutaneously into the dorsal surface of 10-weekold immunodeficient beige mice (NIH-bg-nu-xid, Harlan Sprague Dawley, Indianapolis, Ind.), as previously described (Krebsbach et al., 1997; Bi et al., 2005). Cells pre-cultured on tissue culture plastic were implanted on the left side, and cells pre-cultured on marrow derived-ECM were implanted on the right side of each animal. As a negative control, a Gelfoam vehicle without cells was implanted into the mouse. The implants were harvested after 8 weeks, and scanned using an eXplore Locus RS Small Animal MicroCT (XT) scanner (GE Healthcare, London, Ontario). The data obtained were quantitatively analyzed for bone content using software with optional bone analysis plug-ins (MicroView@ version 2.1.2, GE Healthcare, http://microview.sourceforge.net). For histological analysis, implants were fixed in 10% phosphate-buffered formalin at 4° C. for 24 hrs, decalcified with 5% EDTA at room temperature for 1-2 weeks, and embedded in paraffin. Each ossicle was bisected, and 3 sections (10 µm thick) were cut, starting at the bisection point of each half-ossicle at 50 µm intervals to yield a total of 12 sections for each ossicle. Sections were stained with H&E. To determine the capacity of MSCs from Tg(Gpx4)$^{+/o}$ mice to generate skeletal tissue in vivo, the same procedure was followed except that cells were only expanded on tissue culture plastic for 7 days.

Measurement of the Raman Spectra of Old-ECM Versus Young-ECM.

Cell-free preservation ECMs generated on a plastic coverslip were carefully scraped off, collected and stored in PBS at 4° C. until analyzed. The Raman spectrum of the preservation ECM in the fingerprint region between the wavenumber of 200 and 1800 cm-1 was acquired with a Renishaw 2000 Raman microscope (Gloucestershire, UK). Five randomly selected areas were imaged in each sample, and 6 samples were examined for either young- or old-ECMs prepared from the independent experiments. The spectra from young- or old-ECMs were averaged, respectively.

Statistical Analysis.

All data are presented as mean±standard deviation, with n=3 or 6, depending on the experiment. Statistical analyses were done using Student's t test or one-way ANOVA with significance at p<0.05. All results were reproduced in at least 3 independent experiments.

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbott, *Nature*, 424:870-872, 2003.
Abe et al., *J. Bone Miner Res.*, 15:663-673, 2000.
Adewumi et al., *Nat. Biotechnol.*, 25:803-816, 2007.
Aubin and Triffitt, In: *Principles of bone biology*, Bilezikian et al., (Eds.), 2$^{nd}$ Ed., San Diego, Academic Press, 59-81, 2002.
Bakay et al., *BMC Bioinformatics*, 3:4, 2002.
Baksh et al., *J. Cell Mol. Med.*, 8:301-316, 2004.
Balaban et al., *Cell*, 120:483-495, 2005.
Banerjee and Bhonde, *Med. Hypotheses*, 68:1247-1251, 2007.
Banfi et al., *Exp. Hematol.*, 28:707-715, 2000.
Behonick and Werb, *Mech. Dev.*, 120:1327-1336, 2003.
Bennett et al., *Histol. Histopathol.*, 16:603-611, 2001.
Bi et al., *J. Biol. Chem.*, 280:30481-30489, 2005.
Bianchi et al., *Exp. Cell Res.*, 287:98-105, 2003.
Brigelius-Flohe, *Free Radic. Biol. Med.*, 27:951-965, 1999.
Campbell et al., *J. Clin. Invest.*, 75:2085-2090, 1985.
Campisi, *Cell*, 120:513-522, 2005.
Chen et al., *J. Bone Miner Res.*, 17:331-34, 2002.
Chen et al., *FASEB J.*, 18:948-958, 2004.
Chen et al., *Bone Miner Res.* 22:1943-1956, 2007.
Chow et al., *Biophys. J.*, 81:675-684, 2001.
Clark and Keating, *Ann. NY Acad. Sci.*, 770:70-78, 1995.
Cong and Shay, *Cell Res.*, 18:725-732, 2008.
Corsi et al., *J. Bone Miner Res.*, 17:1180-1189, 2002.
Cukierman et al., *Science*, 294:1708-1712, 2001.
D'Ippolito et al., *Bone*, 39:513-522, 2006.
Dallas et al., *J. Biol. Chem.*, 277:21352-21360, 2002.
Delany and Canalis, *Endocrinology*, 142:1561-1566, 2001.
Deng et al., *Stem Cells*, 24:1054-1064, 2006.
Dennis et al., *J. Bone Miner Res.*, 14:700-709, 1999.
Di Gregorio et al., *J. Clin. Invest.*, 107:803-812, 2001.
DiGirolamo et al., *Br. J. Haematol.*, 107:275-281, 1999.
Drzeniek et al., *Biochem.*, 3 327 (Part 2):473-480, 1997.
Engler et al., *Cell*, 126:677-689, 2006.
Ferrari et al., *Science*, 279:1528-1530, 1998.
Freund et al., *Stem Cell Dev.*, 15:815-829, 2006.
Friedenstein et al., *Transplantation*, 17:331-339, 1974.
Fuchs et al., *Cell*, 116:769-778, 2004.
Gang et al., *Blood*, 109:1743-1751, 2007.
Gleizes et al., *Stem Cells*, 15:190-197, 1997.
Gordon, *Br. Haematol.*, 7:1-4, 1988.
Gospodarowicz et al., *J. Cell Biol.*, 99:947-961, 1984.
Grayson et al., *Biotechnol. Prog.*, 20:905-912, 2004.
Gronthos et al., *J. Bone Miner Res.*, 18:716-722, 2003.
Hamilton and Campbell, *Anat. Rec.*, 231(2):218-24, 1991.
Hildebrand et al., *Biochem. J.*, 302(Part 2):527-534, 1994.
Hocking et al., *Matrix Biol.*, 17:1-19, 1998.
Horwitz et al., *Cytotherapy*, 4:511-512, 2002.
Izadpanah et al., *Cancer Res.*, 68:4229-4238, 2008.
Jarrahy et al., *Am. Physiol. Cell Physiol.*, 289:C408-C414, 2005.
Jiang et al., *Nature*, 418:41-49, 2002.
Kannagi et al., *EMBO J.*, 2:2355-2361, 1983.
Kassem, *Ann. NY Acad. Sci.*, 1067:436-442, 2006.
Kim et al., *Arch. Pharm. Res.*, 32:117-126, 2009.
Kirkwood, *Cell*, 120:437-447, 2005.
Klein, *Experientia*, 51:914-926, 1995.
Knopp et al., *Endocrinology*, 146:1983-1990, 2005.
Koc et al., *J. Clin. Oncol.*, 18(2):307-16, 2000.
Krebsbach et al., *Transplantation*, 63:1059-1069, 1997.
Ksiazek, Rejuvenation Res., 12(2):105-16, 2009.
Kuznetsov and Robey, *Calcif. Tissue Int.*, 59:265-270, 1996.
Lai et al., *Stem Cells Dev.*, 19(7):1095-107, 2010.
Lee et al., *Biochim. Biophys. Acta.*, 1428:300-304, 1999.
Loeffler and Potten, In: *Stem cells*, Potten (Ed.), San Diego, Academic Press. 1-27, 1997.
Lukashev and Werb, *Trends Cell Biol.*, 8:437-441, 1998.
Mao and Schwarzbauer, *J. Cell Sci.*, 118:4427-4436, 2005.
McCord and Fridovich, *J. Biol. Chem.*, 244:6049-6055, 1969a.
McCord and Fridovich, *J. Biol. Chem.*, 244:6056-6063, 1969b.
McCulloch et al., *Blood*, 77:1906-1911, 1991.
Miura et al., *J. Clin. Invest.*, 114:1704-1713, 2004.
Miura et al., *Stem Cells*, 24:1095-1103, 2006.
Moore and Lemischka, *Science*, 311:1880-1885, 2006.
Muschler et al., *J. Bone Joint Surg. Am.*, 86-A:1541-1558, 2004.
Nili et al., *Am. J. Pathol.*, 163:869-878, 2003.
Okita et al., *Nature*, 448:313-317, 2007.
PCT application PCT/US2009/047981
Peister et al., *Blood*, 103:1662-1668, 2004.
Peng et. al., *BMC Bioinformatics*, 4:26, 2003.
Petersen et al., *Science*, 284:1168-1170, 1999.
Petite et al., *Nat. Biotechnol.*, 18:959-963, 2000.
Philp et al., *Stem Cells*, 23:288-296, 2005.
Pioletti et al., *Biomaterials*, 21:1103-1114, 2000.
Pittenger et al., *Science*, 284:143-147, 1999.
Pollard and Earnshaw, In: *Cell Biology*, Pollard and Earnshaw (Eds.), Philadelphia, Saunders WB, 473-550, 2002.
Prockop, *Science*, 276(5309):71-4, 1997.
Ran et al., *J. Biol., Chem.*, 279:55137-55146, 2004.
Reems et al., *Transfusion*, 48:620-628, 2008.
Reichsman et al., *J. Cell Biol.*, 135:819-827, 1996.
Robey et al., *Bone Miner Res.*, 8(Suppl 2):S483-S487, 1993.
Rosland et al., *Cancer Res.*, 69(13):5331-9, 2009.
Rubio et al., *Cancer Res.*, 65:3035-3039, 2005.
Ruoslahti and Yamaguchi, *Cell*, 64:867-869, 1991.
Santra et al., *J. Biol. Chem.*, 277:35671-35681, 2002.
Sekiya et al., *Stem Cells*, 20:530-541, 2002.
Sethe et al., *Ageing Res. Rev.*, 5(1):91-116, 2006.
Smith et al., *Stem Cells*, 22:823-831, 2004.
Sotiropoulou et al., *Stem Cells*, 24:462-471, 2006.
Suzawa et al., *Endocrinology*, 140:2125-2133, 1999.
Sweet-Cordero et al., *Nat. Genet.*, 37:48-55, 2005.
Takahashi et al., *Cell*, 131: 861-872, 2007.
Tothova et al., *Cell*, 128:325-339, 2007.
Tufvesson and Westergren-Thorsson, *FEBS Lett.*, 530:124-128, 2002.
Vlodaysky, In: *Current Protocols in Cell Biology*, Morgan (Ed.), UNIT 104:10.4.1-10.4.14, John Wiley & Sons, NJ, 1999.
Watt and Hogan, *Science*, 287:1427-1430, 2000.
Wexler et al., *Br. J. Haematol.*, 121:368-374, 2003.
Xu et al., *Nat. Genet.*, 20:78-82, 1998.
Yamaguchi et al., *Nature*, 346:281-284, 1990.

Yang et al., *Bone*, 44:32-45, 2009.
Yant et al., *Free Radic. Biol. Med.*, 34:496-502, 2003.
Yu et al., *Science*, 318:1917-1920, 2007.

The invention claimed is:
1. A tissue-specific differentiation system comprising
a differentiation-inducing extracellular matrix generated ex vivo on a surface by culturing fibroblast cells on said surface, wherein the differentiation-inducing extracellular matrix is free of the fibroblast cells; and
differentiated cells in contact with the differentiation-inducing extracellular matrix, wherein the differentiated cells are derived from isolated stem cells seeded onto the differentiation-inducing extracellular matrix and induced to undergo differentiation into differentiated cells of the same tissue type as the fibroblast cells b cultured on the differentiation-inducing extracellular extracellular matrix;
wherein the fibroblast cells and differentiated cells are both from one of the following tissue types: neural tissue, epidermal tissue, dermal tissue, adipose tissue, cardiac tissue, kidney tissue, muscle tissue, liver tissue, cartilage tissue, pancreas tissue, tissue of the endometrium of uterus, umbilical cord tissue, or dental pulp tissue.

2. The tissue-specific differentiation system of claim 1, wherein the fibroblast cells are human or mouse fibroblast cells.

3. The tissue-specific differentiation system of claim 1, wherein the differentiation-inducing extracellular matrix is a 3D matrix.

4. The tissue-specific differentiation system of claim 1, wherein the differentiation-inducing extracellular matrix is free of feeder cells.

5. The method of claim 1, wherein the surface is a surface of a cell culture dish or plate.

6. The tissue-specific differentiation system of claim 1, wherein the isolated stem cells are from bone marrow, periosteum, trabecular bone, adipose tissue, synovium, skeletal muscle, deciduous teeth, fetal pancreas, lung, liver, amniotic fluid, umbilical cord blood and umbilical cord tissues.

7. The tissue-specific differentiation system of claim 1, wherein the isolated stem cells are naturally occurring stem cells or are engineered stern cells.

8. The tissue-specific differentiation system of claim 1, wherein the isolated stem cells are embryonic stem cells, mesenchymal stem cells or induced pluripotent stem cells.

9. A method of making a tissue-specific differentiation system comprising:
a) culturing fibroblast cells of a given tissue type ex vivo on a surface to produce a differentiation-inducing extracellular matrix;
b) removing the fibroblast cells from the differentiation-inducing extracellular matrix;
c) seeding isolated stem cells on the differentiation-inducing extracellular matrix; and
d) culturing the isolated stem cells on the differentiation-inducing extracellular matrix, thereby inducing the stem cells to differentiate into differentiated cells of the same tissue type as the fibroblast cells cultured in step (a);
wherein the fibroblast cells cultured in step and the differentiated cells produced in step (d) are both from one of the following tissue types: neural tissue, epidermal tissue, dermal tissue, adipose tissue, cardiac tissue, kidney tissue, muscle tissue, liver tissue, cartilage tissue, pancreas tissue, tissue of the endometrium of uterus, umbilical cord tissue, or dental pulp tissue.

10. The method of claim 9, further comprising:
e) treating the differentiation-inducing extracellular matrix with DNase after removal of the fibroblast cells.

11. The method of claim 9, wherein the surface is coated with fibronectin.

12. The method of claim 11, wherein step (a) comprises culturing the fibroblast cells on the surface for 15 days.

13. The method of claim 12, wherein step (a) further comprises adding ascorbic acid to the surface during the final 8 days of culture.

14. The method of claim 9, wherein removing the fibroblast cells comprises incubating the differentiation-inducing extracellular matrix with Triton X-100 containing 20 mM $NH_4OH$ in PBS.

15. The method of claim 9, wherein the fibroblast cells are of human or mouse origin.

16. The method of claim 9, wherein the differentiation-inducing extracellular matrix is a 3D matrix.

17. The method of claim 9, wherein the differentiation-inducing extracellular matrix is free of feeder cells.

18. The method of claim 9, wherein the differentiation-inducing extracellular matrix is free of target tissue-specific fibroblast cells.

19. The method of claim 9, wherein the surface is a surface of a cell culture dish or plate.

20. The method of claim 9, wherein the isolated stem cells are from bone marrow, periosteum, trabecular bone, adipose tissue, synovium, skeletal muscle, deciduous teeth, fetal pancreas, lung, liver, amniotic fluid, umbilical cord blood and umbilical cord tissues.

21. The method of claim 9, wherein the isolated stem cells are naturally occurring stem cells or are engineered stem cells.

22. The method of claim 9, wherein the isolated stem cells are embryonic stem cells, mesenchymal stem cells or induced pluripotent stem cells.

23. A method of inducing tissue-specific differentiation of isolated stem cells into a differentiated cell type comprising:
a) generating a first differentiation factor comprising a differentiation-inducing extracellular matrix by culturing fibroblast cells on a surface; and
b) contacting the isolated stem cells with the first differentiation factor, thereby inducing the stem cells to differentiate into the differentiated cell type,
wherein the differentiated cell type is of the same tissue type as the fibroblast cells, wherein the fibroblast cells have been removed from the differentiation-inducing extracellular matrix before contacting the isolated stem cells with the differentiation-inducing extracellular matrix, and wherein the fibroblast cells and differentiated cells are both from one of the following tissue types: neural tissue, epidermal tissue, dermal tissue, adipose tissue, cardiac tissue, kidney tissue, muscle tissue, liver tissue, cartilage tissue, pancreas tissue, tissue of the endometrium of uterus, umbilical cord tissue, or dental pulp tissue.

24. The method of claim 23, wherein the differentiated cell type is a neuron, epithelial cell, dermal cell, adipocyte, cardiomyocyte, renal cell, myocyte, hepatocyte, chondrocyte, islet cell, endothelial cell, or dental pulp cells.

25. The method of claim 23, wherein the fibroblast cells are human or mouse fibroblast cells.

26. The method of claim 23, wherein the isolated stem cells are from bone marrow, periosteum, trabecular bone, adipose tissue, synovium, skeletal muscle, deciduous teeth, fetal pancreas, lung, liver, amniotic fluid, umbilical cord blood and umbilical cord tissues.

27. The method of claim 23, wherein the isolated stem cells are naturally occurring stem cells or are engineered stem cells.

28. The method of claim 23, wherein the isolated stem cells are embryonic stem cells, mesenchymal stem cells or induced pluripotent stem cells.

29. The method of claim 28, wherein the isolated stem cells are mesenchymal stem cells (MSCs) and are obtained by a method comprising:
   i) contacting a MSC-containing sample with a cell-derived preservation matrix generated by human bone marrow cells; and
   ii) isolating the MSCs from the cell-derived preservation extracellular matrix.

30. The method of claim 29, further comprising:
   iii) expanding the isolated MSCs on a cell-derived preservation extracellular matrix generated by human bone marrow cells.

31. The method of claim 29, wherein the MSC-containing sample is from bone marrow, periosteum, trabecular bone, adipose tissue, synovium, skeletal muscle, deciduous teeth, fetal pancreas, lung, liver, amniotic fluid, umbilical cord blood and umbilical cord tissues.

32. The method of claim 23, wherein the method further comprises contacting the stem cells with a second differentiation factor.

33. The method of claim 32, wherein the differentiated cell type is cardiomyocyte and the second differentiation factor is bFGF and azacytidine.

34. The method of claim 23, wherein the differentiation-inducing extracellular matrix is a 3D matrix.

35. The method of claim 23, wherein the differentiation-inducing extracellular matrix is free of feeder cells.

36. The method of claim 23, wherein the differentiation-inducing extracellular matrix is free of fibroblast cells.

37. The method of claim 23, wherein the surface is a surface of a cell culture dish or plate.

\* \* \* \* \*

UNITED STATES PATENT AND TRADEMARK OFFICE
CERTIFICATE OF CORRECTION

PATENT NO. : 9,617,511 B2
APPLICATION NO. : 13/821288
DATED : April 11, 2017
INVENTOR(S) : Xiao-Dong Chen Page 1 of 1

It is certified that error appears in the above-identified patent and that said Letters Patent is hereby corrected as shown below:

In the Claims

In Claim 1, Column 77, Line 17, delete "b" and replace with – by being – therefore.

Signed and Sealed this
Seventeenth Day of July, 2018

Andrei Iancu
*Director of the United States Patent and Trademark Office*